US012723238B2

(12) United States Patent
Schmidt et al.

(10) Patent No.: US 12,723,238 B2
(45) Date of Patent: Sep. 1, 2026

(54) HIGH FIDELITY RNA-PROGRAMMABLE ENDONUCLEASE SYSTEMS AND USES THEREOF

(71) Applicants: CRISPR THERAPEUTICS AG, Zug (CH); BAYER HEALTHCARE, LLC, Whippany, NJ (US)

(72) Inventors: Moritz Schmidt, Cologne (DE); Philipp Knyphausen, Cologne (DE); Christina Galonska, Cologne (DE); Wayne Coco, Cologne (DE); Andre Cohnen, Cologne (DE)

(73) Assignees: CRISPR THERAPEUTICS AG, Zug (CH); BAYER HEALTHCARE, LLC, Whippany, NJ (US)

( * ) Notice: Subject to any disclaimer, the term of this patent is extended or adjusted under 35 U.S.C. 154(b) by 1183 days.

(21) Appl. No.: 17/437,915

(22) PCT Filed: Mar. 12, 2020

(86) PCT No.: PCT/US2020/022394
§ 371 (c)(1),
(2) Date: Sep. 10, 2021

(87) PCT Pub. No.: WO2020/186059
PCT Pub. Date: Sep. 17, 2020

(65) Prior Publication Data

US 2022/0145274 A1 May 12, 2022

Related U.S. Application Data

(60) Provisional application No. 62/817,514, filed on Mar. 12, 2019.

(51) Int. Cl.

| | |
|---|---|
| ***C12N 9/22*** | (2006.01) |
| ***C12N 15/11*** | (2006.01) |
| ***C12N 15/90*** | (2006.01) |

(52) U.S. Cl.
CPC ................ *C12N 9/22* (2013.01); *C12N 15/11* (2013.01); *C12N 15/902* (2013.01); *C12N 2310/20* (2017.05); *C12N 2800/80* (2013.01)

(58) Field of Classification Search
CPC .............................. C12N 9/22; C12N 2310/20
See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts'o et al. |

(Continued)

FOREIGN PATENT DOCUMENTS

| | | | |
|---|---|---|---|
| WO | WO-9303769 | A1 | 3/1993 |
| WO | WO-9307883 | A1 | 4/1993 |

(Continued)

OTHER PUBLICATIONS

Ablain, Julien, et al. "A CRISPR/Cas9 Vector System for Tissue-Specific Gene Disruption in Zebrafish." Developmental Cell, vol. 32, No. 6, Mar. 2015, pp. 756-764, https://doi.org/10.1016/j.devcel.2015.01.032. (Year: 2015).*

(Continued)

*Primary Examiner* — Kimberly Chong
*Assistant Examiner* — Africa M McLeod
(74) *Attorney, Agent, or Firm* — Casimir Jones, S.C.; J. Mitchell Jones

(57) ABSTRACT

Described herein are novel systems for targeting, editing or manipulating DNA in a cell, using novel M-SmallCas9 nucleases and variants thereof. The M-SmallCas9 nucleases are derived from wildtype or parental small type II CRISPR Cas9 endonucleases, and display improved fidelity compared to parental type II CRISPR Cas9 enzymes in combi- (Continued)

nation with a simple PAM sequences and are small endonuclease size.

6 Claims, 2 Drawing Sheets

Specification includes a Sequence Listing.

(56) References Cited

U.S. PATENT DOCUMENTS 4,476,301 A 10/1984 Imbach et al.
4,587,044 A 5/1986 Miller et al.
4,605,735 A 8/1986 Miyoshi et al.
4,667,025 A 5/1987 Miyoshi et al.
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,845,205 A 7/1989 Huynh Dinh et al.
4,876,335 A 10/1989 Yamane et al.
4,904,582 A 2/1990 Tullis
4,948,882 A 8/1990 Ruth
4,958,013 A 9/1990 Letsinger
5,023,243 A 6/1991 Tullis
5,034,506 A 7/1991 Summerton et al.
5,082,830 A 1/1992 Brakel et al.
5,109,124 A 4/1992 Ramachandran et al.
5,112,963 A 5/1992 Pieles et al.
5,118,802 A 6/1992 Smith et al.
5,130,302 A 7/1992 Spielvogel et al.
5,134,066 A 7/1992 Rogers et al.
5,138,045 A 8/1992 Cook et al.
5,166,315 A 11/1992 Summerton et al.
5,173,414 A 12/1992 Lebkowski et al.
5,175,273 A 12/1992 Bischofberger et al.
5,177,196 A 1/1993 Meyer, Jr. et al.
5,185,444 A 2/1993 Summerton et al.
5,188,897 A 2/1993 Suhadolnik et al.
5,214,134 A 5/1993 Weis et al.
5,214,136 A 5/1993 Lin et al.
5,216,141 A 6/1993 Benner
5,218,105 A 6/1993 Cook et al.
5,222,982 A 6/1993 Ommaya
5,235,033 A 8/1993 Summerton et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,321,131 A 6/1994 Agrawal et al.
5,367,066 A 11/1994 Urdea et al.
5,371,241 A 12/1994 Brush
5,385,582 A 1/1995 Ommaya
5,391,723 A 2/1995 Priest
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,306 A 7/1996 Agrawal et al.
5,541,307 A 7/1996 Cook et al.
5,541,313 A 7/1996 Ruth
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,552 A 10/1996 Magda et al.
5,567,810 A 10/1996 Weis et al.
5,571,799 A 11/1996 Tkachuk et al.
5,574,142 A 11/1996 Meyer, Jr. et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,595,726 A 1/1997 Magda et al.
5,596,086 A 1/1997 Matteucci et al.
5,596,091 A 1/1997 Switzer
5,597,696 A 1/1997 Linn et al.
5,599,923 A 2/1997 Sessler et al.
5,599,928 A 2/1997 Hemmi et al.
5,602,240 A 2/1997 De Mesmaeker et al.
5,608,046 A 3/1997 Cook et al.
5,610,289 A 3/1997 Cook et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,633,360 A 5/1997 Bischofberger et al.
5,658,776 A 8/1997 Flotte et al.
5,663,312 A 9/1997 Chaturvedula
5,677,437 A 10/1997 Teng et al.
5,677,439 A 10/1997 Weis et al.
5,681,941 A 10/1997 Cook et al.
5,688,941 A 11/1997 Cook et al.
5,714,331 A 2/1998 Buchardt et al.
5,719,262 A 2/1998 Buchardt et al.
5,750,692 A 5/1998 Cook et al.
5,763,588 A 6/1998 Matteucci et al.
5,786,211 A 7/1998 Johnson
5,830,653 A 11/1998 Froehler et al.
5,843,780 A 12/1998 Thomson
5,871,982 A 2/1999 Wilson et al.
6,005,096 A 12/1999 Matteucci et al.
6,200,806 B1 3/2001 Thomson
6,258,595 B1 7/2001 Gao et al.
6,287,860 B1 9/2001 Monia et al.
7,029,913 B2 4/2006 Thomson
7,078,387 B1 7/2006 Leiden et al.
7,153,684 B1 12/2006 Hogan
7,169,874 B2 1/2007 Salamone et al.
2003/0022831 A1 1/2003 Rothbard et al.
2003/0032593 A1 2/2003 Wender et al.
2003/0083256 A1 5/2003 Rothbard et al.
2003/0158403 A1 8/2003 Manoharan et al.
2003/0220334 A1 11/2003 Wender et al.
2007/0254842 A1 11/2007 Bankiewicz

(56) References Cited

U.S. PATENT DOCUMENTS

| | | | |
|---|---|---|---|
| 2008/0081064 | A1 | 4/2008 | Jelle et al. |
| 2009/0047263 | A1 | 2/2009 | Yamanaka et al. |
| 2009/0068742 | A1 | 3/2009 | Yamanaka |
| 2009/0191159 | A1 | 7/2009 | Sakurada et al. |
| 2009/0196903 | A1 | 8/2009 | Kliman |
| 2009/0227032 | A1 | 9/2009 | Yamanaka et al. |
| 2009/0246875 | A1 | 10/2009 | Yamanaka et al. |
| 2009/0304646 | A1 | 12/2009 | Sakurada et al. |

FOREIGN PATENT DOCUMENTS

| | | | | |
|---|---|---|---|---|
| WO | WO-9309239 A1 | | 5/1993 | |
| WO | WO-9319191 A1 | | 9/1993 | |
| WO | WO-9412649 A2 | | 6/1994 | |
| WO | WO-9428938 A1 | | 12/1994 | |
| WO | WO-9500655 A1 | | 1/1995 | |
| WO | WO-9511984 A2 | | 5/1995 | |
| WO | WO-9513365 A1 | | 5/1995 | |
| WO | WO-9513392 A1 | | 5/1995 | |
| WO | WO-9617947 A1 | | 6/1996 | |
| WO | WO-9706243 A1 | | 2/1997 | |
| WO | WO-9708298 A1 | | 3/1997 | |
| WO | WO-9709441 A2 | | 3/1997 | |
| WO | WO-9721825 A1 | | 6/1997 | |
| WO | WO-9839352 A1 | | 9/1998 | |
| WO | WO-9911764 A2 | | 3/1999 | |
| WO | WO-9914226 A2 | | 3/1999 | |
| WO | WO-9920741 A1 | | 4/1999 | |
| WO | WO-2001018048 A2 | | 3/2001 | |
| WO | WO-0151616 A2 | | 7/2001 | |
| WO | WO-0183692 A2 | | 11/2001 | |
| WO | WO-03020920 A1 | | 3/2003 | |
| WO | 2013/176772 | | 11/2013 | |
| WO | WO-2013176722 A2 | | 11/2013 | |
| WO | WO-2014008334 A1 | | 1/2014 | |
| WO | 2015/089277 | | 6/2015 | |
| WO | WO-2015089288 A1 | | 6/2015 | |
| WO | WO-2015095340 A1 | | 6/2015 | |
| WO | WO-2015130584 A2 | | 9/2015 | |
| WO | 2015/153789 | | 10/2015 | |
| WO | 2017/040348 | | 3/2017 | |
| WO | WO-2017070622 A1 | | 4/2017 | |
| WO | WO-2017099823 A1 | | 6/2017 | |
| WO | WO-2017173054 A1 | | 10/2017 | |
| WO | WO-2018002719 A1 | | 1/2018 | |
| WO | WO-2018081480 A1 | | 5/2018 | |
| WO | WO-2019118935 A1 | | 6/2019 | |
| WO | WO-2019183150 A1 | * | 9/2019 | ............ C12N 15/11 |
| WO | WO-2020112908 A2 | * | 6/2020 | ......... A61K 48/0025 |
| WO | 2020186059 | | 9/2020 | |

OTHER PUBLICATIONS

Mehmet Fatih Bolukbasi et al: "Creating and evaluating accurate CRISPR-Cas9 scalpels for genomic surgery", Nature Methods, vol. 13, No. 1, Jan. 1, 2016 (Jan. 1, 2016), New York, pp. 41-50.

Anonymous: "CRISPR-associated endonuclease Cas1 [*Staphylococcus aureus*]—Protein—NCBI", May 9, 2015 (May 9, 2015), XP055711777, Retrieved from the Internet [retrieved on Jul. 6, 2020].

Anonymous: "CAS9 From *Staphylococcus Aureus*", Feb. 13, 2019 (Feb. 13, 2019), XP055711995, Retrieved from the Internet [retrieved on Jul. 6, 2020], 5 pages.

Anonymous: "Cas 9 from *Staphylococcus simulans*", Oct. 10, 2018 (Oct. 10, 2018), XP055712006, Retrieved from the Internet [retrieved on Jul. 6, 2020].

Hiroshi Nishimasu et al: "Crystal Structure of *Staphylococcus aureus* Cas9", Cell, vol. 162, No. 5, Aug. 1, 2015 (Aug. 1, 2015), Amsterdam, NL, pp. 1113-1126.

International Search Report, International Patent Application No. PCT/US2020/022394, mailed Sep. 14, 2020.

Aguilera et al., "Systemic in vivo distribution of activatable cell penetrating peptides is superior to that of cell penetrating peptides," Integrative Biology 2009, 1(5-6), 371-381.

Akyurek L.M., et al., "SM22alpha Promoter Targets Gene Expression to Vascular Smooth Muscle Cells in Vitro and in Vivo," Molecular Medicine, Nov. 2000, vol. 6, No. 11, pp. 983-991.

Ali R.R., et al., "Adeno-Associated Virus Gene Transfer to Mouse Retina," Human Gene Therapy, Jan. 1, 1998, vol. 9, No. 1, pp. 81-86.

Ali R.R., et al., "Gene Transfer Into the Mouse Retina Mediated by an Adeno-Associated Viral Vector," Human Molecular Genetics, May 1996, vol. 5, No. 5, pp. 591-594.

Altschul S.F., et al., "Basic Local Alignment Search Tool", Journal of Molecular Biology, vol. 215, No. 3, 1990, pp. 403-410.

Angart P., et al., "Design of SiRNA Therapeutics From the Molecular Scale," Pharmaceuticals, Basel, 2013, vol. 6, No. 4, pp. 440-468 (29 Pages).

Angel M., et al., "Innate Immune Suppression Enables Frequent Transfection with RNA Encoding Reprogramming Proteins," PLoS One, Jul. 23, 2010, vol. 5, No. 7: e11756, pp. 1-7, XP55047047.

Ausubel F.M., et al., "Short Protocols in Molecular Biology," Wiley & Sons, 1999, 21 pages, TOC only.

Baetge E.E., et al., "Transgenic Mice Express the Human Phenylethanolamine N-methyltransferase Gene in Adrenal Medulla and Retina," Proceedings of the National Academy of Sciences of the United States of America, May 1988, vol. 85, No. 10, pp. 3648-3652.

Barbour et al., "Characterization of the bipartite degron that regulates ubiquitin-independent degradation of thymidylate synthase," Bioscience Reports 2013, 33(1), in 19 pages.

Behlke, "Chemical modification of siRNAs for in vivo use," Oligonucleotides 2008, 18(4), 305-320.

Bennett J., et al., "Real-Time, Noninvasive in Vivo Assessment of Adeno-Associated Virus-mediated Retinal Transduction," Investigative Ophthalmology & Visual Science, Dec. 1997, vol. 38, No. 13, pp. 2857-2863.

Beumer et al., "Efficient gene targeting in Drosophila by direct embryo injection with zinc-finger nucleases," Proceedings of the National Academy of Sciences 2008, 105(50), 19821-19826.

Bitter G.A., et al., "Expression and Secretion Vectors for Yeast," Methods in Enzymology, 1987, vol. 153, pp. 516-544.

Borras T., et al., "Adenoviral Reporter Gene Transfer to the Human Trabecular Meshwork Does not Alter Aqueous Humor Outflow. Relevance for Potential Gene Therapy of Glaucoma," Gene Therapy, Apr. 1999, vol. 6, No. 4, pp. 515-524.

Boundy V.A., et al., "Regulation of Tyrosine Hydroxylase Promoter Activity by Chronic Morphine in TH9.0-lacZ Transgenic Mice," Journal of Neuroscience, Dec. 1, 1998, vol. 18, No. 23, pp. 9989-9995.

Braasch D.A., et al., "Novel Antisense and Peptide Nucleic Acid Strategies for Controlling Gene Expression," Biochemistry, Apr. 9, 2002, vol. 41, No. 14, pp. 4503-4510.

Bramsen J.B., et al., "Development of Therapeutic-Grade Small Interfering RNAs by Chemical Engineering," Frontiers in Genetics, Aug. 20, 2012, vol. 3, Article. 154, 22 Pages.

Burnett et al., "Current progress of siRNA/shRNA therapeutics in clinical trials," Biotechnology Journal 2011, 6(9), 1130-1146.

Carter B.J., "Adeno-Associated Virus Vectors," Current Opinion in Biotechnology, Oct. 1992, vol. 3, No. 5, pp. 533-539.

Casanova E., et al., "A CamKIIalpha ICre BAC Allows Brain-Specific Gene Inactivation," Genesis, Sep. 2001, vol. 31, No. 1, pp. 37-42.

Cekaite L., et al., "Gene Expression Analysis in Blood Cells in Response to Unmodified and 2'-Modified siRNAs Reveals TLR-Dependent and Independent Effects," Journal of Molecular Biology, 2007, vol. 365, pp. 90-108.

Chakrabarti P., "Promoting Adipose Specificity: The Adiponectin Promoter," Endocrinology, Jun. 2010, vol. 151, No. 6, pp. 2408-2410.

Chang X-B., et al., "Modification of DNA Ends Can Decrease End Joining Relative to Homologous Recombination in Mammalian Cells," Proceedings of the National Academy of Sciences of the United States of America, Jul. 1987, vol. 84, No. 14, pp. 4959-4963.

(56) References Cited

OTHER PUBLICATIONS

Chen S., et al., "A Lymphoproliferative Abnormality Associated With Inappropriate Expression of the Thy-1 Antigen in Transgenic Mice," Cell, Oct. 9, 1987, vol. 51, No. 1, pp. 7-19.
Chen X-L., et al., "Analysis of a 762-bp Proximal Leptin Promoter to Drive and Control Regulation of Transgene Expression of Growth Hormone Receptor in Mice," Biochemical and Biophysical Research Communications, Aug. 19, 1999, vol. 262, No. 1, pp. 187-192.
Chernolovskaya E.L., et al., "Chemical Modification of siRNA," Current Opinion in Molecular Therapy, 2010, vol. 12, No. 2, pp. 158-167 (11 Pages).
Cho et al., "Generation of transgenic mice," Current Protocols in Cell Biology 2009, 42(1), 19-11. 22 Pages.
Chu et al., "Recent progress with FKBP-derived destabilizing domains," Bioorganic & Medicinal Chemistry Letters 2008, 18(22), 5941-5944.
Citartan et al., "Assays for aptamer-based platforms," Biosensors and Bioelectronics 2012, 34(1), in 11 pages.
Clark et al., "A stable cell line carrying adenovirus-inducible rep and cap genes allows for infectivity titration of adeno-associated virus vectors," Gene Therapy 1996, 3(12), 1124-1132.
Comb M., et al., "Proteins Bound at Adjacent DNA Elements Act Synergistically to Regulate Human Proenkephalin cAMP Inducible Transcription," EMBO Journal, Dec. 1, 1988, vol. 7, No. 12, pp. 3793-3805.
Crooke et al., "Pharmacokinetic properties of several novel oligonucleotide analogs in mice," Journal of Pharmacology and Experimental Therapeutics 1996, 277(2), 923-937.
De Mesmaeker A., et al., "Antisense Oligonucleotides," Accounts of Chemical Research, 1995, vol. 28, No. 9, pp. 366-374.
Deleavey G.F., et al., "Chemical Modification of siRNA," Current Protocols in Nucleic Acid Chemistry, Dec. 2009, Chapter 16, (Supplement 39), Unit, pp. 16.3.1-16.3.22.
Dohmen R.J., et al., "Heat-inducible degron: a method for constructing temperature-sensitive mutants", Science (New York, N.Y. ), vol. 263, Mar. 4, 1994, pp. 1273-1276.
Englisch U., et al., "Chemically Modified Oligonucleotides as Probes and Inhibitors", Angewandte Chemie, International Edition, 1991, vol. 30, pp. 613-629.
Feng et al., "High-level expression and mutagenesis of recombinant human phosphatidylcholine transfer protein using a synthetic gene: evidence for a C-terminal membrane binding domain," Biochemistry 2000, 39(50), 15399-15409.
Flannery J.G., et al., "Efficient Photoreceptor-Targeted Gene Expression in Vivo by Recombinant Adeno-Associated Virus," Proceedings of the National Academy of Sciences of the United States of America, Jun. 1997, vol. 94, pp. 6916-6921.
Flotte T.R., et al., "Stable in Vivo Expression of the Cystic Fibrosis Transmembrane Conductance Regulator With an Adeno-Associated Virus Vector," Proceedings of the National Academy of Sciences of the United States of America, Nov. 15, 1993, vol. 90, No. 22, pp. 10613-10617.
Franz W.M., et., "Analysis of Tissue-specific Gene Delivery by Recombinant Adenoviruses Containing Cardiac-specific Promoters", Cardiovasc Research, Sep. 1997, vol. 35, No. 3, pp. 560-566.
Fucini R.V., et al., Adenosine Modification May Be Preferred for Reducing SiRNA Immune Stimulation, Nucleic Acid Therapeutics, 2012, vol. 22, No. 3, pp. 205-210.
Gaglione M., et al., "Recent Progress in Chemically Modified siRNAs," Mini-Reviews in Medical Chemistry, Jun. 2010, vol. 10, No. 7, pp. 578-595, 19 Pages.
Gama Sosa et al., "Animal transgenesis: an overview," Brain Structure and Function 2010, 214, 91-109.
Gebeyehu G., et al., "Novel Biotinylated Nucleotide—Analogs for Labeling and Colorimetric Detection of DNA," Nucleic Acids Research, 1987, vol. 15, No. 11, pp. 4513-4534.
Greussing et al., "Monitoring of ubiquitin-proteasome activity in living cells using a Degron (dgn)-destabilized green fluorescent protein (GFP)-based reporter protein," JoVE (Journal of Visualized Experiments) 2012, 69, in 8 pages.
Heasman J., et al., "Morpholino Oligos: Making Sense of Antisense?," Developmental Biology, 2002, vol. 243, No. 2, pp. 209-214.
Hermonat P.L., et al. "Use of Adeno-associated Virus as a Mammalian DNA Cloning Vector: Transduction of Neomycin Resistance into Mammalian Tissue Culture Cells." Proceedings of the National Academy of Sciences of the United States of America, Oct. 1984, vol. 81, No. 20, pp. 6466-6470.
Hunter J.J., et al., "Targeting Gene Expression to Specific Cardiovascular Cell Types in Transgenic Mice", Hypertension, Oct. 1993, vol. 22, No. 4, pp. 608-617.
Husaini A.M., et al., "Approaches for Gene Targeting and Targeted Gene Expression in Plants," GM Crops, Jun.-Dec. 2011, vol. 2, No. 3, pp. 150-162.
Jomary C., et al., "Rescue of Photoreceptor Function by AAV-Mediated Gene Transfer In a Mouse Model of Inherited Retinal Degeneration," Gene Therapy, Jul. 1997, vol. 4, No. 7, pp. 683-690.
Judge A., et al., "Overcoming the Innate Immune Response to Small Interfering RNA," Human Gene Therapy, Feb. 2008, vol. 19, No. 2, pp. 111-124 (14 Pages).
Judge A.D., "Design of Noninflammatory Synthetic SiRNA Mediating Potent Gene Silencing in Vivo," Molecular Therapy, Mar. 2006, vol. 13, No. 3, pp. 494-505.
Kabanov A.V., et al., "A New Class of Antivirals: Antisense Oligonucleotides Combined with a Hydrophobic Substituent Effectively Inhibit Influenza Virus Reproduction and Synthesis of Virus-specific Proteins in MDCK Cells," FEBS Letter, Jan. 1990, vol. 259, No. 2, pp. 327-330.
Kanasty R.L., et al., "Action and Reaction: The Biological Response to SiRNA and Its Delivery Vehicles," Molecular Therapy, Mar. 2012, vol. 20, No. 3, pp. 513-524 (13 Pages).
Kaneda N., et al., "Tissue-Specific and High-Level Expression of the Human Tyrosine Hydroxylase Gene in Transgenic Mice," Neuron, Apr. 1991, vol. 6, No. 4, pp. 583-594.
Kanemaki, "Frontiers of protein expression control with conditional degrons," PflUgers Archiv-European Journal of Physiology 2013, 465, 419-425.
Kariko K., et al., "Suppression of RNA Recognition by Toll-Like Receptors: The Impact of Nucleoside Modification and the Evolutionary Origin of RNA," Immunity, Cell press, US LNKD, Aug. 23, 2005, vol. 23, No. 2, pp. 165-175, DOI: 10.1016/J.IMMUNI.2005.06.008, ISSN: 1074-7613, XP008104240.
Kawai S., et al., "Transformation of Saccharomyces Cerevisiae and Other Fungi: Methods and Possible Underlying Mechanism," Bioengineered Bugs, Nov.-Dec. 2010, vol. 1, No. 6, pp. 395-403.
Kim S., et al., "A serum Response Factor-dependent Transcriptional Regulatory Program Identifies Distinct Smooth Muscle Cell Sublineages," Molecular and Cellular Biology, Apr. 1997, vol. 17, No. 4, pp. 2266-2278.
Kita A., et al., "Identification of the Promoter Region Required For Human Adiponectin Gene Transcription: Association With CCAAT/Enhancer Binding Protein-beta And Tumor Necrosis Factor-Alpha," Biochemical and Biophysical Research Communications, Jun. 3, 2005, vol. 331, No. 2, pp. 484-490.
Knight J.B., et al., "Regulation of the Human GLUT4 Gene Promoter:Interaction Between a Transcriptional Activatorand Myocyte Enhancer Factor 2A," Proceedings of the National Academy of Sciences of the United States of America, 2003, vol. 100, No. 25, pp. 14725-14730.
Kole et al., "RNA therapeutics: beyond RNA interference and antisense oligonucleotides," Nature Reviews Drug Discovery 2012, 11(2), 125-140.
Kormann M.S.D., et al., "Expression of Therapeutic Proteins After Delivery of Chemically Modified mRNA in Mice," Nature Biotechnology, Feb. 2011, vol. 29, No. 2, pp. 154-157, ISSN 1546-1696, XP002696192.
Kornberg A., "DNA Replication," W. H. Freeman and Company, San Francisco, 1980, pp. 75-77 (6 Pages).
Koshimizu et al., "Functional requirement of gp130-mediated signaling for growth and survival of mouse primordial germ cells in vitro and derivation of embryonic germ (EG) cells," Development 1996, 122(4), pp. 1235-1242.
Koshkin A.A., et al., "LNA (locked nucleic acids): synthesis of the adenine, cytosine, guanine 5—methylcytosine, thymine and uracil

(56) References Cited

OTHER PUBLICATIONS bicyclonucleoside monomers, oligomerisation, and unprecedented nucleic acid recognition", Tetrahedron, 1998, vol. 54, No. 14, pp. 3607-3630.
Kroschwitz J.I., "The Concise Encyclopedia of Polymer Science and Engineering", 1990, pp. 858-859.
Kuriki C., et al., "Structural and Functional Analysis of a New Upstream Promoter of the Human FAT/CD36 Gene," Biological and Pharmaceutical Bulletin, Nov. 2002, vol. 25, No. 11, pp. 1476-1478.
Lacerra G., et al., "Restoration of Hemoglobin a Synthesis in Erythroid Cells From Peripheral Blood of Thalassemic Patients," Proceedings of the National Academy of Sciences of the United States of America, Aug. 15, 2000, vol. 97, No. 17, pp. 9591-9596.
Langer R., "New Methods of Drug Delivery," Science, New Series, Sep. 28, 1990, vol. 249, No. 4976, pp. 1527-1533.
Laughlin C.A., et al., "Cloning of Infectious Adeno-Associated Virus Genomes in Bacterial Plasmids," Gene, 1983, vol. 23, No. 1, pp. 65-73.
Lebkowski J.S., et al., "Adeno-associated Virus: a Vector System for Efficient Introduction and Integration of DNA Into a Variety of Mammalian Cell Types," Molecular and Cellular Biology, Oct. 1988, vol. 8, No. 10, pp. 3988-3996.
Letsinger R.L., et al., "Cholesteryl-conjugated Oligonucleotides: Synthesis, Properties, and Activity as Inhibitors of Replication of Human Immunodeficiency Virus in Cell Culture," Proceedings of the National Academy of Sciences of the United States of America, Sep. 1989, vol. 86, pp. 6553-6556.
Li L., et al., "Expression of the SM22alpha Promoter in Transgenic Mice Provides Evidence for Distinct Transcriptional Regulatory Programs in Vascular and Visceral Smooth Muscle Cells," Journal of Cell Biology, Mar. 1996, vol. 132, No. 5, pp. 849-859.
Li T., et al., "In Vivo Transfer of a Reporter Gene to the Retina Mediated by an Adenoviral Vector," Investigative Ophthalmology & Visual Science, Apr. 1994, vol. 35, No. 5, pp. 2543-2549.
Li T., et al., "Phenotype Correction in Retinal Pigment Epithelium in Murine Mucopolysaccharidosis VII by Adenovirus-Mediated Gene Transfer," Proceedings of the National Academy of Sciences of the United States of America, Aug. 15, 1995, vol. 92, No. 17, pp. 7700-7704.
Liberman & Wedekind, "Riboswitch structure in the ligand-free state," Wiley Interdisciplinary Reviews: RNA 2012, 3(3), 369-384.
Linn S.C., et al., Conservation of an AE3 CI-/HCO3-Exchanger Cardiacspecific Exon and Promoter Region and AE3 mRNA Expression Patterns in Murine and Human Hearts, Circulation Research, Apr. 1995, vol. 76, No. 4, pp. 584-591.
Liu B.H., et al., "CMV Enhancer/human PDGF-(beta) Promoter for Neuronspecific Transgene Expression," Gene Therapy, Jan. 2004, vol. 11, No. 1, pp. 52-60.
Llewellyn M.E., et al., "Orderly Recruitment of Motor Units Under Optical Control in Vivo," Nature Medicine, Oct. 2010, vol. 16, No. 10, pp. 1161-1165 (6 Pages).
Loakes & Brown, "5-Nitroindole as an universal base analogue," Nucleic Acids Research 1994, 22(20), 4039-4043.
Ma H., et al., "Pol III Promoters to Express Small RNAs: Delineation of Transcription Initiation," Molecular Therapy—Nucleic Acids, 2014, vol. 3, No. 5, Article No. e161, 11 Pages.
Mae et al. "Chemically modified cell-penetrating peptides for the delivery of nucleic acids," Expert Opinion on Drug Delivery 2009, 6(11), 1195-1205.
Manoharan et al., "Cholic acid-oligonucleotide conjugates for antisense applications," Bioorganic & Medicinal Chemistry Letters 1994, 4(8), 1053-1060.
Manoharan et al., "Lipidic nucleic acids," Tetrahedron Letters 1995, 36(21), 3651-3654.
Manoharan M., et al., "Chemical Modifications to Improve Uptake and Bioavailability of Antisense Oligonucleotides," Annals New York Academy of Sciences, 1992, vol. 660, pp. 306-309.
Manoharan M., et al., "Introduction of a Lipophilic Thioether Tether in the Minor Groove of Nucleic Acids for Antisense Applications," Bioorganic & Medicinal Chemistry Letters, 1993, vol. 3, No. 12, pp. 2765-2770.
Manoharan M., et al., "Oligonucleotide Conjugates: Alteration of the Pharmacokinetic Properties of Antisense Agents," Nucleosides & Nucleotides, 1995, vol. 14, No. 3-5, pp. 969-973 (6 Pages).
Martin P., "A New Access to 2'-O-Alkylated Ribonucleosides and Properties of 2'-O-Alkylated Oligoribonucleotides," Helvetica Chimica Acta, 1995, vol. 78, pp. 486-504. (in German with English abstract).
Mason M.M., et al., "Regulation of Leptin Promoter Function by Sp1, C/EBP, and a Novel Factor," Endocrinology, Mar. 1998, vol. 139, No. 3, pp. 1013-1022.
Matsui Y., et al., "Derivation of Pluripotential Embryonic Stem Cells from Murine Primordial Germ Cells in Culture," Cell, 1992, vol. 70, No. 5, pp. 841-847.
Mayford M., et al., "The 3'-Untranslated Region of CaMKII(Alpha) is a Cis-acting Signal for the Localization and Translation of mRNA in Dendrites," Proceedings of the National Academy of Sciences of the United States of America, Nov. 1996, vol. 93, pp. 13250-13255.
McLaughlin S.K., et al., "Adeno-associated Virus General Transduction Vectors: Analysis of Proviral Structures," Journal of Virology, Jun. 1988, vol. 62, No. 6, pp. 1963-1973.
Mendelson E., et al., "Expression and Rescue of a Nonselected Marker From an Integrated AAV Vector," Virology, Sep. 1988, vol. 166, No. 1, pp. 154-165.
Mishra R.K., et al., "Improved Leishmanicidal Effect of Phosphorothioate Antisense Oligonucleotides by LDL-Mediated Delivery," Biochimica et Biophysica Acta, 1995, vol. 1264, pp. 229-237.
Miyagishi M., et al., "U6 Promoter-Driven siRNAs With Four Uridine 3' Overhangs Efficiently Suppress Targeted Gene Expression in Mammalian Cells," Nature Biotechnology, May 2002, vol. 20, No. 5, pp. 497-500.
Miyoshi H., et al., "Stable and Efficient Gene Transfer into the Retina Using an HIV-Based Lentiviral Vector," Proceedings of the National Academy of Sciences of the United States of America, Sep. 16, 1997, vol. 94, No. 19, pp. 10319-10323.
Moessler H., et al., "The SM 22 Promoter Directs Tissue-specific Expression in Arterial but Not in Venous or Visceral Smooth Muscle Cells in Transgenic Mice," Development 122, Aug. 1996, vol. 122, No. 8, pp. 2415-2425.
Morcos P.A., "Achieving Efficient Delivery of Morpholino Oligos in Cultured Cells," Genesis, 2001, vol. 30, No. 3, pp. 94-102.
Morrison S.J., et al., "Regulatory Mechanisms in Stem Cell Biology," Cell, Feb. 7, 1997, vol. 88, No. 3, pp. 287-298.
Muzyczka N., "Use of Adeno-Associated Virus as a General Transduction Vector for Mammalian Cells," Current Topics in Microbiology and Immunology, 1992, vol. 158, pp. 97-129.
Nakamura et al., "RNA plasticity and selectivity applicable to therapeutics and novel biosensor development," Genes to Cells 2012, 17(5), 344-364.
Nasevicius A., et al., "Effective Targeted Gene 'Knockdown' in Zebrafish," Nature Genetics, Nov. 2000, vol. 26, No. 2, pp. 216-220.
NCBI GenBank: "5-HT1C Serotonin Receptor (Promoter Region) [Mice, Genomic, 1859 nt]," GenBank No. S62283.1, Aug. 25, 1993, [Retrieved Feb. 14, 2024], 2 Pages.
NCBI GenBank: "Human Neurofilament Light Chain (NEFL) Gene, Promoter Region", GenBank Hlimnfl: L04147.1, Jan. 7, 1995, [Retrieved on Feb. 14, 2024], 2 Pages.
NCBI GenBank: "Human Synapsin I Gene, 5' End", GenBank HUMSYNIB No. M55301.1 , Jan. 13, 1995, [Retrieved Feb. 14, 2024], 2 Pages.
Nehls M., et al., "Two Genetically Separable Steps in the Differentiation of Thymic Epithelium", Science, vol. 272, May 10, 1996, pp. 886-889.
New R.R.C., "Liposomes: A Practical Approach," Oxford University Press, 1990, TOC only, 6 pages.
Nichols et al., "A universal nucleoside for use at ambiguous sites in DNA primers," Nature 1994, 369(6480), pp. 492-493.
Nicoud M., et al., "Development of Photoreceptor-Specific Promoters and Their Utility to Investigate EIAV Lentiviral Vector Mediated Gene Transfer to Photoreceptors," The Journal of Gene Medicine, Dec. 2007, vol. 9, No. 12, pp. 1015-1023.

(56) References Cited

OTHER PUBLICATIONS

Nielsen P.E., et al., "Sequence-selective recognition of DNA by strand displacement with a thymine-substituted polyamide," Science, 1991, vol. 254, pp. 1497-1500.
Noguchi H., et al., "PDX-1 Protein Containing Its Own Antennapedia-Like Protein Transduction Domain Can Transduce Pancreatic Duct and Islet Cells", Diabetes, Jul. 2003, vol. 52, No. 7, pp. 1732-1737.
Oberdick J., et al., "A Promoter That Drives Transgene Expression in Cerebellar Purkinje and Retinal Bipolar Neurons," Science, Apr. 13, 1990, vol. 248 (4952), pp. 223-226.
Oberhauser B., et al., "Effective Incorporation of 2'-O-methyl-oligoribonucleotides Into Liposomes and Enhanced Cell Association Through Modification With Thiocholesterol," Nucleic Acids Research, 1992, vol. 20, No. 3, pp. 533-538.
Oh MS., et al., "Expression of Transgenes in Midbrain Dopamine Neurons Using the Tyrosine Hydroxylase Promoter," Gene Therapy, Mar. 2009, vol. 16, No. 3, pp. 437-440.
Olson et al., "Preparation of liposomes of defined size distribution by extrusion through polycarbonate membranes," Biochimica et Biophysica Acta (BBA)—Biomembranes 1979, 557(1), 9-23.
Outchkourov et al., "Optimization of the expression of equistatin in Pichia pastoris," Protein Expression and Purification 2002, 24(1), 18-24.
Pajvani U.B., et al., "Fat Apoptosis Through Targeted Activation of Caspase 8: a New Mouse Model of Inducible and Reversible Lipoatrophy," Nature Medicine, Jul. 2005, vol. 11, No. 7, pp. 797-803.
Panyam J., et al., "Biodegradable Nanoparticles for Drug and Gene Delivery to Cells and Tissue," Advanced Drug Delivery Reviews, 2012, vol. 64, (supplement), pp. 61-71.
Parmacek M.S., et al., "A Novel Myogenic Regulatory Circuit Controls Slow/Cardiac Troponin C Gene Transcription in Skeletal Muscle," Molecular Cell Biology, Mar. 1994, vol. 14, No. 3, pp. 1870-1885.
Paul R.W., et al., "Increased Viral Titer Through Concentration of Viral Harvests from Retroviral Packaging Lines," Human Gene Therapy, 1993, vol. 4, No. 5, pp. 609-615.
Peer D., et al., "Special Delivery: Targeted Therapy with Small RNAs," Gene Therapy, 2011, vol. 18, pp. 1127-1133.
Perrin P., et al., "An Experimental Rabies Vaccine Produced With a New BHK-21 Suspension Cell Culture Process: Use of Serum-Free Medium and Perfusion-Reactor System," Vaccine, 1995, vol. 13, No. 13, pp. 1244-1250.
Platt K.A., et al., "Obesity-Linked Regulation of the Adipsin Gene Promoter in Transgenic Mice," Proceedings of the National Academy of Sciences of the United States of America, Oct. 1989, vol. 86, pp. 7490-7494.
Podesta & Kostarelos, "Engineering cationic liposome: sirna complexes for in vitro and in vivo delivery," Methods in Enzymology 2009, 464, 343-354.
Radovick S., et al., "Migratory Arrest of Gonadotropin-Releasing Hormone Neurons in Transgenic Mice," Proceedings of the National Academy of Sciences of the United States of America, Apr. 15, 1991, vol. 88, No. 8, pp. 3402-3406.
Robbins J., et al., "In Vivo Definition of a Cardiac Specific Promoter and Its Potential Utility in Remodeling the Heart," Annals of the New York Academy of Sciences, Mar. 27, 1995, vol. 752, pp. 492-505.
Rolling F., et al., "Evaluation of Adeno-Associated Virus-Mediated Gene Transfer Into the Rat Retina by Clinical Fluorescence Photography," Humne Gene Therapy, Mar. 1, 1999, vol. 10, No. 4, pp. 641-648.
Ross S.R., et al., "A Fat-specific Enhancer Is the Primary Determinant of Gene Expression for Adipocyte P2 in Vivo," Proceedings of the National Academy of Sciences of the United States of America, 1990, vol. 87, pp. 9590-9594.
Saison-Behmoaras T., et al., "Short Modified Antisense Oligonucleotides Directed Against Ha-ras Point Mutation Induce Selective Cleavage of the mRNA and Inhibit T24 Cells Proliferation", The EMBO Journal, vol. 10, No. 5, 1991, pp. 1111-1118.
Sakamoto T., et al., "A Vitrectomy Improves the Transfection Efficiency of Adenoviral Vector-mediated Gene Transfer to Muller Cells," Gene Therapy, Aug. 1998, vol. 5, No. 8, pp. 1088-1097.
Samulski R.J., et al., "Cloning of Adeno-associated Virus Into PBR322: Rescue of Intact Virus From the Recombinant Plasmid in Human Cells," Proceedings of the National Academy of Sciences of the United States of America, Mar. 1982, vol. 79, No. 6, pp. 2077-2081.
Samulski R.J., et al., "Helper-Free Stocks of Recombinant Adeno-associated Viruses: Normal Integration Does Not Require Viral Gene Expression," Journal of Virology, Sep. 1989, vol. 63, No. 9, pp. 3822-3828.
Sanghvi, Y.S., Chapter 15, Antisense Research and Applications, Crooke, S.T. and Lebleu, B., Eds., CRC Press, 1993, 273-288. (19 pages).
Sartorelli V., et al., "Myocardial Activation of the Human Cardiac Alphaactin Promoter by Helix-loop-helix Proteins," Proceedings of the National Academy of Sciences of the United States of America, May 1, 1992, vol. 89, No. 9, pp. 4047-4051.
Sasaoka T., et al., "Analysis of the Human Tyrosine Hydroxylase Promoter-chloramphenicol Acetyltransferase Chimeric Gene Expression in Transgenic Mice," Molecular Brain Research, Dec. 1992, vol. 16, (3-4), pp. 274-286.
Sato O., et al., "Dual Promoter Structure of Mouse and Human Fatty Acid Translocase/cd36 Genes and Unique Transcriptional Activation by Peroxisome Proliferator-activated Receptor Alpha and Gamma Ligands," Journal of Biological Chemistry, May 3, 2002, vol. 277, No. 18, pp. 15703-15711.
Schoeber et al., "Conditional fast expression and function of multimeric TRPV5 channels using Shield-1," American Journal of Physiology-Renal Physiology 2009, 296(1), F204-F211.
Senapathy P., et al., "Molecular Cloning of Adeno-associated Virus Variant Genomes and Generation of Infectious Virus by Recombination in Mammalian Cells," The Journal of Biological Chemistry, 1984, vol. 259, No. 7, pp. 4661-4666.
Seo J.B., et al., "Functional Characterization of the Human Resistin Promoter With Adipocyte Determination- and Differentiation-dependent Factor 1/Sterol Regulatory Element Binding Protein 1c and Ccaat Enhancer Binding Protein-(Alpha)," Molecular Endocrinology, Aug. 2003, vol. 17, No. 8, pp. 1522-1533.
Shamblott et al., "Human embryonic germ cell derivatives express a broad range of developmentally distinct markers and proliferate extensively in vitro," Proceedings of the National Academy of Sciences 2001, 98(1), 113-118.
Shamblott M.J., et al., "Derivation of Pluripotent Stem Cells From Cultured Human Primordial Germ Cells," Proceedings of the National Academy of Sciences of the United States of America, Nov. 10, 1998, vol. 95, No. 23, pp. 13726-13731.
Shea R.G., et al., "Synthesis, Hybridization Properties and Antiviral Activity of Lipid-Oligodeoxynucleotide Conjugates," Nucleic Acids Research, 1990, vol. 18, No. 13, pp. 3777-3783.
Singh K.S., et al., "LNA (Locked Nucleic Acids): Synthesis and High-Affinity Nucleic Acid Recognition," Chemical Communications, 1998, vol. 4, pp. 455-456.
Smith T.F., et al., "Comparison of Biosequences", Advances in Applied Mathematics, 1981, vol. 2, No. 4, pp. 482-489.
Soutschek J., et al., "Therapeutic Silencing of an Endogenous Gene by Systemic Administration of Modified siRNAs," Nature, Nov. 11, 2004, vol. 432, pp. 173-178 (7 Pages).
Svinarchuk F.P., et al., "Inhibition of HIV Proliferation in MT-4 Cells by Antisense Oligonucleotide Conjugated to Lipophilic Groups," Biochimie, 1993, vol. 75, pp. 49-54.
Szoka et al., "Preparation of unilamellar liposomes of intermediate size (0.1-0.2 μm) by a combination of reverse phase evaporation and extrusion through polycarbonate membranes," Biochimica et Biophysica Acta (BBA)-Biomembranes 1980, 601, 559-571.
Tabor D.E., et al., "Identification of Conserved Cis-elements and Transcription Factors Required for Sterol-regulated Transcription of Stearoyl-CoA Desaturase 1 and 2," Journal of Biological Chemistry, Jul. 16, 1999, vol. 274, No. 29, pp. 20603-20610.
Takahashi et al., "Induction of pluripotent stem cells from fibroblast cultures," Nature Protocols 2007, 2(12), 3081-3089.

(56) References Cited

OTHER PUBLICATIONS

Takahashi K., et al., "Induction of Pluripotent Stem Cells from Adult Human Fibroblasts by Defined Factors," Cell, Nov. 30, 2007, vol. 131, No. 5, pp. 861-872.
Takahashi M., et al., "Rescue From Photoreceptor Degeneration in the rd Mouse by Human Immunodeficiency Virus Vector-mediated Gene Transfer", Journal of Virology, Sep. 1999, vol. 73, No. 9, pp. 7812-7816.
Tanka M., et al., "Conformational Variations in an Infectious Protein Determine Prion Strain Differences," Nature, Mar. 18, 2004, vol. 428, No. 6980, pp. 323-328.
Thomson J.A., et al., "Embryonic Stem Cell Lines Derived From Human Blastocysts," Science, Nov. 6, 1998, vol. 282, No. 5391, pp. 1145-1147, 4 Pages.
Thomson J.A., et al., "Isolation of a Primate Embryonic Stem Cell Line," Proceedings of the National Academy of Sciences, vol. 92, Aug. 1995, pp. 7844-7848.
Thomson J.A., et al., "Pluripotent Cell Lines Derived From Common Marmoset (*Callithrix jacchus*) Blastocysts," Biology of Reproduction, Aug. 1996, vol. 55, No. 2, pp. 254-259.
Tozzo E., et al., "Amelioration of Insulin Resistance In Streptozotocin Diabetic Mice by Transgenic Overexpression of GLUT4 Driven by an Adipose-Specific Promoter," Endocrinology, Apr. 1997, vol. 138, No. 4, pp. 1604-1611.
Tratschin J-D., et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology, Oct. 1984, vol. 4, No. 10, pp. 2072-2081.
Tratschin J-D., et al., "Adeno-associated Virus Vector for High-frequency Integration, Expression, and Rescue of Genes in Mammalian Cells," Molecular and Cellular Biology, Nov. 1985, vol. 5, No. 11, pp. 3251-3260.
Trehin R., et al., "Cellular Uptake But Low Permeation of Human Calcitonin-Derived Cell Penetrating Peptides and Tat(47-57) Through Well-Differentiated Epithelial Models," Pharmaceutical Research, vol. 21, No. 7, Jul. 2004, pp. 1248-1256.
Vavalle & Cohen, "The REG1 anticoagulation system: a novel actively controlled factor IX inhibitor using RNA aptamer technology for treatment of acute coronary syndrome," Future Cardiology 2012, 8(3), 371-382.
Vemuri & Rhodes, "Preparation and characterization of liposomes as therapeutic delivery systems: a review," Pharmaceutica Acta Helvetiae 1995, 70(2), 95-111.
Volkov A.A., et al., "Selective Protection of Nuclease-sensitive Sites in siRNA Prolongs Silencing Effect," Oligonucleotides, 2009, vol. 19, No. 2, pp. 191-202.
Wahlestedt C., et al., "Potent and nontoxic antisense oligonucleotides containing locked nucleic acids," Proceedings of the National Academy of Sciences USA, May 9, 2000, vol. 97 (10), pp. 5633-5638.
Wang J., et al., "Cyclohexene Nucleic Acids (CeNA): Serum Stable Oligonucleotides that Activate RNase H and Increase Duplex Stability with Complementary RNA," Journal of the American Chemical Society, 2000, vol. 122, pp. 8595-8602.
Warren L., et al., "Highly Efficient Reprogramming to Pluripotency and Directed Differentiation of Human Cells with Synthetic Modified mRNA," Cell Stem Cell, Elsevier, Cell Press, Amsterdam, NL, Nov. 5, 2010, vol. 7, No. 5, pp. 618-630, (Sep. 30, 2010), DOI: 10.1016/J.STEM.2010.08.012, ISSN 1934-5909, XP002640639.
Watkins & Santalucia, "Nearest-neighbor thermodynamics of deoxyinosine pairs in DNA duplexes," Nucleic Acids Research 2005, 33(19), 6258-6267.
Watwe & Bellare, "Manufacture of liposomes: a review," Current Science 1995, 68 715-724.
Wender P.A., et al., "The Design, Synthesis, and Evaluation of Molecules That Enable or Enhance Cellular Uptake: Peptoid Molecular Transporters", Proceedings of the National Academy of Sciences of the United States of America, vol. 97, No. 24, Nov. 21, 2000, pp. 13003-13008.
Whitehead K.A., et al., "Silencing or Stimulation? siRNA Delivery and the Immune System," Annual Review of Chemical and Biomolecular Engineering, 2011, vol. 2, pp. 77-96 (23 Pages).
Winkler, "Oligonucleotide conjugates for therapeutic applications," Therapeutic Delivery 2013, 4(7), 791-809.
Xia X.G., et al., "An Enhanced U6 Promoter for Synthesis of Short Hairpin RNA," Nucleic Acids Research, 2003, vol. 31, No. 17 (e100), pp. 1-5.
Yang & Bedford, "Titivated for destruction: the methyl degron," Molecular Cell 2012, 48(4), 487-488.
Yokoyama T., et al., "Photoreceptor-Specific Activity of the Human Interphotoreceptor Retinoid-Binding Protein (IRBP) Promoter in Transgenic Mice," Experimental Eye Research, Aug. 1992, vol. 55, No. 2, pp. 225-233.
Young J.E., et al., "A Short, Highly Active Photoreceptor-specific Enhancer/Promoter Region Upstream of the Human Rhodopsin Kinase Gene," Investigative Ophthalmology & Visual Science, Sep. 2003, vol. 44, No. 9, pp. 4076-4085.
Yu J., et al., "Induced Pluripotent Stem Cell Lines Derived from Human Somatic Cells," Science, Dec. 21, 2007, vol. 318, No. 5858, pp. 1917-1920.
Zender L., et al., "VP22-Mediated Intercellular Transport of p53 in Hepatoma Cells in Vitro and in Vivo", Cancer Gene Therapy, vol. 9, No. 6, 2002, pp. 489-496.
Zhang and Madden, PowerBLAST: a new network BLAST application for interactive or automated sequence analysis and annotation, Genome Res., 1997, 7, 649-656.

* cited by examiner

HIGH FIDELITY RNA-PROGRAMMABLE ENDONUCLEASE SYSTEMS AND USES THEREOF

RELATED APPLICATIONS

This application is a National Stage Entry of PCT/US20/22394, filed Mar. 12, 2020, which claims the benefit of U.S. Provisional Patent Application Ser. No. 62/817,514, filed Mar. 12, 2019. The entire contents of which are incorporated herein by reference.

SEQUENCE LISTING

The text of the computer readable sequence listing filed Sep. 10, 2021, titled "CBTN_032PC_ST25.txt", created Sep. 10, 2021, having a file size of 126,776 bytes, is hereby incorporated by reference in its entirety.

FIELD OF THE INVENTION

The present disclosure generally relates to the field of molecular biology, in particular novel nucleases for gene editing.

BACKGROUND

Editing genomes using the RNA-guided DNA targeting principle of CRISPR (Clustered Regularly Interspaced Short Palindromic Repeats)-Cas (CRISPR associated proteins), has been widely exploited over the past few years. Three types of CRISPR-Cas systems (type I, type II and IIb, type III, and type V) have been described. Most uses of CRISPR-Cas for genome editing have been with a type II system. The main advantage provided by the bacterial type II CRISPR-Cas system lies in the minimal requirement for programmable DNA interference: an endonuclease, Cas9, guided by a customizable dual-RNA structure. As initially demonstrated in the original type II system of *Streptococcus pyogenes*, trans-activating CRISPR RNA (tracrRNA) binds to the invariable repeats of precursor CRISPR RNA (pre-crRNA) forming a dual-RNA that is essential for both RNA co-maturation by RNase Ill in the presence of Cas9, and invading DNA cleavage by Cas9. As demonstrated in *Streptococcus pyogenes*, Cas9 guided by the duplex formed between mature activating tracrRNA and targeting crRNA introduces site-specific double-stranded DNA (dsDNA) breaks in the invading cognate DNA. Cas9 is a multi-domain enzyme that uses an HNH nuclease domain to cleave the target strand (defined as complementary to the spacer sequence of crRNA) and a RuvC-like domain to cleave the non-target strand. The nuclease can act as a nickase by selective motif inactivation of the nuclease. DNA cleavage specificity is determined by two parameters: the variable, spacer-derived sequence of crRNA targeting the protospacer sequence (the sequence on the DNA target that is non-complementary to the spacer of crRNA) and a short sequence, the Protospacer Adjacent Motif (PAM), located immediately 3' (downstream) of the protospacer on the non-target DNA strand.

Studies have demonstrated that RNA-guided Cas9 can be employed as genome editing tool in a variety of cells including those of prokaryotes and eukaryotes including human. The system is versatile, enabling multiplex genome engineering by programming Cas9 to edit several sites in a genome simultaneously by using multiple guide RNAs. The conversion of Cas9 into a nickase was shown to facilitate homology-directed repair in mammalian genomes with reduced mutagenic activity. In addition, the DNA-binding activity of a Cas9 catalytic inactive mutant has for example been exploited to engineer RNA-programmable transcriptional silencing and activating devices or epigenetic modifiers.

Genome editing in mammalian cells has been limited, in part, by the size of Cas9 proteins. Cas9 from *Staphylococcus pyogenes* (SpyCas9), the enzyme most widely used to date, comprises approximately 4.2 kb of DNA (WO2013/176722) and a direct combination with cognate single guide RNAs (sgRNA) further increases the size. Adeno-associated viruses are among the vectors used for the delivery of Cas9 enzymes in gene therapy applications. However, AAV cargo size is restricted to about 4.5 kb. Because of the size constraints, delivering a Cas9 with its sgRNA and a potential DNA repair template can be an impediment to using the methods. Smaller Cas9 molecules have been characterized, but most of them suffer from a protospacer adjacent motif (PAM) sequence that is not as well defined as the one used by SpyCas9. For example, *Staphylococcus aureus* (SauCas9 uses an "NNGRR (T)" sequence, where R=A or G, and *Campylobacter jejuni* (Cja) Cas9 uses a "NNNACAC"/"NNNRYAC" PAM (where Y=T or G), respectively. The PAM ambiguity increases the potential for undesirable activity of the enzyme at off-target sequences harbouring high or perfect sequence identity to the PAM. Specificity of these systems remains a concern, as targeting similar sites by accident ("off-targets") will increase the likelihood of adverse events.

Existing CRISPR-Cas 9 systems generally have one or more of the following disadvantages:

a) Their size is too large to be carried inside the genome of established therapeutically-suitable viral delivery systems like adeno associated viruses (AAVs).
b) Many of them are not substantially active in non-host environments, for example in eukaryotic cells, and in particular in mammalian cells.
c) Their nuclease can catalyze DNA strand cleavage when mismatches between spacer and protospacer sequences are present, leading to undesired off target effects that would for example make them unsuitable for gene therapeutic uses or other applications requiring high precision.
d) They may trigger an immune response that can limit their use for in vivo applications in mammals.
e) They require complex and/or long PAMs that restrict target selection for the DNA targeting segments.
f) They exhibit poor expression from plasmid or viral vectors.

SUMMARY OF THE INVENTION

The present invention relates to improved Cas nucleases that at least can have increased specificity compared to certain wildtype enzymes, as well as having a relatively small size maintaining a small size.

In one aspect, provided herein is a M-SmallCas9 polypeptide selected from the group: M-SauCas9_X according to SEQ ID NO. 1, M-SluCas9_X according to SEQ ID NO. 2, M-SpaCas9_X according to SEQ ID NO. 3, M-ShyCas9_X according to SEQ ID NO. 4, M-SmiCas9_X according to SEQ ID NO. 5, MGib11SpaCas9-3-E410A, according to SEQ ID NO. 8, MGib11Spa-1-M417L according to SEQ ID NO. 133, or any polypeptide sequence that is at least 95% identical to any of the foregoing polypeptides.

In one aspect, provided herein is a M-SmallCas9 polypeptide selected from the group: M-SauCas9-R420A, according to SEQ ID NO. 6; M-SluCas9-R414A, according to SEQ ID NO. 7; M-Gib11SpaCas9-3-E410A, according to SEQ ID NO. 8; and M-Gib11Spa-1-M417L according to SEQ ID NO. 133, or any polypeptide sequence that is at least 95% identical to any of the foregoing polypeptides.

In another aspect, provided herein is a composition comprising: (I) a M-SmallCas9 polypeptide disclosed herein; and (II) one or more single heterologous guide RNA(s) (sgRNA) or DNA(s) that allow the generation of such one or more sgRNA(s) in situ, each sgRNA or DNA encoding an sgRNA comprising (a) an engineered DNA targeting segment that can hybridize to a target sequence in a polynucleotide locus, (b) a tracr mate sequence, and (c) a tracr RNA sequence, wherein the tracr mate sequence can hybridize to the tracr sequence, and wherein (a), (b), and (c) are arranged in a 5' to 3' orientation. In some embodiments, the engineered DNA targeting segment is directly adjacent to the PAM sequence on its 3' end or such PAM sequence is part of the DNA targeting sequence in its 3' portion.

In one aspect, provided herein is a method of targeting, editing, modifying, or manipulating a target DNA at one or more locations in a cell or in vitro, the method comprising (I) introducing a heterologous M-SmallCas9 polypeptide disclosed herein or a nucleic acid encoding a M-SmallCas9 disclosed herein into the cell or into the in vitro environment; and (II) introducing one or more single heterologous guide RNA(s) (sgRNA) or DNA(s) encoding such one or more sgRNA(s) in the cell or the in vitro environment, each sgRNA or DNA encoding the sgRNA comprising: (a) an engineered DNA targeting segment comprising an RNA and capable of hybridizing to a target sequence in a polynucleotide locus, (b) a tracr mate sequence comprised of RNA, and (c) a tracr RNA sequence comprised of RNA, wherein the tracr mate sequence hybridizes to the tracr sequence, and wherein (a), (b), and (c) are arranged in a 5' to 3' orientation; and (III) creating one or more nicks or cuts or base edits in the target DNA, wherein the M-SmallCas9 polypeptide is directed to the target DNA by the sgRNA in its processed or unprocessed form.

In one aspect, provided herein is use of a composition comprising (I) a M-SmallCas9 polypeptide disclosed herein or a nucleic acid encoding the same; and/or (II) one or more single heterologous guide RNA(s) (sgRNA) or DNA(s) suitable for the generation of such one or more sgRNA in situ, each comprising: (a) an engineered DNA targeting segment comprised of RNA and capable of hybridizing to such target sequence in a polynucleotide locus, (b) a tracr mate sequence comprised of RNA, and (c) a tracr RNA sequence comprised of RNA, wherein the tracr mate sequence hybridizes to the tracr sequence, and wherein (a), (b), and (c) are arranged in a 5' to 3' orientation; for targeting, editing, modifying, or manipulating a target DNA at one or more locations in a cell or in vitro.

In another aspect, provided herein is a cell comprising (I) a M-SmallCas9 polypeptide as disclosed herein, or a nucleic acid encoding a M-SmallCas9 polypeptide disclosed herein; and (II) one or more single heterologous guide RNA(s) (sgRNA) or DNA(s) suitable for the generation of such one or more sgRNA in situ, each comprising: (a) an engineered DNA targeting segment that can hybridizing to a target sequence in a polynucleotide locus, (b) a tracr mate sequence, and (c) a tracr RNA sequence, wherein the tracr mate sequence that can hybridize to the tracr sequence, and wherein (a), (b), and (c) are arranged in a 5' to 3' orientation.

In yet another aspect, provided herein is a kit comprising (I) a nucleic acid sequence encoding a M-SmallCas9 polypeptide as disclosed herein, wherein the nucleic acid sequence encoding the M-SmallCas9 is operably linked to a promoter; and (II) one or more single heterologous guide RNA(s) (sgRNA) or DNA(s) suitable for the generation of such one or more sgRNA in situ, each sgRNA comprising: (a) an engineered DNA targeting segment that can hybridize to a target sequence in a polynucleotide locus, (b) a tracr mate sequence, and (c) a tracr RNA sequence, wherein the tracr mate sequence can hybridize to the tracr sequence, and wherein (a), (b), and (c) are arranged in a 5' to 3' orientation.

The entire disclosure of each patent document and scientific article referred to herein, and those patent documents and scientific articles cited thereby, is expressly incorporated by reference herein for all purposes.

Additional features and advantages of the invention are more particularly described below.

BRIEF DESCRIPTION OF THE DRAWINGS

FIG. 1A shows these data for SluCas9 according to SEQ ID NO. 9; FIG. 1B shows these data for MSluCas9R414A according to SEQ ID NO. 7.

DETAILED DESCRIPTION OF THE INVENTION

Figure 1:
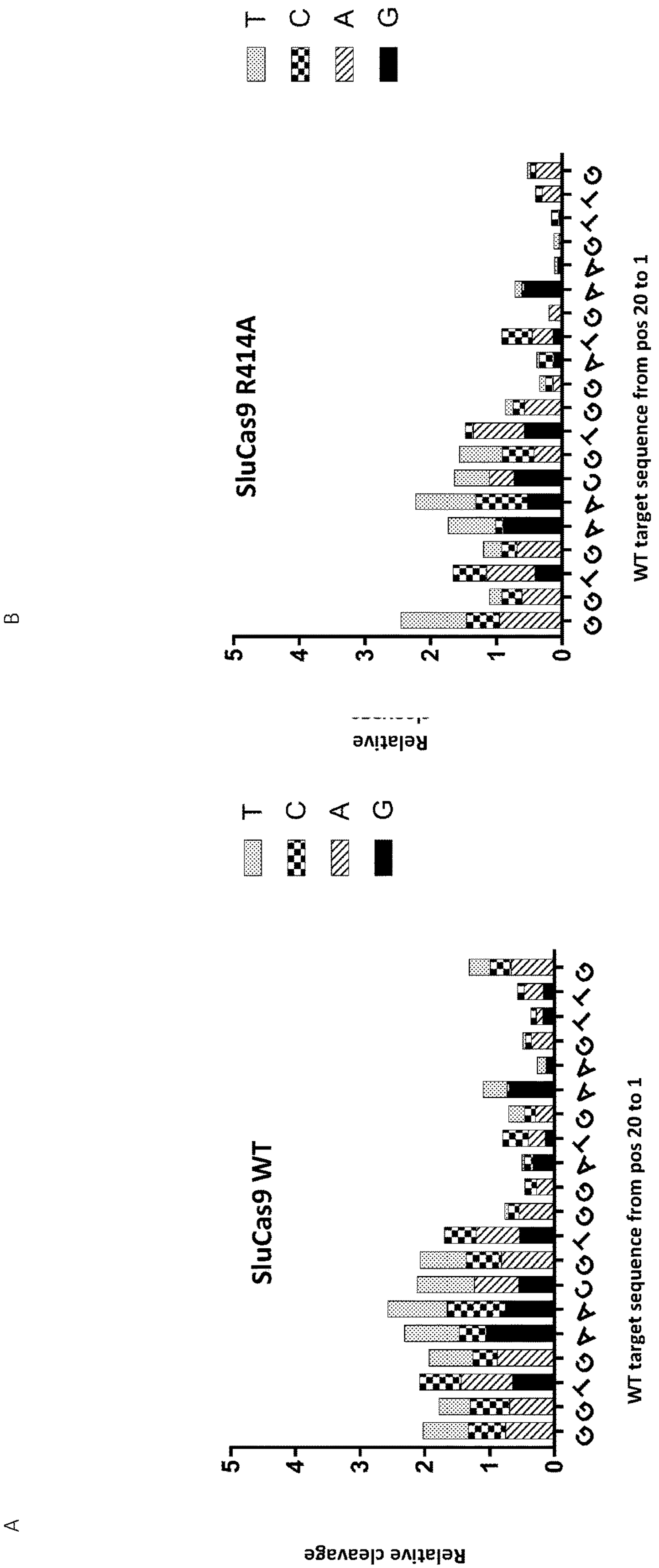
FIGS. 1A and 1B are bar graphs depicting the results of experiments testing the relative cleavage activity (y axis) of Cas nucleases as a function a) position of nucleic acid within the target sequence as shown on the x-axis and b) the respective nucleic acid residue in that position, which is visualized by differently shaded boxes that are stacked. The absence of, e.g., the box for "G" in a column means that no cleavage activity was seen in that position when the residue "G" was present.

The present application provides novel CRISPR-Cas nucleases and gene editing systems based on such nucleases that have been derived by mutagenesis of existing small CRISPR-Cas9 nucleases from the following species: *Staphylococcus aureus, Staphylococcus lugdunensis, Staphylococcus pasteuri, Staphylococcus hyicus*, and *Staphylococcus microti*. These nucleases exhibit advantages compared to existing CRISPR-Cas systems, in particular, advantages compared to parent nucleases from which they are derived. The novel nucleases are referred to herein as M-Small Cas nucleases (or M-SmallCas9 nucleases). Examples of improved activities of an M-Small Cas can include higher activity in prokaryotic, eukaryotic, and/or in vitro environments, or when expressed from a DNA plasmid in eukaryotic environments, such as, e.g., a human host cell. In particular, they exhibit improved fidelity over existing CRISPR Cas9 systems combined with favorable enzyme sizes.

The novel CRISPR-Cas nucleases according to the invention are collectively referred to as M-Small Cas (or M-Small Cas9) and are derived from small CRISPR-Cas9 nucleases, for example, from *Staphylococcus aureus* (SauCas9), *Staphylococcus lugdunensis* (SluCas9), *Staphylococcus pasteuri* (SpaCas9), *Staphylococcus hyicus* (ShyCas9), and *Staphylococcus microti* (SmiCas9). M-Small Cas nucleases contain amino acid changes that improve their gene editing fidelity compared to their corresponding wildtype nuclease.

In general, the group of M-Small Cas nucleases include following members, which are described in Table 1:

M-SauCas_X (SEQ ID NO. 1)
M-SluCas_X (SEQ ID NO. 2)
M-SpaCas_X (SEQ ID NO. 3)
M-ShyCas_X (SEQ ID NO. 4)
M-SmiCas_X (SEQ ID NO. 5). Any variant of an M-SluCas_X can alternatively have a serine in position 737 of SEQ ID NOs 2, 7, or 9.

TABLE 1

| M-SmallCas9 | SEQ ID NO. | Positions with altered possible amino acids (X in the sequence listing of the respective SEQ ID NO.) whereas the first amino acid also represents the amino acid in the wildtype enzyme | | | | | | Combination excluded from the definition |
|---|---|---|---|---|---|---|---|---|
| M-SauCas9 | 1 | 406 E, G, S, T, A, D | 412 D, G, S, T, A, E | 416 A, G, S, T, D, E | 420 R, A, G, S, T, D, E | — | — | 406 E, and 412 D, and 416 A, and 420 R |
| M-SluCas9 | 2 | 408 E, G, S, T, A, D | 414 R, G, S, T, A, D, E | 418 E, G, S, T, A, D | 422 H, A, G, S, T, D, E | 239 C, S, A | 401 C, S, A | 408 E, and 414 R, and 418 E, and 422 H, and 239 C, and 401 C |
| M-SpaCas9 | 3 | 408 E, G, S, T, A, D | 414 R, G, S, T, A, D, E | 418 E, G, S, T, A, D | 422 Y, A, G, S, T, D, E | 239 C, S, A | 401 C, S, A | 408 E, and 414 R, and 418 E, and 422 Y, and 239 C, and 401 C |
| M-ShyCas9 | 4 | 408 D, G, S, T, A, E | 414 L, G, S, T, A, D, E | 418 E, G, S, T, A, D | 422 Y, A, G, S, T, D, E | 239 C, S, A | 401 C, S, A | 408 D, and 414 L, and 418 E, and 422 K, and 239 C, and 401 C |
| M-SmiCas9 | 5 | 410 E, G, S, T, A, D | 416 M, G, S, T, A, D, E, L | 420 E, G, S, T, A, D | 424 Y, A, G, S, T, D, E | 241 C, S, A | 403 C, S, A | 410 E, and 416 M, and 420 E, and 424 Y, and 241 C, and 403 C |

Examples of M-Small Cas are listed in Table 2:

TABLE 2

| M-SmallCas9 | SEQ ID NO. | Positions with altered possible amino acids (X in the sequence listing of the respective SEQ ID NO.) whereas the first amino acid also represents the amino acid in the wildtype enzyme | | | | | | Combination excluded M-SmallCas9 |
|---|---|---|---|---|---|---|---|---|
| M-SauCas9 | 1 | 406 E, G, S, T, A | 412 D, G, S, T, A | 416 A, G, S, T | 420 R, A, G, S, T | — | — | 406 E, and 412 D, and 416 A, and 420 R |
| M-SluCas9 | 2 | 408 E, G, S, T, A | 414 R, G, S, T, A | 418 E, G, S, T, A | 422 H, A, G, S, T | 239 C, S, A | 401 C, S, A | 408 E, and 414 R, and 418 E, and 422 H, and 239 C, and 401 C |
| M-SpaCas9 | 3 | 408 E, G, S, T, A | 414 R, G, S, T, A, | 418 E, G, S, T, | 422 Y, A, G, S, T | 239 C, S, A | 401 C, S, A | 408 E, and 414 R, and 418 E, and 422 Y, and 239 C, and 401 C |
| M-ShyCas9 | 4 | 408 D, G, S, T, A | 414 L, G, S, T, A | 418 E, G, S, T, A | 422 K, A, G, S, T | 239 C, S, A | 401 C, S, A | 408 D, and 414 L, and 418 E, and 422 K, and 239 C, and 401 C |
| M-SmiCas9 | 5 | 410 E, G, S, T, A | 416 M, G, S, T, A, D, L | 420 E, G, S, T, A | 424 Y, A, G, S, T | 241 C, S, A | 403 C, S, A | 410 E, and 416 M, and 420 E, and 424 Y, and 241 C, and 403 C |

Additional examples of M-SmallCas9 are:

M-SauCas9-R420A, according to SEQ ID NO. 6;

M-SluCas9-R414A, according to SEQ ID NO. 7; and in addition the following proteins:

MGib11SpaCas9-3-E410A, according to SEQ ID NO. 8

MGib11Spa-1-M417L according to SEQ ID NO. 133.

Yet another embodiment according to the invention are the following variants of M-SmallCas9:

(I) variants of at least 95%, e.g., at least 99%, at least 99.5%, at least 99.9%, at least 99.95% amino acid identity to the sequences according to:
  a. any of SEQ ID NOs: 1, 2, 3, 4, and 5 over their entire length, but sparing out those amino acid positions that listed in Table 1 for the respective SEQ ID NO; as well as
  b. SEQ ID NOs: 6, 7, 8, and 133 over their entire length but with the provision that SEQ ID NO. 6 has an alanine in position 420, SEQ ID NO. 7, has an alanine in position 414, SEQ ID NO. 8 has an alanine in position 414, and SEQ ID NO. 133 has a leucine position 417.

(II) variants according to (I) that contain additional components as e.g. nuclear localization signals to obtain appropriate activity of the M-SmallCas9 CRISPR system not only in a cell-free reaction or in prokaryotic cells but also in eukaryotic cellular environments including in live organisms like plants or animals;

(III) codon optimized variants of the corresponding polynucleotide sequences encoding for M-SmallCas9 and the variants according to (I) and (II).

If not otherwise specified the term M-SmallCas9 comprises all of the variants specified under (I), (II), (III).

In some embodiments, a M-SmallCas9 polypeptide exhibits at least 95% amino acid identity, e.g., at least 99%, at least 99.5%, at least 99.9%, at least 99.95%, or 100% to any of SEQ ID NOs: 1, 2, 3, 4, 5, 6, 7, 8, or 133 over their entire length, excluding those amino acid positions that are listed in Table 1 for the respective SEQ ID NO.

Yet another embodiment according to the invention are the following variants of M-SmallCas9:

(IV) variants of at least 95%, at least 96%, at least 97%, at least 98%, at least 99%, at least 99.5%, at least 99.9%, or at least 99.95% amino acid identity to the sequences according to:
  a. any of SEQ ID NOs: 1, 2, 3, 4, and 5 over their entire length, but sparing out those amino acid positions that listed in Table 1 for the respective SEQ ID NO; as well as
  b. SEQ ID NOs: 6, 7, 8, and 133 over their entire length but with the provision that SEQ ID NO. 6 has an alanine in position 420, SEQ ID NO. 7, has an alanine in position 414, SEQ ID NO. 8 has an alanine in position 414, and SEQ ID NO. 133 has a leucine position 417.

(V) variants according to (I) that contain additional components as e.g. nuclear localization signals to obtain appropriate activity of the M-SmallCas9 CRISPR system not only in a cell-free reaction or in prokaryotic cells but also in eukaryotic cellular environments including in live organisms like plants or animals;

(VI) codon optimized variants of the corresponding polynucleotide sequences encoding for M-SmallCas9 and the variants according to (I) and (II).

If not otherwise specified the term M-SmallCas9 comprises all of the variants specified under (1), (II), (III).

In some embodiments, a M-SmallCas9 polypeptide exhibits least 95%, at least 96%, at least 97%, at least 98%, at least 99%, at least 99.5%, at least 99.9%, or 100% to any of SEQ ID NOs: 1, 2, 3, 4, 5, 6, 7, 8, or 133 over their entire length, excluding those amino acid positions that listed in Table 1 for the respective SEQ ID NO.

CRISPR-Cas System Based on M-SmallCas9

One embodiment according to the invention represents compositions comprising:

(a) a M-SmallCas9 polypeptide or a polynucleotide encoding such M-SmallCas9;

(b) a single heterologous guide RNA (sgRNA) or a DNA that allows the generation of such sgRNA in situ, which comprise(s):
  i. an engineered DNA targeting segment comprised of RNA and capable of hybridizing to a target sequence in a polynucleotide locus,
  ii. a tracr mate sequence comprised of RNA, and
  iii. a tracr RNA sequence comprised of RNA, wherein the tracr mate sequence hybridizes to the tracr sequence, and wherein (i), (ii), and (iii) are arranged in a 5' to 3' orientation.

Within a sgRNA a tracr mate sequence and a tracr sequence is generally connected by a suitable loop sequence and form a stem-loop structure.

PAM Sequences for Use in CRISPR-Cas9 Systems Including M-SmallCas9

The PAM sequences that are generally used according to the invention are listed in Table 3.

TABLE 3

Suitable PAM Sequences for the corresponding M-SmallCas9 endonucleases

| M-SmallCas9 | PAM Sequence (N being any of A, T, C, G) |
|---|---|
| M-SauCas9 | "NNGRR(T), with R being A or G" |
| M-SluCas9 | "NNGG" |
| M-SpaCas9 | "NNGG" |
| M-ShyCas9 | "NNARVM" PAM (where R = A or G; V = A, C or G; M = A or C), for example, "NNAAAA" |
| M-SmiCas9 | "NNGG" |

In some embodiments, the polynucleotide encoding M-SmallCas9 and the sgRNAs contain a suitable promoter for the expression in a cellular or in vitro environment and/or a suitable nuclear localization signal.

Another embodiment according to the invention represents methods of targeting, editing, modifying, or manipulating a target DNA at one or more locations in a cell or in vitro, comprising the steps:

(a) Introducing a heterologous M-SmallCas9 polypeptide or a nucleic acid encoding same protein into a cell or into an in vitro environment; and (b) Introducing a single heterologous guide RNA (sgRNA) or a DNA suitable for the generation of such sgRNA in situ which comprise(s):
  i. an engineered DNA targeting segment comprised of RNA and capable of hybridizing to a target sequence in a polynucleotide locus,
  ii. a tracr mate sequence comprised of RNA, and
  iii. a tracr RNA sequence comprised of RNA, wherein the tracr mate sequence can hybridize to the tracr sequence, and wherein (i), (ii), and (iii) are arranged in a 5' to 3' orientation;

(c) creating one or more cuts, nicks or edits in the target DNA, wherein the M-SmallCas9 polypeptide is directed to the target DNA by the gRNA in its processed or unprocessed form.

Another embodiment according to the invention is the use of a compositions comprising (a) a M-SmallCas9 polypeptide or a polynucleotide encoding such M-SmallCas9;
(b) single heterologous guide RNA (sgRNA) or a DNA suitable for the generation of such sgRNA in situ which comprise(s):
  i. an engineered DNA targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence hybridizes to the tracr sequence, and wherein (i), (ii), and (iii) are arranged in a 5' to 3' orientation;

for targeting, editing, modifying, or manipulating a target DNA at one or more locations in a cell or in vitro.

Another embodiment according to the invention is a cell ex vivo or in vitro comprising:

(a) a heterologous M-SmallCas9 polypeptide or a nucleic acid encoding the same
(b) a single heterologous guide RNA (sgRNA) or a DNA suitable for the generation of such sgRNA in situ which comprise(s):
  i. an engineered DNA targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence hybridizes to the tracr sequence, and wherein (i), (ii), and (iii) are arranged in a 5' to 3' orientation;

or such cell whose genome has been targeting, editing, modifying, or manipulating using the above (a) and (b).

Additional embodiments according to the invention are kits comprising:

(a) a nucleic acid sequence encoding M-SmallCas9, wherein the nucleic acid sequence encoding M-SmallCas9 is operably linked to a promoter or a ribosome binding site;
(b) single heterologous guide RNA (sgRNA) or a DNA suitable for the generation of such sgRNA in situ which comprise(s):
  i. an engineered DNA targeting segment comprised of RNA and capable of hybridizing to such target sequence in a polynucleotide locus,
  ii. a tracr mate sequence comprised of RNA, and
  iii. a tracr RNA sequence comprised of RNA, wherein the tracr mate sequence hybridizes to the tracr sequence, and wherein (i), (ii), and (iii) are arranged in a 5' to 3' orientation.

or (a) M-SmallCas9 protein;
(b) one or more single heterologous guide RNAs (sgRNAs) each of which comprise(s):
  iv. an engineered DNA targeting segment comprised of RNA and capable of hybridizing to such target sequence in a polynucleotide locus,
  v. a tracr mate sequence comprised of RNA, and
  vi. a tracr RNA sequence comprised of RNA, wherein the tracr mate sequence hybridizes to the tracr sequence, and wherein (i), (ii), and (iii) are arranged in a 5' to 3' orientation.

Yet another embodiment according to the invention comprises compositions and methods for targeting, editing, modifying, or manipulating one or more target DNA(s) at one or more locations in a cell or in vitro comprising:

(a) M-SmallCas9
(b) guide RNA (gRNA) or a DNA suitable for the generation of such gRNA in situ which comprise(s):
  i. an engineered DNA targeting segment comprised of RNA and capable of hybridizing to such target sequence in a polynucleotide locus,
  ii. a tracr RNA sequence comprised of RNA;

wherein (i) and (ii) are one a single RNA molecule and (iii) is on a separate RNA molecule.

Multiplexing

In another aspect, provided herein is a method for editing or modifying DNA at multiple locations in a cell, the method consisting essentially of: i) introducing a M-SmallCas9 polypeptide or a nucleic acid encoding a M-SmallCas9 polypeptide into the cell; and ii) introducing a single heterologous nucleic acid comprising two or more pre-CRISPR RNAs (pre-crRNAs) either as RNA or encoded as DNA and under the control of one promoter into the cell, each pre-crRNA comprising a repeat-spacer array or repeat-spacer, wherein the spacer comprises a nucleic acid sequence that is complementary to a target sequence in the DNA and the repeat comprises a stem-loop structure, wherein the M-SmallCas9 polypeptide cleaves the two or more pre-crRNAs upstream of the stem-loop structure to generate two or more intermediate crRNAs, wherein the two or more intermediate crRNAs are processed into two or more mature crRNAs, and wherein each two or more mature crRNAs guides the M-SmallCas9 polypeptide to effect two or more double-strand breaks (DSBs) into the DNA. For example, one advantage of M-SmallCas9 is that it is possible to introduce only one pre-crRNA which comprises several repeat-spacer units, which upon introduction, is processed by M-SmallCas9 it into active repeat-spacer units targeting several different sequences on the DNA.

In another aspect, provided herein is a method for editing or modifying DNA at multiple locations in a cell consisting essentially of: i) introducing a form of M-SmallCas9 with reduced endoribonuclease activity, as a polypeptide or a nucleic acid encoding a M-SmallCas9 polypeptide into the cell; and ii) introducing a single heterologous nucleic acid comprising two or more pre-CRISPR RNAs (pre-crRNAs), intermediate crRNAs or mature crRNAs either as RNA or encoded as DNA and under the control of one or more promoters, each crRNA comprising a repeat-spacer array, wherein the spacer comprises a nucleic acid sequence that is complementary to a target sequence in the DNA and the repeat comprises a stem-loop structure, wherein the M-SmallCas9 polypeptide binds to one or more regions of the single heterologous RNA with reduced or absent endoribonuclease activity and with intact endonuclease activity as directed by one or more spacer sequences in the single heterologous nucleic acid.

In some embodiments the pre-crRNA sequences in the single heterologous nucleic acid are joined together in specific locations, orientations, sequences or with specific chemical linkages to direct or differentially modulate the endonuclease activity of M-SmallCas9 at each of the sites specified by the different crRNA sequences.

In another aspect, provided herein is an example of a general method for editing or modifying the structure or function of DNA at multiple locations in a cell consisting essentially of: i) introducing an RNA-guided endonuclease, such as M-SmallCas9, as a polypeptide or a nucleic acid encoding the RNA-guided endonuclease into the cell; and ii) introducing a single heterologous nucleic acid comprising or encoding two or more guide RNAs, either as RNA or encoded as DNA and under the control of one or more promoters, wherein the activity or function of the RNA-guided endonuclease is directed by the guide RNA sequences in the single heterologous nucleic acid.

Definitions

The terms "polynucleotide," "nucleic acid," and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids/triple helices, or a polymer including purine and pyrimidine bases or other natural, chemically or biochemically modified, non-natural, or derivatized nucleotide bases.

"Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as "oligomers" or "oligos" and may be isolated from genes, or chemically synthesized by methods known in the art. The terms "polynucleotide" and "nucleic acid" should be understood to include, as applicable to the embodiments being described, single-stranded (such as sense or antisense) and double-stranded polynucleotides.

Genomic DNA" refers to the DNA of a genome of an organism including, but not limited to, the DNA of the genome of a bacterium, fungus, archaeon, protist, virus, plant or animal.

The term "manipulating" DNA encompasses binding, nicking one strand, or cleaving, e.g. cutting both strands of the DNA; or encompasses modifying or editing the DNA or a polypeptide associated with the DNA. Manipulating DNA can silence, activate, or modulate (either increase or decrease) the expression of an RNA or polypeptide encoded by the DNA, or prevent or enhance the binding of a polypeptide to DNA.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. As is known in the art, a stem-loop structure does not require exact base-pairing. Thus, the stem may include one or more base mismatches. Alternatively, the base-pairing may be exact, e.g., not include any mismatches.

By "hybridizable" or "complementary" or "substantially complementary" it is meant that a nucleic acid (e.g. RNA or DNA) includes a sequence of nucleotides that enables it to non-covalently bind, e.g., form Watson-Crick base pairs and/or G/U base pairs, "anneal", or "hybridize," to another nucleic acid in a sequence-specific, antiparallel, manner (e.g., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In addition, it is also known in the art that for hybridization between two RNA molecules (e.g. dsRNA), guanine (G) base pairs with uracil (U). For example, G/U base-pairing is partially responsible for the degeneracy (e.g., redundancy) of the genetic code in the context of tRNA anti-codon base-pairing with codons in mRNA. In the context of this disclosure, a guanine (G) of a protein-binding segment (dsRNA duplex) of a guide RNA molecule is considered complementary to a uracil (U), and vice versa. As such, when a G/U base-pair can be made at a given nucleotide position a protein-binding segment (dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches becomes important (see Sambrook et al., supra, 11.7-11.8). Generally, the length for a hybridizable nucleic acid is at least 10 nucleotides. Illustrative minimum lengths for a hybridizable nucleic acid are: at least 15 nucleotides; at least 20 nucleotides; at least 22 nucleotides; at least 25 nucleotides; and at least 30 nucleotides). Furthermore, the skilled artisan will recognize that the temperature and wash solution salt concentration maybe adjusted as necessary according to factors such as length of the region of complementation and the degree of complementation.

It is understood in the art that the sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g. a loop structure or hairpin structure). A polynucleotide can include at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining non complementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul et al., J. Mol. Biol. 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math. 1981 (2) 482-489).

The terms "peptide", "polypeptide", and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide) refers to a non-covalent interaction between macromolecules (e.g. between a protein and a nucleic acid). While in a state of non-covalent interaction, the macromolecules are said to be "associated" or "interacting" or "binding" (e.g. when a molecule X is said to interact with a molecule Y, it is meant the molecule X binds to molecule Y in a non-covalent manner). Not all components of a binding interaction need be sequence-specific (e.g. contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein-binding protein). In the case of a protein domain-binding protein, it can bind to itself (to form homo-dimers, homo-trimers, etc.) and/or it can bind to one or more molecules of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g. BLAST, T-COFFEE, MUSCLE, MAFFT, etc.), available over the world-wide-web at sites including ncbi.nlm.nili.gov/BLAST, ebi.ac.uk/Tools/msa/tcoffee, ebi.Ac.Uk/Tools/msa/muscle, mafft.cbrc/alignment/software. See, e.g. Altschul et al. (1990), J. Mol. Biol. 215:403-10. In some embodiments of the disclosure, sequence alignments standard in the art are used according to the disclosure to determine amino acid residues in M-SmallCas9 polypeptide or variant thereof that "correspond to" amino acid residues in another Cas9 endonuclease. The amino acid residues of M-SmallCas9 polypeptides or variants thereof that correspond to amino acid residues of other Cas9 endonucleases appear at the same position in alignments of the sequences.

A DNA sequence that "encodes" a particular RNA is a DNA nucleic acid sequence that is transcribed into the RNA. A polydeoxyribonucleotide may encode an RNA (mRNA) that is translated into protein, or a polydeoxyribonucleotide may encode an RNA that is not translated into protein (e.g. tRNA, rRNA, or a guide RNA; also called "non-coding" RNA or "ncRNA"). A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will generally be located at 3' of the coding sequence.

As used herein, a "promoter sequence" or "promoter" is a DNA regulatory region capable of binding RNA polymerase and initiating transcription of a downstream (3' direction) coding or non-coding sequence. As used herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAAT" boxes. Various promoters, including inducible promoters, may be used to drive the various vectors of the present disclosure. A promoter can be a constitutively active promoter (e.g., a promoter that is constitutively in an active "ON" state), it may be an inducible promoter (e.g., a promoter whose state, active/"ON" or inactive/"OFF", is controlled by an external stimulus, e.g. the presence of a particular temperature, compound, or protein.), it may be a spatially restricted promoter (e.g., transcriptional control element, enhancer, etc.) (e.g. tissue specific promoter, cell type specific promoter, etc.), and it may be a temporally restricted promoter (e.g., the promoter is in the "ON" state or "OFF" state during specific stages of embryonic development or during specific stages of a biological process, e.g. hair follicle cycle in mice). Suitable promoters can be derived from viruses and can therefore be referred to as viral promoters, or they can be derived from any organism, including prokaryotic or eukaryotic organisms. Suitable promoters can be used to drive expression by any RNA polymerase (e.g. pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g. Xia et al., Nucleic Acids Res. 2003 Sep. 1; 31 (17)), a human H1 promoter (H1), and the like. Examples of inducible promoters include, but are not limited to T7 RNA polymerase promoter, T3 RNA polymerase promoter, isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g. T7 RNA polymerase; an estrogen receptor; an estrogen receptor fusion; etc.

In some embodiments, the promoter is a spatially restricted promoter (e.g., cell type specific promoter, tissue specific promoter, etc.) such that in a multi-cellular organism, the promoter is active (e.g., "ON") in a subset of specific cells. Spatially restricted promoters may also be referred to as enhancers, transcriptional control elements, control sequences, etc. Any suitable spatially restricted promoter may be used and the choice of suitable promoter (e.g. a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a site-specific modifying enzyme in a wide variety of different tissues and cell types, depending on the organism. Some spatially restricted promoters are also temporally restricted such that the promoter is in the "ON" state or "OFF" state during specific stages of embryonic development or during specific stages of a biological process (e.g. hair follicle cycle in mice). For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g. EMBL HSEN02, X51956); an aromatic amino acid decarboxylase (AADC) promoter; a neurofilament promoter (see, e.g. GenBank HUMNFL, L04147); a synapsin promoter (see, e.g. GenBank HUMSYNIB, M55301); a thy-1 promoter (see, e.g. Chen et al. (1987) Cell 51:7-19; and Llewellyn, et al. (2010) Nat. Med. 16 (10): 1161-1166); a serotonin receptor promoter (see, e.g. GenBank S62283); a tyrosine hydroxylase promoter (TH) (see, e.g. Oh et al. (2009) Gene Ther. 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g. Radovick et al. (1991) Proc. Natl. Acad. Sci. USA 88:3402-3406); an L7 promoter (see, e.g. Oberdick et al. (1990) Science 248:223-226); a DNMT promoter (see, e.g. Bartge et al. (1988) Proc. Natl. Acad. Sci. USA 85:3648-3652); an enkephalin promoter (see, e.g. Comb et al. (1988) EMBO J. 17:3793-3805); a myelin basic protein (MBP) promoter; a Ca2+-calmodulin-dependent protein kinase 11-alpha (CamKIM) promoter (see, e.g. Mayford et al. (1996) Proc. Natl. Acad. Sci. USA 93:13250; and Casanova et al. (2001) Genesis 31:37); a CMV enhancer/platelet-derived growth factor-p promoter (see, e.g. Liu et al. (2004) Gene Therapy 11:52-60); and the like.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g. guide RNA) or a coding sequence (e.g. M-SmallCas9 polypeptide or variant thereof) and/or regulate translation of an encoded polypeptide.

The term "naturally-occurring" or "unmodified" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is naturally occurring.

The term "chimeric" as used herein as applied to a nucleic acid or polypeptide refers to one entity that is composed of structures derived from different sources. For example, where "chimeric" is used in the context of a chimeric polypeptide (e.g. a chimeric M-SmallCas9 protein), the chimeric polypeptide includes amino acid sequences that are derived from different polypeptides. A chimeric polypeptide may include either modified or naturally-occurring polypeptide sequences (e.g. a first amino acid sequence from a modified or unmodified M-SmallCas9 protein; and a second amino acid sequence other than the M-SmallCas9 protein). Similarly, "chimeric" in the context of a polynucleotide encoding a chimeric polypeptide includes nucleotide sequences derived from different coding regions (e.g. a first nucleotide sequence encoding a modified or unmodified M-SmallCas9 protein; and a second nucleotide sequence encoding a polypeptide other than a M-SmallCas9 protein).

The term "chimeric polypeptide" refers to a polypeptide which is not naturally occurring, e.g. is made by the artificial combination (e.g., "fusion") of two or more otherwise separated segments of amino sequence through human intervention. A polypeptide that includes a chimeric amino acid sequence is a chimeric polypeptide. Some chimeric polypeptides can be referred to as "fusion variants."

"Heterologous," as used herein, means a nucleotide or peptide that is not found in the native nucleic acid or protein, respectively. A M-SmallCas9 fusion protein described herein may comprise the RNA-binding domain of the M-SmallCas9 polypeptide (or a variant thereof) fused to a heterologous polypeptide sequence (e.g., a polypeptide sequence from a protein other than M-SmallCas9). The heterologous polypeptide may exhibit an activity (e.g. enzymatic activity) that will also be exhibited by the M-SmallCas9 fusion protein (e.g. methyltransferase activity, acetyltransferase activity, kinase activity, ubiquitinating activity, etc.). A heterologous nucleic acid may be linked to a naturally-occurring nucleic acid (or a variant thereof) (e.g. by genetic engineering) to generate a fusion polynucleotide encoding a fusion polypeptide. As another example, in a fusion variant M-SmallCas9 polypeptide, a variant M-SmallCas9 polypeptide may be fused to a heterologous polypeptide (e.g., a polypeptide other than M-SmallCas9), which exhibits an activity that will also be exhibited by the fusion variant M-SmallCas9 polypeptide. A heterologous nucleic acid may be linked to a variant M-SmallCas9 polypeptide (e.g. by genetic engineering) to generate a polynucleotide encoding a fusion variant M-SmallCas9 polypeptide. "Heterologous," as used herein, additionally means a nucleotide or polypeptide in a cell that is not its native cell.

The term "cognate" refers to two biomolecules that normally interact or co-exist in nature.

"Recombinant," as used herein, means that a particular nucleic acid (DNA or RNA) or vector is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). In addition or alternatively, DNA sequences encoding RNA (e.g. guide RNA) that is not translated may also be considered recombinant. Thus, e.g. the term "recombinant" nucleic acid refers to one which is not naturally occurring, e.g. is made by the artificial combination of two otherwise separated segments of sequence through human intervention. This artificial combination is often accomplished by either chemical synthesis means, or by the artificial manipulation of isolated segments of nucleic acids, e.g. by genetic engineering techniques. Such is generally done to replace a codon with a codon encoding the same amino acid, a conservative amino acid, or a non-conservative amino acid. In addition or alternatively, it is performed to join together nuclei acid segments of desired functions to generate a desired combination of functions. This artificial combination is often accomplished by either chemical synthesis means, or by the artificial manipulation of isolated segments of nucleic acids, e.g. by genetic engineering techniques. When a recombinant polynucleotide encodes a polypeptide, the sequence of the encoded polypeptide can be naturally occurring ("wild type") or can be a variant (e.g. a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g. a variant, a mutant, etc.). Thus, a "recombinant" polypeptide is the result of human intervention, but may be a naturally occurring amino acid sequence. The term "non-naturally occurring" includes molecules that are markedly different from their naturally occurring counterparts, including chemically modified or mutated molecules.

A "vector" or "expression vector" is a replicon, such as plasmid, phage, virus, or cosmid, to which another DNA segment, e.g., an "insert", may be attached so as to bring about the replication of the attached segment in a cell.

An "expression cassette" includes a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression. The terms "recombinant expression vector," or "DNA construct" are used interchangeably herein to refer to a DNA molecule comprising a vector and at least one insert. Recombinant expression vectors are generally generated for the purpose of expressing and/or propagating the insert(s), or for the construction of other recombinant nucleotide sequences. The nucleic acid(s) may or may not be operably linked to a promoter sequence and may or may not be operably linked to DNA regulatory sequences.

The term "operably linked", as used herein, denotes a physical or functional linkage between two or more elements, e.g., polypeptide sequences or polynucleotide sequences, which permits them to operate in their intended fashion. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell.

In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that include a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include but are not limited to, e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al., Adv Drug Deliv Rev. 2012 Sep. 13. pp: S0169-409X (12) 00283-9. doi:10.1016/j.addr.2012.09.023), and the like.

A "host cell," as used herein, denotes an in vivo or in vitro eukaryotic cell, a prokaryotic cell (e.g. bacterial or archaeal cell), or a cell from a multicellular organism (e.g. a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g. an expression vector. For example, a bacterial host cell is a genetically modified bacterial host cell by virtue of introduction into a suitable bacterial host cell of an exogenous nucleic acid (e.g. a plasmid or recombinant expression vector) and a eukaryotic host cell is a genetically modified eukaryotic host cell (e.g. a mammalian germ cell), by virtue of introduction into a suitable eukaryotic host cell of an exogenous nucleic acid.

A "target DNA" as used herein is a polydeoxyribonucleotide that includes a "target site" or "target sequence." The terms "target site," "target sequence," "target protospacer DNA," or "protospacer-like sequence" are used interchangeably herein to refer to a nucleic acid sequence present in a target DNA to which a DNA-targeting segment (also referred to as a "spacer") of a guide RNA will bind, provided sufficient conditions for binding exist. For example, the target site (or target sequence) 5'-GAGCATATC-31 within a target DNA is targeted by (or is bound by, or hybridizes with, or is complementary to) the RNA sequence 5'-GAUAUGCUC-3'. Suitable DNA/RNA binding conditions include physiological conditions normally present in a cell. Other suitable DNA/RNA binding conditions (e.g. conditions in a cell-free system) are known in the art; see, e.g. Sambrook, supra. The strand of the target DNA that is complementary to and hybridizes with the guide RNA is referred to as the "complementary strand" and the strand of the target DNA that is complementary to the "complementary strand" (and is therefore not complementary to the guide RNA) is referred to as the "non-complementary strand" or "non-complementary strand."

By "site-specific modifying enzyme" or "RNA-binding site-specific modifying enzyme" is meant a polypeptide that binds RNA and is targeted to a specific DNA sequence, such as a M-SmallCas9 polypeptide. A site-specific modifying enzyme as described herein is targeted to a specific DNA sequence by the RNA molecule to which it is bound. The RNA molecule includes a sequence that binds, hybridizes to, or is complementary to a target sequence within the target DNA, thus targeting the bound polypeptide to a specific location within the target DNA (the target sequence). By "cleavage" it is meant the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a site-specific modifying enzyme is used for targeted double-stranded DNA cleavage.

"Nuclease" and "endonuclease" are used interchangeably herein to mean an enzyme which possesses endonucleolytic catalytic activity for polynucleotide cleavage.

By "cleavage domain" or "active domain" or "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

The "guide sequence" or "DNA-targeting segment" or "DNA-targeting sequence" or "spacer" includes a nucleotide sequence that is complementary to a specific sequence within a target DNA (the complementary strand of the target DNA) designated the "protospacer-like" sequence herein. The protein-binding segment (or "protein-binding sequence") interacts with a site-specific modifying enzyme. When the site-specific modifying enzyme is a M-SmallCas9 or M-SmallCas9-related polypeptide (described in more detail below), site-specific cleavage of the target DNA occurs at locations determined by both (i) base pairing complementarity between the guide RNA and the target DNA; and (ii) a short motif (referred to as the protospacer adjacent motif (PAM)) in the target DNA. The protein-binding segment of a guide RNA includes, in part, two complementary stretches of nucleotides that hybridize to one another to form a double stranded RNA duplex (dsRNA duplex). In some embodiments, a nucleic acid (e.g. a guide RNA, a nucleic acid comprising a nucleotide sequence encoding a guide RNA; a nucleic acid encoding a site-specific modifying enzyme; etc.) includes a modification or sequence that provides for an additional desirable feature (e.g. modified or regulated stability; subcellular targeting; tracking, e.g. a fluorescent label; a binding site for a protein or protein complex; etc.). Non-limiting examples include: a 5' cap (e.g. a 7-methylguanylate cap (m7G)); a 3' polyadenylated tail (e.g., a 3' poly(A) tail); a riboswitch sequence (e.g. to allow for regulated stability and/or regulated accessibility by proteins and/or protein complexes); a stability control sequence; a sequence that forms a dsRNA duplex (e.g., a hairpin)); a modification or sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like); and combinations thereof.

In some embodiments, a guide RNA includes an additional segment at either the 5' or 3' end that provides for any of the features described above. For example, a suitable third segment can include a 5' cap (e.g. a 7-methylguanylate cap (m7G)); a 3' polyadenylated tail (e.g., a 3' poly(A) tail); a riboswitch sequence (e.g. to allow for regulated stability and/or regulated accessibility by proteins and protein complexes); a stability control sequence; a sequence that forms a dsRNA duplex (e.g., a hairpin)); a sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA. including transcriptional activators, transcriptional repressors, DNA methyltransferases, DNA demethylases, histone acetyltransferases, histone deacetylases, and the like); and combinations thereof.

A guide RNA and a site-specific modifying enzyme such as a M-SmallCas9 polypeptide or variant thereof may form a ribonucleoprotein complex (e.g., bind via non-covalent interactions). The guide RNA provides target specificity to the complex by comprising a nucleotide sequence that is complementary to a sequence of a target DNA. The site-specific modifying enzyme of the complex provides the endonuclease activity. In other words, the site-specific modifying enzyme is guided to a target DNA sequence (e.g. a target sequence in a chromosomal nucleic acid; a target sequence in an extrachromosomal nucleic acid, e.g. an episomal nucleic acid, a minicircle, etc.; a target sequence in a mitochondrial nucleic acid; a target sequence in a chloroplast nucleic acid; a target sequence in a plasmid; etc.) by virtue of its association with the protein-binding segment of the guide RNA. RNA aptamers are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the RNA molecule of which they are part. RNA aptamers generally include a sequence that folds into a particular structure (e.g. a hairpin), which specifically binds a particular drug (e.g. a small molecule). Binding of the drug causes a structural change in the folding of the RNA, which changes a feature of the nucleic acid of which the aptamer is a part. As non-limiting examples: (i) an activator-RNA with an aptamer may not be able to bind to the cognate targeter RNA unless the aptamer is bound by the appropriate drug; (ii) a targeter-RNA with an aptamer may not be able to bind to the cognate activator-RNA unless the aptamer is bound by the appropriate drug; and (iii) a targeter-RNA and an activator-RNA, each comprising a different aptamer that binds a different drug, may not be able to bind to each other unless both drugs are present. As illustrated by these examples, a two-molecule guide RNA can be designed to be inducible.

Examples of aptamers and riboswitches can be found, for example, in: Nakamura et al., Genes Cells. 2012 May; 17 (5): 344-64; Vavalle et al., Future Cardiol. 2012 May; 8 (3): 371-82; Citartan et al., Biosens Bioelectron. 2012 Apr. 15; 34 (1): 1-11; and Liberman et al., Wiley Interdiscip Rev RNA. 2012 May-Jun; 3 (3): 369-84; all of which are herein incorporated by reference in their entireties.

The choice of method of genetic modification is generally dependent on the type of cell being transformed and the circumstances under which the transformation is taking place (e.g. in vitro, ex vivo, or in vivo). A general discussion of these methods can be found in Ausubel, et al., Short Protocols in Molecular Biology, 3rd ed., Wiley & Sons, 1995.

Examples of aptamers and riboswitches can be found, for example, in: Nakamura et al., Genes Cells. 2012 May; 17 (5): 344-64; Vavalle et al., Future Cardiol. 2012 May; 8 (3): 371-82; Citartan et al., Biosens Bioelectron. 2012 Apr. 15; 34 (1): 1-11; and Liberman et al., Wiley Interdiscip Rev RNA. 2012 May-June; 3 (3): 369-84; all of which are herein incorporated by reference in their entirety.

The term "stem cell" is used herein to refer to a cell (e.g. plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g. mesodermal stem cells), which in turn can differentiate into cells that are further restricted (e.g. neuron progenitors), which can differentiate into end-stage cells (e.g., terminally differentiated cells, e.g. neurons. cardiomyocytes, etc.), which play a characteristic role in a certain tissue type, and may or may not retain the capacity to proliferate further. Stem cells may be characterized by both the presence of specific markers (e.g. proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g. the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g. cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282 (5391): 1145-7) whereas induced pluripotent stem cells (iPSCs) are derived from somatic cells (Takahashi et. al, Cell. 2007 Nov. 30; 131 (5): 861-72; Takahashi et. al, Nat Protoc. 2007; 2 (12): 3081-9; Yu et. al, Science. 2007 Dec. 21; 318 (5858): 1917-20. Epub 2007 Nov. 20).

Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, generally from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats. hamster, primate, etc. (Thomson et al. (1998) Science 282:1145; Thomson et al. (1995) Proc. Natl. Acad. Sci. USA 92:7844; Thomson et al. (1996) Biol. Reprod. 55:254; Shamblott et al., Proc. Natl. Acad. Sci. USA 95:13726, 1998). In culture, ESCs generally grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. Nos. 7,029,913, 5,843,780, and 6,200,806, the disclosures of which are incorporated herein by reference. Methods for proliferating hESCs in the undifferentiated form are described in WO 99/20741, WO 01/51616, and WO 03/020920. By "embryonic germ stem cell" (EGSC) or "embryonic germ cell" or "EG cell" is meant a PSC that is derived from germ cells and/or germ cell progenitors, e.g. primordial germ cells, e.g., those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98:113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (e.g., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, Fox03, GDF3, Cyp26al, TERT, and zfp42.

Examples of methods of generating and characterizing iPSCs may be found in, for example, US Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, e.g., ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis.

By "post-mitotic cell" it is meant a cell that has exited from mitosis, e.g., it is "quiescent", e.g., it is no longer undergoing divisions. This quiescent state may be temporary, e.g., reversible, or it may be permanent.

By "meiotic cell" it is meant a cell that is undergoing meiosis.

By "recombination" it is meant a process of exchange of genetic information between two polynucleotides. As used herein, "homology-directed repair (HDR)" refers to the specialized form DNA repair that takes place, for example, during repair of double-strand breaks in cells. This process requires nucleotide sequence homology, uses a "donor" molecule to template repair of a "target" molecule (e.g., the one that experienced the double-strand break), and leads to the transfer of genetic information from the donor to the target. Homology-directed repair may result in an alteration of the sequence of the target molecule (e.g. insertion, deletion, mutation), if the donor polynucleotide differs from the target molecule and part or all of the sequence of the donor polynucleotide is incorporated into the target DNA. In some embodiments, the donor polynucleotide, a portion of the donor polynucleotide, a copy of the donor polynucleotide, or a portion of a copy of the donor polynucleotide integrates into the target DNA.

By "non-homologous end joining (NHEJ) it is meant the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

The terms "treatment", 'treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, e.g., arresting its development; or (c) relieving the disease, e.g., causing regression of the disease. The therapeutic agent may be administered before, during or after the onset of disease or injury. The treatment of ongoing disease, where the treatment stabilizes or reduces the undesirable clinical symptoms of the subject, is of particular interest. Such treatment is desirably performed prior to complete loss of function in the affected tissues. The therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (1. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

The phrase "consisting essentially of" is meant herein to exclude anything that is not the specified active component or components of a system, or that is not the specified active portion or portions of a molecule.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

M-SmallCas9 Fusion Polypeptides

A M-SmallCas9 can be used to form a fusion protein having additional domains and activities compared to the M-SmallCas9 nuclease. By way of non-limiting illustration, a FokI domain can be fused to a M-SmallCas9 polypeptide or variant thereof, which can contain a catalytically active endonuclease domain, or a FokI domain can be fused to a M-SmallCas9 polypeptide or variant thereof, which has been modified to render the M-SmallCas9 endonuclease domain inactive. Other domains that can be fused to make fusion proteins with M-SmallCas9 include transcriptional modulators, epigenetic modifiers, tags and other labels or imaging agents, histones, and/or other modalities known in the art that modulate or modify the structure or activity of gene sequences.

In some embodiments, a M-SmallCas9 polypeptide or variant thereof described herein is fused to a transcriptional activator or repressor, or epigenetic modifier such as a methylase, demethylase, acetylase, or deacetylase.

In some embodiments, a M-SmallCas9 polypeptide or variant thereof described herein is fused to functional protein components for detection, inter-molecular interaction, translational activation, modification, or any other manipulation known in the art.

Exemplary M-SmallCas9 Variant Polypeptides

In some embodiments, a M-SmallCas9 polypeptide or variant thereof described herein retains a) the capability of binding to a targeted site and, optionally, b) retains its activity. In some embodiments, the activity being retained is endonuclease activity. In certain embodiments, the endonuclease activity does not require tracrRNA.

In some embodiments, the activity portion of the M-SmallCas9 polypeptide or variant thereof is modified. In some embodiments, the modification comprises an amino acid change (e.g. deletion, insertion, or substitution) that reduces or increases the nuclease activity of the M-SmallCas9 polypeptide or variant thereof. For example, in some embodiments, the modified M-SmallCas9 polypeptide or variant thereof has less than 50%, less than 40%, less than 30%, less than 20%, less than 10%, less than 5%, or less than 1% of the nuclease activity of the corresponding unmodified M-SmallCas9 polypeptide or variant thereof. In some embodiments, the modified M-SmallCas9 polypeptide or variant thereof has no substantial nuclease activity. In some embodiments, it may have 50%, 2-fold, 4-fold or up to over 10-fold more nuclease activity.

In some embodiments, the activity portion of the M-SmallCas9 polypeptide or variant thereof comprises a heterologous polypeptide that has DNA-modifying activity and/or transcription factor activity and/or DNA-associated polypeptide-modifying activity. In some embodiments, a heterologous polypeptide replaces a portion of the M-SmallCas9 polypeptide or variant thereof that provides nuclease activity. In some embodiments, the M-SmallCas9 polypeptide or variant thereof comprises both a portion of the M-SmallCas9 polypeptide or variant thereof that normally provides nuclease activity (and that portion can be fully active or can instead be modified to have less than 100% of the corresponding unmodified activity) and a heterologous polypeptide. In other words, in some embodiments, a M-SmallCas9 polypeptide or variant thereof can be a fusion polypeptide comprising both the portion of the M-SmallCas9 polypeptide or variant thereof that normally provides nuclease activity and the heterologous polypeptide.

For example, in a M-SmallCas9 fusion protein, a M-SmallCas9 polypeptide or variant thereof may be fused to a heterologous polypeptide sequence (e.g., a polypeptide sequence from a protein other than M-SmallCas9). The heterologous polypeptide sequence may exhibit an activity (e.g. enzymatic activity) that will also be exhibited by the M-SmallCas9 fusion protein (e.g. methyltransferase activity, acetyltransferase activity, kinase activity, ubiquitinating activity, etc.). A heterologous nucleic acid sequence may be linked to another nucleic acid sequence (e.g. by genetic engineering) to generate a fusion nucleotide sequence encoding a fusion polypeptide. In some embodiments, a M-SmallCas9 fusion polypeptide is generated by fusing a M-SmallCas9 polypeptide or variant thereof with a heterologous sequence that provides for subcellular localization (e.g. a nuclear localization signal (NLS) for targeting to the nucleus; a mitochondrial localization signal for targeting to the mitochondria; a chloroplast localization signal for targeting to a chloroplast: an ER retention signal; and the like). In some embodiments, the heterologous sequence can provide a tag for ease of tracking or purification (e.g. a fluorescent protein, e.g. green fluorescent protein (GFP), YFP, RFP, CFP, mCherry, tdTomato, and the like; a HIS tag, e.g. a 6×His tag; a hemagglutinin (HA) tag; a FLAG tag; a Myc tag; and the like). In some embodiments, the heterologous sequence can provide for increased or decreased stability. In some embodiments, the heterologous sequence can provide a binding domain (e.g. to provide the ability of a M-SmallCas9 fusion polypeptide to bind to another protein of interest, e.g. a DNA or histone modifying protein, a transcription factor or transcription repressor, a recruiting protein, etc.) or to a nucleotide of interest (e.g., an aptamer or target site of a nucleotide binding protein).

In some embodiments, according to any of the M-SmallCas9 polypeptides variants described herein, the M-SmallCas9 polypeptide variant has reduced endodeoxyribonuclease activity. For example, a M-SmallCas9 polypeptide variant suitable for use in a transcription modulation method of the present disclosure exhibits less than about 20%, less than about 15%, less than about 10%, less than about 5%, less than about 1%, or less than about 0.1%, of the endodeoxyribonuclease activity of an unmodified M-SmallCas9 polypeptide.

In some embodiments, the variant M-SmallCas9 polypeptide has substantially no detectable endodeoxyribonuclease activity (dM-SmallCas9). In some embodiments when a M-SmallCas9 polypeptide variant has reduced catalytic activity, the polypeptide can still bind to target DNA in a site-specific manner (because it is still guided to a target DNA sequence by a guide RNA) as long as it retains the ability to interact with the guide RNA. In some embodiments, the variant M-SmallCas9 polypeptide is a nickase that can cleave the complementary strand of the target DNA but has reduced ability to cleave the non-complementary strand of the target DNA In some embodiments, the variant M-SmallCas9 polypeptide in a nickase that can cleave the non-complementary strand of the target DNA but has reduced ability to cleave the complementary strand of the target DNA.

In some embodiments, the variant M-SmallCas9 polypeptide has a reduced ability to cleave both the complementary and the non-complementary strands of the target DNA. For example, alanine substitutions are contemplated.

In some embodiments, the variant M-SmallCas9 polypeptide is a fusion polypeptide (a "variant M-SmallCas9 fusion polypeptide"), e.g., a fusion polypeptide comprising: i) a variant M-SmallCas9 polypeptide; and ii) a covalently linked heterologous polypeptide (also referred to as a "fusion partner").

The heterologous polypeptide may exhibit an activity (e.g. enzymatic activity) that will also be exhibited by the variant M-SmallCas9 fusion polypeptide (e.g. methyltransferase activity, acetyltransferase activity, kinase activity, ubiquitinating activity, etc.). A heterologous nucleic acid sequence may be linked to another nucleic acid sequence (e.g. by genetic engineering) to generate a fusion nucleotide sequence encoding a fusion polypeptide. In some embodiments, a variant M-SmallCas9 fusion polypeptide is generated by fusing a variant M-SmallCas9 polypeptide with a heterologous sequence that provides for subcellular localization (e.g., the heterologous sequence is a subcellular localization sequence, e.g. a nuclear localization signal (NLS) for targeting to the nucleus; a mitochondrial localization signal for targeting to the mitochondria; a chloroplast localization signal for targeting to a chloroplast; an ER retention signal; and the like). In some embodiments, the heterologous sequence can provide a tag (e.g., the heterologous sequence is a detectable label) for ease of tracking and/or purification (e.g. a fluorescent protein, e.g. green fluorescent protein (GFP), YFP, RFP, CFP, mCherry, tdTomato, and the like; a histidine tag, e.g. a 6×His tag; a hemagglutinin (HA) tag; a FLAG tag; a Myc tag; and the like). In some embodiments, the heterologous sequence can provide for increased or decreased stability (e.g., the heterologous sequence is a stability control peptide, e.g. a degron, which in some cases is controllable (e.g. a temperature sensitive or drug controllable degron sequence, see below). In some embodiments, the heterologous sequence can provide for increased or decreased transcription from the target DNA (e.g., the heterologous sequence is a transcription modulation sequence, e.g. a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (e.g., the heterologous sequence is a protein binding sequence, e.g. to provide the ability of a fusion dM-SmallCas9 polypeptide to bind to another protein of interest, e.g. a DNA or histone modifying protein, a transcription factor or transcription repressor, a recruiting protein, etc.).

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled at least in part by the degron sequence. In some embodiments, a suitable degron is constitutive such that the degron exerts its influence on protein stability independent of experimental control (e.g., the degron is not drug inducible, temperature inducible, etc.). In some embodiments, the degron provides the variant M-SmallCas9 polypeptide with controllable stability such that the variant M-SmallCas9 polypeptide can be turned "on" (e.g., stable) or "off" (e.g., unstable, degraded) depending on the desired conditions. For example, if the degron is a temperature sensitive degron, the variant M-SmallCas9 polypeptide may be functional (e.g., "on", stable) below a threshold temperature (e.g. 42° C., 41° C., 40° C., 39° C., 38° C., 37° C., 36° C., 35° C., 34° C., 33° C., 32° C., 31° C., 30° C., etc.) but non-functional (e.g., "off", degraded) above the threshold temperature. As another example, if the degron is a drug inducible degron, the presence or absence of drug can switch the protein from an "off" (e.g., unstable) state to an "on" (e.g., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g. Dohmen et al., Science, 1994. 263 (5151): p. 1273-1276: Heat-inducible degron: a method for constructing temperature-sensitive mutants; Schoeber et al., Am J Physiol Renal Physiol. 2009 January; 296 (1): F204-11: Conditional fast expression and function of multimeric TRPV5 channels using Shield-1; Chu et al., Bioorg Med Chem Lett. 2008 Nov. 15; 18 (22): 5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48 (4): 487-8: Titivated for destruction: the methyl degron; Barbour et al., Biosci Rep. 2013 Jan. 18; 33 (1). Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well characterized and tested in both cells and animals. Thus, fusing M-SmallCas9 to a degron sequence produces a "tunable" and "inducible" M-SmallCas9 polypeptide. Any of the fusion partners described herein can be used in any desirable combination. As one non-limiting example to illustrate this point, a M-SmallCas9 fusion protein can comprise a YFP sequence for detection, a degron sequence for stability, and transcription activator sequence to increase transcription from the target DNA Furthermore, the number of fusion partners that can be used in a M-SmallCas9 fusion protein is unlimited. In some embodiments, a M-SmallCas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation activity, decrotonylation activity, propionylation activity, depropionylationa activity, myristoylation activity, or demyristoylation activity, any of which can be directed at modifying the DNA directly (e.g., methylation of DNA) or at modifying a DNA-associated polypeptide (e.g. a histone or DNA binding protein). Further suitable fusion partners include, but are not limited to boundary elements (e.g. CTCF), proteins and fragments thereof that provide periphery recruitment (e.g., Lamin A, Lamin B, etc.), and protein docking elements (e.g. FKBP/FRB, Pil 1/Aby 1, etc.).

The M-SmallCas9 polypeptides or variants thereof may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, at least about 75% by weight, at least about 95% by weight, and for therapeutic purposes, typically at least 99.5% by weight, in relation to contaminants related to the method of preparation of the product and its purification. Generally, the percentages will be based upon total protein. To induce DNA cleavage and recombination, or any desired modification to a target DNA, or any desired modification to a polypeptide associated with target DNA, the guide RNA and/or the M-SmallCas9 polypeptide or variant thereof and/or the donor polynucleotide, whether they be introduced as nucleic acids or polypeptides, are provided to the cells for about 30 minutes to about 24 hours, e.g. 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g. every 1.5 days, every 2 days, every 3 days, or any other frequency from about every day to about every four days. The agent(s) may be provided to the cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further. In cases in which two or more different targeting complexes are provided to the cell (e.g. two different guide RNAs that are complementary to different sequences within the same or different target DNA), the complexes may be provided simultaneously (e.g. as two polypeptides and/or nucleic acids), or delivered simultaneously. Alternatively, they may be provided consecutively, e.g. the targeting complex being provided first, followed by the second targeting complex, etc. or vice versa.

Nucleic Acids

Guide RNAs/sgRNAs

The systems, compositions, and methods described herein in some embodiments employ a genome-targeting nucleic acid that can direct the activities of an associated polypeptide (e.g., a M-SmallCas9 polypeptide or variant thereof) to a specific target sequence within a target nucleic acid. In some embodiments, the genome-targeting nucleic acid is an RNA. A genome-targeting RNA is referred to as a "guide RNA" or "gRNA" herein. A guide RNA has at least a spacer sequence that can hybridize to a target nucleic acid sequence of interest and a CRISPR repeat sequence (such a CRISPR repeat sequence is also referred to as a "tracr mate sequence"). In Type II systems, the gRNA also has a second RNA called the tracrRNA sequence. In the Type II guide RNA (gRNA), the CRISPR repeat sequence and tracrRNA sequence hybridize to each other to form a duplex. In the Type V guide RNA (gRNA), the crRNA forms a duplex. In both systems, the duplex binds a site-specific polypeptide such that the guide RNA and site-direct polypeptide form a complex. The genome-targeting nucleic acid provides target specificity to the complex by virtue of its association with the site-specific polypeptide. The genome-targeting nucleic acid thus directs the activity of the site-specific polypeptide.

In some embodiments, the genome-targeting nucleic acid is a double-molecule guide RNA. In some embodiments, the genome-targeting nucleic acid is a single-molecule guide RNA or single guide RNA (sgRNA). A double-molecule guide RNA has two strands of RNA. The first strand has in the 5' to 3' direction, an optional spacer extension sequence, a spacer sequence and a minimum CRISPR repeat sequence. The second strand has a minimum tracrRNA sequence (complementary to the minimum CRISPR repeat sequence), a 3' tracrRNA sequence and an optional tracrRNA extension sequence. A single-molecule guide RNA (sgRNA) in a Type II system has, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension may have elements that contribute additional functionality (e.g., stability) to the guide RNA. The single-molecule guide linker links the minimum CRISPR repeat and the minimum tracrRNA sequence to form a hairpin structure. The optional tracrRNA extension has one or more hairpins. A single-molecule guide RNA (sgRNA) in a Type V system has, in the 5' to 3' direction, a minimum CRISPR repeat sequence and a spacer sequence.

Exemplary genome-targeting nucleic acids are described, for example, in WO2018002719.

In general, a CRISPR repeat sequence includes any sequence that has sufficient complementarity with a tracr sequence to promote one or more of: (1) excision of a DNA targeting segment flanked by CRISPR repeat sequences in a cell containing the corresponding tracr sequence; and (2) formation of a CRISPR complex at a target sequence, wherein the CRISPR complex includes the CRISPR repeat sequence hybridized to the tracr sequence. In general, degree of complementarity is with reference to the optimal alignment of the CRISPR repeat sequence and tracr sequence, along the length of the shorter of the two sequences. Optimal alignment may be determined by any suitable alignment algorithm and may further account for secondary structures, such as self-complementarity within either the tracr sequence or CRISPR repeat sequence. In some embodiments, the degree of complementarity between the tracr sequence and CRISPR repeat sequence along the 30 nucleotides length of the shorter of the two when optimally aligned is about or more than 25%, 30%, 40%, 50%, 60%, 70%, 80%, 90%, 95%, 97.5%, 99%, or higher. In some embodiments, the tracr sequence is about or more than 5, 6, 7, 8, 9, 10, 11, 12, 13, 14, 15, 16, 17, 18, 19, 20, 25, 30, 40, 50, or more nucleotides in length. In some embodiments, the tracr sequence and CRISPR repeat sequence are contained within a single transcript, such that hybridization between the two produces a transcript having a secondary structure, such as a hairpin. In some embodiments, the transcript or transcribed polynucleotide sequence has at least two or more hairpins.

The spacer of a guide RNA includes a nucleotide sequence that is complementary to a sequence in a target DNA. In other words, the spacer of a guide RNA interacts with a target DNA in a sequence-specific manner via hybridization (e.g., base pairing). As such, the nucleotide sequence of the spacer may vary and determines the location within the target DNA that the guide RNA and the target DNA will interact. The DNA-targeting segment of a guide RNA can be modified (e.g. by genetic engineering) to hybridize to any desired sequence within a target DNA.

In some embodiments, the spacer has a length of from 10 nucleotides to 30 nucleotides. In some embodiments, the spacer has a length of from 13 nucleotides to 25 nucleotides. In some embodiments, the spacer has a length of from 15 nucleotides to 23 nucleotides. In some embodiments, the spacer has a length of from 18 nucleotides to 22 nucleotides, e.g., from 20 to 22 nucleotides.

In some embodiments, the percent complementarity between the DNA-targeting sequence of the spacer and the protospacer of the target DNA is at least 60% (e.g. at least 65%, at least 70%, at least 75%, at least 80%, at least 85%, at least 90%, at least 95%, at least 97%, at least 98%, at least 99%, or 100%) over the 20-22 nucleotides.

In some embodiments, the protospacer is directly adjacent to a suitable PAM sequence on its 3' end or such PAM sequence is part of the DNA targeting sequence in its 3' portion.

Modifications of guide RNAs can be used to enhance the formation or stability of the CRISPR-Cas genome editing complex comprising guide RNAs and a Cas endonuclease such as M-SmallCas9. Modifications of guide RNAs can also or alternatively be used to enhance the initiation, stability or kinetics of interactions between the genome editing complex with the target sequence in the genome, which can be used for example to enhance on-target activity. Modifications of guide RNAs can also or alternatively be used to enhance specificity, e.g. the relative rates of genome editing at the on-target site as compared to effects at other (off-target) sites.

Modifications can also or alternatively used to increase the stability of a guide RNA, e.g. by increasing its resistance to degradation by ribonucleases (RNases) present in a cell, thereby causing its half-life in the cell to be increased. Modifications enhancing guide RNA half-life can be particularly useful in embodiments in which a Cas endonuclease such as a M-SmallCas9 is introduced into the cell to be edited via an RNA that needs to be translated in order to generate M-SmallCas9 endonuclease, since increasing the half-life of guide RNAs introduced at the same time as the RNA encoding the endonuclease can be used to increase the time that the guide RNAs and the encoded Cas endonuclease co-exist in the cell.

Donor DNA or Donor Template

Site-specific polypeptides, such as a DNA endonuclease, can introduce double-strand breaks or single-strand breaks in nucleic acids, e.g., genomic DNA. The double-strand break can stimulate a cell's endogenous DNA-repair pathways (e.g., homology-dependent repair (HDR) or non-homologous end joining or alternative non-homologous end joining (A-NHEJ) or microhomology-mediated end joining (MMEJ). NHEJ can repair cleaved target nucleic acid without the need for a homologous template. This can sometimes result in small deletions or insertions (indels) in the target nucleic acid at the site of cleavage, and can lead to disruption or alteration of gene expression. HDR, which is also known as homologous recombination (HR) can occur when a homologous repair template, or donor, is available.

The homologous donor template has sequences that are homologous to sequences flanking the target nucleic acid cleavage site. The sister chromatid is generally used by the cell as the repair template. However, for the purposes of genome editing, the repair template is often supplied as an exogenous nucleic acid, such as a plasmid, duplex oligonucleotide, single-strand oligonucleotide, double-stranded oligonucleotide, or viral nucleic acid. With exogenous donor templates, it is common to introduce an additional nucleic acid sequence (such as a transgene) or modification (such as a single or multiple base change or a deletion) between the flanking regions of homology so that the additional or altered nucleic acid sequence also becomes incorporated into the target locus. MMEJ results in a genetic outcome that is similar to NHEJ in that small deletions and insertions can occur at the cleavage site. MMEJ makes use of homologous sequences of a few base pairs flanking the cleavage site to drive a favored end-joining DNA repair outcome. In some embodiments, it can be possible to predict likely repair outcomes based on analysis of potential microhomologies in the nuclease target regions.

Thus, in some cases, homologous recombination is used to insert an exogenous polynucleotide sequence into the target nucleic acid cleavage site. An exogenous polynucleotide sequence is termed a donor polynucleotide (or donor or donor sequence or polynucleotide donor template) herein. In some embodiments, the donor polynucleotide, a portion of the donor polynucleotide, a copy of the donor polynucleotide, or a portion of a copy of the donor polynucleotide is inserted into the target nucleic acid cleavage site. In some embodiments, the donor polynucleotide is an exogenous polynucleotide sequence, i.e., a sequence that does not naturally occur at the target nucleic acid cleavage site.

When an exogenous DNA molecule is supplied in sufficient concentration inside the nucleus of a cell in which the double strand break occurs, the exogenous DNA can be inserted at the double strand break during the NHEJ repair process and thus become a permanent addition to the genome. These exogenous DNA molecules are referred to as donor templates in some embodiments. If the donor template contains a coding sequence for one or more system components described herein optionally together with relevant regulatory sequences such as promoters, enhancers, polyA sequences and/or splice acceptor sequences, the one or more system components can be expressed from the integrated nucleic acid in the genome resulting in permanent expression for the life of the cell. Moreover, the integrated nucleic acid of the donor DNA template can be transmitted to the daughter cells when the cell divides.

In the presence of sufficient concentrations of a donor DNA template that contains flanking DNA sequences with homology to the DNA sequence either side of the double strand break (referred to as homology arms), the donor DNA template can be integrated via the HDR pathway. The homology arms act as substrates for homologous recombination between the donor template and the sequences either side of the double strand break. This can result in an error free insertion of the donor template in which the sequences either side of the double strand break are not altered from that in the un-modified genome.

Supplied donors for editing by HDR vary markedly but generally contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors can be used. These oligonucleotides range in size from less than 100 nt to over many kb, though longer ssDNA can also be generated and used. Double-stranded donors are often used, including PCR amplicons, plasmids, and mini-circles. In general, it has been found that an AAV vector is a very effective means of delivery of a donor template, though the packaging limits for individual donors is <5 kb. Active transcription of the donor increased HDR three-fold, indicating the inclusion of promoter can increase conversion. Conversely, CpG methylation of the donor can decrease gene expression and HDR.

In some embodiments, the donor DNA can be supplied with the nuclease or independently by a variety of different methods, for example by transfection, nanoparticle, micro-injection, or viral transduction. A range of tethering options can be used to increase the availability of the donors for HDR in some embodiments. Examples include attaching the donor to the nuclease, attaching to DNA binding proteins that bind nearby, or attaching to proteins that are involved in DNA end binding or repair.

In addition to genome editing by NHEJ or HDR, site-specific gene insertions can be conducted that use both the NHEJ pathway and HR. A combination approach can be applicable in certain settings, possibly including intron/exon borders. NHEJ can prove effective for ligation in the intron, while the error-free HDR can be better suited in the coding region.

Vectors

In another aspect, provided herein is a nucleic acid comprising a codon-optimized polynucleotide sequences encoding a M-SmallCas9 polypeptide or variant thereof, a gRNA, and/or any nucleic acid or proteinaceous molecule necessary to carry out the embodiments of the disclosure. In some embodiments, such a nucleic acid is a vector (e.g., a recombinant expression vector).

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some embodiments, a vector has one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. In some embodiments, the vector is a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct having the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., Molecular Therapy-Nucleic Acids 3, e161 (2014) doi: 10.1038/mtna.2014.12.

The expression vector can also contain a ribosome binding site for translation initiation and a transcription terminator. The expression vector can also include appropriate sequences for amplifying expression. The expression vector can also include nucleotide sequences encoding non-native tags (e.g., histidine tag, hemagglutinin tag, green fluorescent protein, etc.) that are fused to the site-specific polypeptide, thus resulting in a fusion protein.

In some embodiments, a promoter is an inducible promoter (e.g., a heat shock promoter, tetracycline-regulated promoter, steroid-regulated promoter, metal-regulated promoter, estrogen receptor-regulated promoter, etc.). In some embodiments, a promoter is a constitutive promoter (e.g., CMV promoter, UBC promoter). In some embodiments, the promoter is a spatially restricted and/or temporally restricted promoter (e.g., a tissue specific promoter, a cell type specific promoter, etc.). In some embodiments, a vector does not have a promoter for at least one gene to be expressed in a host cell if the gene is going to be expressed, after it is inserted into a genome, under an endogenous promoter present in the genome.

Modifications of Nucleic Acids and Polypeptides

In some embodiments, a polynucleotide described herein comprises one or more modifications which can be used, for example, to enhance activity, stability or specificity, alter delivery, reduce innate immune responses in host cells, further reduce the protein size, or for other enhancements, as further described herein and known in the art. In some embodiments, such modifications will result in M-SmallCas9 polypeptides comprising an amino acid sequence having at least 75%, at least 80%, at least 85%, at least 90%, at least 95%, at least 99%, or 100% amino acid sequence identity to the sequence of SEQ ID NO: 2.

Codon-Optimization

In certain embodiments, modified polynucleotides are used in a CRISPR-M-SmallCas9 system described herein, in which the guide RNAs and/or a DNA or an RNA comprising a polynucleotide sequence encoding a M-SmallCas9 polypeptide or variant thereof can be modified, as described and illustrated below. Such modified polynucleotides can be used in the CRISPR-M-SmallCas9 system to edit any one or more genomic loci. In some embodiments, such modifications in the polynucleotides of the disclosure are achieved via codon-optimization, e.g., codon-optimized based on specific host cells in which the encoded polypeptide is expressed. It will be appreciated by the skilled artisan that any nucleotide sequence and/or recombinant nucleic acid of the present disclosure can be codon optimized for expression in any species of interest. Codon optimization is well known in the art and involves modification of a nucleotide sequence for codon usage bias using species specific codon usage tables. The codon usage tables are generated based on a sequence analysis of the most highly expressed genes for the species of interest. In a non-limiting example, when the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences.

In some embodiments, a M-SmallCas9 polypeptide or variant thereof described herein is expressed from a codon-optimized polynucleotide sequence. For example, if the intended target cell were a human cell, a human codon-optimized polynucleotide sequence encoding M-SmallCas9 (or a M-SmallCas9 variant, e.g. enzymatically inactive variant) would be a suitable. As another non-limiting example, if the intended host cell were a mouse cell, then a mouse codon-optimized polynucleotide sequence encoding M-SmallCas9 (or M-SmallCas9 variant, e.g. enzymatically inactive variant) would be suitable.

Strategies and methodologies for codon optimization are known in the art and have been described for various systems including, but not limited to yeast (Outchkourov et al., Protein Expr Purif, 24 (1): 18-24 (2002)) and *E. coli* (Feng et al., Biochemistry, 39 (50): 15399-15409 (2000)). In some embodiments, the codon optimization was performed by using GeneGPS® Expression Optimization Technology (ATUM) and using the manufacturer's recommended expression optimization algorithms. In some embodiments, the polynucleotides of the disclosure are codon-optimized for increased expression in a human cell. In some embodiments, the polynucleotides of the disclosure are codon-optimized for increased expression in an *E. coli* cell. In some embodiments, the polynucleotides of the disclosure are codon-optimized for increased expression in an insect cell. In some embodiments, the polynucleotides of the disclosure are codon-optimized for increased expression in a Sf9 insect cell. In some embodiments, the expression optimization algorithms used in codon optimization procedure are defined to avoid putative poly-A signals (e.g. AATAAA and ATTAAA) as well as long (greater than 4) stretches of A's which can lead to polymerase slippage.

As is well understood in the art, codon optimization of a nucleotide sequence results in a nucleotide sequence having less than 100% identity (e.g., less than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) to the native nucleotide sequence but which still encodes a polypeptide having the same function as that encoded by the original, native nucleotide sequence. Thus, in representative embodiments of the disclosure, the nucleotide sequence and/or recombinant nucleic acid of the disclosure can be codon optimized for expression in the particular species of interest.

In some embodiments, a codon-optimized polynucleotide sequence has at least 90%, 92%, 93%, 94%, 95%, 96%, 97%, 98%, 99%, 99.2%, 99.5%, 99.8%, 99.9%, or 100% sequence identity to SEQ ID NO: 1. In some embodiments, the polynucleotides of the disclosure are codon-optimized for increased expression of the encoded M-SmallCas9 polypeptide in a target cell. In some embodiments, the polynucleotides of the disclosure are codon-optimized for increased expression in a human cell. Generally, the polynucleotides of the disclosure are codon-optimized for increased expression in any human cells. In some embodiments, the polynucleotides of the disclosure are codon-optimized for increased expression in an *E. coli* cell. In some embodiments, the polynucleotides of the disclosure are codon-optimized for increased expression in an insect cell. Generally, the polynucleotides of the disclosure are codon-optimized for increased expression in any insect cells. In some embodiments, the polynucleotides of the disclosure are codon-optimized for increased expression in a Sf9 insect cell expression system.

Polyadenylation signals can also be chosen to optimize expression in the intended host.

Other Modifications

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease such as M-SmallCas9 that are introduced into a cell, including, without limitation, modifications that enhance the stability of the RNA (such as by decreasing its degradation by RNases present in the cell), modifications that enhance translation of the resulting product (e.g., the endonuclease), and/or modifications that decrease the likelihood or degree to which the RNAs introduced into cells elicit innate immune responses. Combinations of modifications, such as the foregoing and others, can likewise be used. In the case of CRISPR-M-SmallCas9, for example, one or more types of modifications can be made to guide RNAs (including those exemplified above), and/or one or more types of modifications can be made to RNAs encoding M-SmallCas9 endonuclease (including those exemplified above).

By way of illustration, guide RNAs used in the CRISPR-M-SmallCas9 system or other smaller RNAs can be readily synthesized by chemical means, enabling a number of modifications to be readily incorporated, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating chemically-modified RNAs of greater length is to produce two or more molecules that are ligated together. Much longer RNAs, such as those encoding a M-SmallCas9 endonuclease, are more readily generated enzymatically. While fewer types of modifications are generally available for use in enzymatically produced RNAs, there are still modifications that can be used to, e.g. enhance stability, reduced the likelihood or degree of innate immune response, and/or enhance other attributes, as described further below and in the art; and new types of modifications are regularly being developed. By way of illustration of various types of modifications, especially those used frequently with smaller chemically synthesized RNAs, modifications can include one or more nucleotides modified at the 2' position of the sugar, in some embodiments a 2'-O-alkyl, 2'-O-alkyl-O-alkyl or 2'-fluoro-modified nucleotide. In some embodiments, RNA modifications include 2'-fluoro, 2'-amino and 2' O-methyl modifications on the ribose of pyrimidines, basic residues or an inverted base at the 3' end of the RNA. Such modifications are routinely incorporated into oligonucleotides and these oligonucleotides have been shown to have a higher Tm (e.g., higher target binding affinity) than; 2'-deoxy oligonucleotides against a given target.

A number of nucleotide and nucleoside modifications have been shown to make the oligonucleotide into which they are incorporated more resistant to nuclease digestion than the native oligonucleotide; these modified oligonucleotides survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly CH2-NH—O—CH2, CH, —N(CH3)-O—CH2 (known as a methylene (methylimino) or MMI backbone), CH2-O—N(CH3)-CH2, CH2-N(CH3)-N(CH3)-CH2 and O—N(CH3)-CH2-CH2 backbones; amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates including 3'alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Braasch and Corey, Biochemistry, 41 (14): 4503-4510 (2002); Genesis, Volume 30, Issue 3, (2001); Heasman, Dev. Biol., 243:209-214 (2002); Nasevicius et al., Nat. Genet., 26:216-220 (2000); Lacenra etc., Proc. Nat/. Acad. Sci., 97:9591-9596 (2000); and U.S. Pat. No. 5,034,506, issued Jul. 23, 1991. Cyclohexenyl nucleic acid oligonucleotide mimetics are described in Wang et al., J. Am. Chem. Soc., 122:8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, Sand CH2 component parts; see U.S. Pat. Nos. 5,034,506; 5,166,315; 5,185,444; 5,214,134; 5,216,141; 5,235,033; 5,264, 562; 5, 264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g. one of the following at the 2' position: OH, SH, SCH3, F, OCN, OCH3, OCH3 O(CH2)n CH3, O(CH2)n NH2 or O(CH2)n CH3 where n is from 1 to 10; C1 to C10 lower alkyl, alkoxyalkoxy, substituted lower alkyl, alkaryl or aralkyl; CI; Br; CN; CF3; OCF3; O—, S—, or N-alkyl; O—, S—, or N-alkenyl: SOCH3; SO2CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some embodiments, a modification includes 2'-methoxyethoxy (2'-O—CH2CH2OCH3, also known as 2'-O-(2-methoxyethyl)) (Martinet a/, Helv. Chim. Acta, 1995, 78, 486). Other modifications include 2'-methoxy (2'-O—CH3), 2'-propoxy (2'—OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group. In some embodiments, both a sugar and an internucleoside linkage, e.g., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262. Further teaching of PNA compounds can be found in Nielsen et al., Science, 254:1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g. hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g. 2-aminoadenine, 2-(methylamino) adenine, 2-(imidazolylalkyl) adenine, 2-(aminoalklyamino) adenine or other hetero-substituted alkyladenines, 2-thiouracil, 2-thiothymine, 5-bromouracil, 5-hydroxymethyluracil, 8-azaguanine, 7-deazaguanine, N6 (6-aminohexyl) adenine and 2,6-diaminopurine. Kornberg, A, DNA Replication, W. H. Freeman & Co., San Francisco, pp 75-77 (1980); Gebeyehu et al., Nucl. Acids Res. 15:4513 (1997). A "universal" base known in the art, e.g. inosine, can also be included. 5-Me-C substitutions have been shown to increase nucleic acid duplex stability by 0.6-1.2 degrees C. (Sanghvi, Y. S., in Crooke, S. T. and Lebleu, B., eds., Antisense Research and Applications, CRC Press, Boca Raton, 1993, pp. 276-278) and are embodiments of base substitutions.

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other a-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Other useful nucleobases include those disclosed in U.S. Pat. No. 3,687,808, those disclosed in "The Concise Encyclopedia of Polymer Science And Engineering", pages 858-859, Kroschwitz, J. I., ed. John Wiley & Sons, 1990, those disclosed by Englisch et al., Angewandte Chemie, International Edition, 1991, 30, page 613, and those disclosed in Sanghvi, Y. S., Chapter 15, Antisense Research and Applications, pages 289-302, Crooke, S. T. and Lebleu, B. ea., CRC Press, 1993. Certain of these nucleobases are particularly useful for increasing the binding affinity of the oligomeric compounds of the disclosure. These include 5-substituted pyrimidines, 6-azapyrimidines and N-2, N-6 and —O-6 substituted purines, including 2-aminopropyladenine, 5-propynyluracil and 5-propynylcytosine. 5-methylcytosine substitutions have been shown to increase nucleic acid duplex stability by 0.6-1.2 oc (Sanghvi, Y. S., Crooke, S. T. and Lebleu, B., eds, "Antisense Research and Applications", CRC Press, Boca Raton, 1993, pp. 276-278) and are embodiments of base substitutions, even more particularly when combined with 2'-O-methoxyethyl sugar modifications. Modified nucleobases are described in U.S. Pat. Nos. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and US Patent Application Publication 20030158403.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, the guide RNAs and/or mRNA encoding an endonuclease such as M-SmallCas9 of the disclosure are capped using any one of current capping methods such as mCAP, ARCA or enzymatic capping methods to create viable mRNA constructs that remain biologically active and avoid self/non-self intracellular responses. In some embodiments, the guide RNAs and/or mRNA encoding an endonuclease such as M-SmallCas9 of the disclosure are capped by using a CleanCap™ (TriLink) co-transcriptional capping method.

In some embodiments, the guide RNAs and/or mRNA encoding an endonuclease of the disclosure includes one or more modifications selected from the group consisting of pseudouridine, N1-methylpseudouridine, and 5-methoxyuridine. In some embodiments, one or more N1. methylpseudouridines are incorporated into the guide RNAs and/or mRNA encoding an endonuclease of the disclosure in order to provide enhanced RNA stability and/or protein expression and reduced immunogenicity in animal cells, such as mammalian cell (e.g., human and mice). In some embodiments, the N1-methylpseudouridine modifications are incorporated in combination with one or more 5-methylcytidines.

In some embodiments, the guide RNAs and/or mRNA (or DNA) encoding an endonuclease such as M-SmallCas9 are chemically linked to one or more moieties or conjugates that enhance the activity, cellular distribution, or cellular uptake of the oligonucleotide. Such moieties include but are not limited to, lipid moieties such as a cholesterol moiety [Letsinger et al., Proc. Nat/. Acad. Sci. USA, 86:6553-6556 (1989)]; cholic acid [Manoharan et al., Bioorg. Med. Chem. Let., 4:1053-1060 (1994)]; a thioether, e.g. hexyl-S-tritylthiol [Manoharan eta/, Ann. N. Y Acad. Sci., 660:306-309 (1992) and Manoharan et al., Bioorg. Med. Chem. Let., 3.•2765-2770 (1993)); a thiocholesterol [Oberhauser et al., Nucl. Acids Res., 20:533-538 (1992)]; an aliphatic chain, e.g. dodecandiol or undecyl residues [Kabanov et al., FEBS Lett., 259:327-330 (1990) and Svinarchuk et al., Biochimie, 75:49-54 (1993)]; a phospholipid, e.g. di-hexadecyl-rac-glycerol or triethylammonium 1,2-di-O-hexadecyl-rac-glycero-3-H-phosphonate [Manoharan et al., Tetrahedron Lett., 36:3651-3654 (1995) and Shea et al., Nucl. Acids Res., 18:3777-3783 (1990)]; a polyamine or a polyethylene glycol chain [Mancharan etc., Nucleosides & Nucleotides, 14:969-973 (1995)]; adamantane acetic acid [Manoharan et al., Tetrahedron Lett., 36:3651-3654 (1995)]; a palmityl moiety [(Mishra etc., Biochim. Biophys. Acta, 1264:229-237 (1995)]; or an octadecylamine or hexylamino-carbonyl-t oxycholesterol moiety [Crooke et al., J. Pharmacol. Exp. Ther., 277:923-937 (1996)]. See also U.S. Pat. Nos. 4,828, 979; 4,948,882; 5,218,105; 5,525,465; 5,541,313; 5,545, 730; 5,552, 538; 5,578,717, 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762, 779; 4,789,737; 4,824,941; 4,835, 263; 4,876,335; 4,904,582; 4,958,013; 5,082, 830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391, 723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599, 928 and 5,688,941.

Sugars and other moieties can be used to target proteins and complexes including nucleotides, such as cationic polysomes and liposomes, to particular sites. For example, hepatic cell directed transfer can be mediated via asialoglycoprotein receptors (ASGPRs); see, e.g. Hu, et al., Protein Pept Lett. 21 (1 0): 1025-30 (2014). Other systems known in the art and regularly developed can be used to target biomolecules of use in the present case and/or complexes thereof to particular target cells of interest.

These targeting moieties or conjugates can include conjugate groups covalently bound to functional groups such as primary or secondary hydroxyl groups. Suitable conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that are capable of enhancing the pharmacodynamic properties include groups that improve uptake, enhance resistance to degradation, and/or strengthen sequence-specific hybridization with the target nucleic acid. Groups that are capable of enhancing the pharmacokinetic properties include groups that improve uptake, distribution, metabolism or excretion of the compounds of the present disclosure. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g. hexyl-5-tritylthiol, a thiocholesterol, an aliphatic chain, e.g. dodecandiol or undecyl residues, a phospholipid, e.g. di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g. U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are generally produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding M-SmallCas9 is approximately 4 kb in length and can be synthesized by in vitro transcription. Modifications to the mRNA can be applied to, e.g. increase its translation or stability (such as by increasing its resistance to degradation with a cell), or to reduce the tendency of the RNA to elicit an innate immune response that is often observed in cells following introduction of exogenous RNAs, particularly longer RNAs such as that encoding M-SmallCas9.

Numerous such modifications have been described in the art, such as polyA tails, 5' cap analogs (e.g., Anti Reverse Cap Analog (ARCA) or m7G (5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, Axolabs, Bio-Synthesis Inc., Dharmacon and many others. As described by TriLink, for example, 5-Methyl-CTP can be used to impart desirable characteristics such as increased nuclease stability, increased translation or reduced interaction of innate immune receptors with in vitro transcribed RNA. 5'-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation as illustrated in publications by Konmann et al. and Warren et al. referred to below.

It has been shown that chemically modified mRNA delivered in vivo can be used to achieve improved therapeutic effects; see, e.g. Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found substituting just one quarter of the uridine and cytidine residues with 2-Thio-U and 5-Methyl-C respectively, resulted in a significant decrease in toll-like receptor (TLR) mediated recognition of the mRNA in mice. By reducing the activation of the innate immune system, these modifications can therefore be used to effectively increase the stability and longevity of the mRNA in vivo; see, e.g. Konmann et al., supra.

It has also been shown that repeated administration of synthetic messenger RNAs incorporating modifications designed to bypass innate anti-viral responses can reprogram differentiated human cells to pluripotency. See, e.g. Warren, et al., Cell Stem Cell, 7(5): 618-30 (2010). Such modified mRNAs that act as primary reprogramming proteins can be an efficient means of reprogramming multiple human cell types. Such cells are referred to as induced pluripotency stem cells (iPSCs). and it was found that enzymatically synthesized RNA incorporating 5-Methyl-CTP, Pseudo-UTP and an Anti Reverse Cap Analog (ARCA) could be used to effectively evade the cell's antiviral response; see, e.g. Warren et al., supra. Other modifications of polynucleotides described in the art include, for example, the use of polyA tails, the addition of 5' cap analogs (such as m7G (5')ppp(5')G (mCAP)), modifications of 5' or 3' untranslated regions (UTRs), or treatment with phosphatase to remove 5' terminal phosphates- and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g. the reviews by Angart et al., Pharmaceuticals (Basel) 6(4): 440-468 (2013); Kanasty et al., Molecular Therapy 20(3): 513-524 (2012); Burnett et al., Biotechnol J. 6(9): 1130-46 (2011); Judge and Maclachlan, Hum Gene Ther 19(2):111-24 (2008); and references cited therein.

A large variety of modifications have been developed and applied to enhance RNA stability, reduce innate immune responses, and/or achieve other benefits that can be useful in connection with the introduction of polynucleotides into human cells as described herein; see, e.g. the reviews by Whitehead K A et al., Annual Review of Chemical and Biomolecular Engineering, 2:77-96 (2011); Gaglione and Messere, Mini Rev Med Chem, 10 (7): 578-95 (2010); Chernolovskaya et al, Curr Opin Mol Ther., 12 (2): 158-67 (2010); Deleavey et al., Curr Protoc Nucleic Acid Chem Chapter 16: Unit 16.3 (2009); Behlke, Oligonucleotides 18 (4): 305-19 (2008): Fucini et al., Nucleic Acid Ther 22 (3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kale, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O—, 2'-Fluoro, 2'-Hydro) has been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fiuoro, 2'-Hydro have been reported to reduce TLR7/TLR8 interaction while generally preserving silencing activity; see, e.g. Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g. Kariko et al., Immunity 23:165-175 (2005).

As is also known in the art, and commercially available, a number of conjugates can be applied to polynucleotides such as RNAs for use herein that can enhance their delivery and/or uptake by cells, including for example, cholesterol, tocopherol and folic acid, lipids, peptides, polymers, linkers and aptamers; see, e.g. the review by Winkler, Ther. Deliv. 4:791-809 (2013), and references cited therein.

Additional Sequences

In some embodiments, a guide RNA comprises at least one additional segment at either the 5' or 3' end. For example, a suitable additional segment can comprise a 5' cap (e.g. a 7-methylguanylate cap (m7G)); a 3' polyadenylated tail (e.g., a 3' poly(A) tail); a riboswitch sequence (e.g. to allow for regulated stability and/or regulated accessibility by proteins and protein complexes); a sequence that forms a dsRNA duplex (e.g., a hairpin)); a sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like) a modification or sequence that provides for increased, decreased, and/or controllable stability; and combinations thereof.

Stability Control Sequence

A stability control sequence influences the stability of an RNA (e.g. a guide RNA). A non-limiting example of a suitable stability control sequence is a transcriptional terminator segment (e.g., a transcription termination sequence). A transcriptional terminator segment of a guide RNA can have a total length of from 10 nucleotides to 100 nucleotides, e.g. from 10 nucleotides (nt) to 20 nt, from 20 nt to 30 nt, from 30 nt to 40 nt, from 40 nt to 50 nt, from 50 nt to 60 nt, from 60 nt to 70 nt, from 70 nt to 80 nt, from 80 nt to 90 nt, or from 90 nt to 100 nt. For example, the transcriptional terminator segment can have a length of from 15 nucleotides (nt) to 80 nt, from 15 nt to 50 nt, from 15 nt to 40 nt, from 15 nt to 30 nt or from 15 nt to 25 nt.

In some embodiments, the transcription termination sequence is one that is functional in a eukaryotic cell. In some embodiments, the transcription termination sequence is one that is functional in a prokaryotic cell.

Nucleotide sequences that can be included in a stability control sequence (e.g. transcriptional termination segment, or in any segment of the guide RNA to provide for increased stability) include, for example, a Rho-independent trp termination site.

Mimetics

In some embodiments, a nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units, which gives PNA an amide containing backbone. The heterocyclic base moieties are bound directly or indirectly to aza nitrogen atoms of the amide portion of the backbone. Representative US patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are nonionic mimics of oligonucleotides, which are less likely to form undesired interactions with cellular proteins (Dwaine A. Braasch and David R. Corey, Biochemistry, 2002, 41 (14), 45034510). Morpholino-based polynucleotides are disclosed in U.S. Pat.

No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (GeNA). The furanose ring normally present in a DNA/RNA molecule is replaced with a cydohexenyl ring. GeNA DMT protected phosphoramidite monomers have been prepared and used for oligomeric compound synthesis following classical phosphoramidite chemistry. Fully modified GeNA oligomeric compounds and oligonucleotides having specific positions modified with GeNA have been prepared and studied (see Wang et al., J. Am. Chem. Soc., 2000, 122, 85958602). In general the incorporation of GeNA monomers into a DNA chain increases its stability of a DNA/RNA hybrid. GeNA oligoadenylates formed complexes with RNA and DNA complements with similar stability to the native complexes. The study of incorporating GeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A, 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A nucleic acid can also include one or more substituted sugar moieties. Suitable polynucleotides include a sugar substituent group selected from: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly suitable are O((CH2)nO) mCH3, O(CH2)nOCH3, O(CHz)nNH2, O(CH2)CH3, O(CH2)nONH2, and O(CH2)nON((CH2)nCH3)2, where n and m are from 1 to about 10. Other suitable polynucleotides include a sugar substituent group selected from: C1 to C10 lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy 21-O—CH2-CH2OCH3, also known as -2'-O-(2-methoxyethyl) or 2'-MOE) (Martin et al., Helv. Chim. Acta, 1995, 78, 486-504) e.g., an alkoxyalkoxy group. A further suitable modification includes 2'-dimethylaminooxyethoxy, e.g., a O(CH2)2ON(CH3)2 group (2'-DMAOE), as described in examples herein below, and 2'-dimethylamino-ethoxyethoxy (also known in the art as 21-O-dimethyl-amino-ethoxy-ethyl or 2'-DMAEOE), e.g., 2'-O—CH2-O—CH2-N(CH3)2.

Other suitable sugar substituent groups include methoxy (—O—CH3), aminopropoxy (—O—CH2CH2CH2NH2), allyl (—CH2-CH═CH2), —O-allyl (—O—CH2-CH═CH2) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C═C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b) (1,4)benzoxazin-2 (3H)-one), phenothiazine cytidine (1H-pyrimido(5,4-b) (1,4)benzothiazin-2 (3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b) indol-2-one), pyridoindole cytidine (H-pyrido (3',21:4,5) pyrrolo (2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. 1., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2 oc. (Sanghvi et al., eds., Antisense Research and Applications, CRC Press, Boca Raton, 1993, pp. 276-278) and are suitable base substitutions, e.g. when combined with 2'-O-methoxyethyl sugar modifications.

"Complementary" refers to the capacity for pairing, through base stacking and specific hydrogen bonding, between two sequences comprising naturally or non-naturally occurring (e.g. modified as described above) bases (nucleosides) or analogs thereof. For example, if a base at one position of a nucleic acid is capable of hydrogen bonding with a base at the corresponding position of a target, then the bases are considered to be complementary to each other at that position. Nucleic acids can include universal bases, or inert abasic spacers that provide no positive or negative contribution to hydrogen bonding. Base pairings may include both canonical Watson-Crick base pairing and non-Watson-Crick base pairing (e.g. Wobble base pairing and Hoogsteen base pairing).

It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and Santalucia, Nucl. Acids Research, 2005; 33 (19): 6258-6267.

Conjugates

Another possible modification of a nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g. hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g. dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g. di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 36513654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacal. Exp. Ther., 1996, 277, 923-937).

A conjugate may include a "Protein Transduction Domain" or PTD (also known as a CPP-cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of an exogenous polypeptide (e.g. a M-SmallCas9 polypeptide or variant thereof). In some embodiments, a PTD is covalently linked to the C-terminus or the N-terminus of an exogenous polypeptide (e.g. a M-SmallCas9 polypeptide or variant thereof). In some embodiments, a PTD is covalently linked to a nucleic acid (e.g. a guide RNA, a polynucleotide encoding a guide RNA, a polynucleotide encoding a M-SmallCas9 polypeptide or variant thereof, etc.). Exemplary PTDs include but are not limited to a minimal undecapeptide protein transduction domain (corresponding to residues 47-57 of HIV-1 TAT comprising YGRKKRRORRR; a polyarginine sequence comprising a number of arginines sufficient to direct entry into a cell (e.g. 3, 4, 5, 6, 7, 8, 9, 10, or 10-50 arginines); a VP22 domain (Zender et al. (2002) Cancer Gene Ther. 9 (6): 489-96); an Drosophila Antennapedia protein transduction domain (Noguchi et al. (2003) Diabetes 52 (7): 1732-1737); a truncated human calcitonin peptide (Trehin et al. (2004) Pharm. Research 21:1248-1256); polylysine (Wender et al. (2000) Proc. Natl. Acad. Sci. USA 97:13003-13008); In some embodiments, the PTD is an activatable CPP (ACPP) (Aguilera et al. (2009) Integr Biol (Camb) June; 1 (5-6): 371-381). ACPPs include a polycationic CPP (e.g. Arg9 or "R9") connected via a cleavable linker to a matching polyanion (e.g. Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane. In some embodiments the PTD is chemically modified in order to increase the bioavailability of the PTD. Exemplary modifications are disclosed in Expert Opin Drug Deliv. 2009 November; 6 (11): 1195-205.

Polypeptide Modifications

A M-SmallCas9 polypeptide or variant thereof expressed from a codon-optimized polynucleotide sequence may be produced in vitro or by eukaryotic cells, by prokaryotic cells, or by in-vitro transcription and translation (IVTT) and it may be further processed by unfolding, e.g. heat denaturation, OTT reduction, etc. and may be further refolded, using methods known in the art.

Modifications of interest that do not alter primary sequence include chemical derivatization of polypeptides, e.g. acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

In some embodiments, M-SmallCas9 polypeptides or variants thereof have been modified using ordinary molecular biological techniques and synthetic chemistry so as to improve their resistance to proteolytic degradation, to change the target sequence specificity, to optimize solubility properties, to alter protein activity (e.g. transcription modulatory activity, enzymatic activity, etc.) or to render them more suitable as a therapeutic agent. Analogs of such polypeptides include those containing residues other than naturally occurring L-amino acids, e.g. O-amino acids or unnatural, synthetic amino acids. D-amino acids may be substituted for some or all of the amino acid residues. The M-SmallCas9 polypeptides or variants thereof may be prepared by in vitro synthesis, using conventional methods as known in the art. Various commercial synthetic apparatuses are available, for example, automated synthesizers by Applied Biosystems, Inc., Beckman, etc. By using synthesizers, natural amino acids may be substituted with unnatural amino acids. The particular sequence and the manner of preparation may be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Recombinant Cells

In some embodiments, the codon-optimized M-SmallCas9 system herein described can be used in eukaryotic, such as mammalian cells, for example, a human cell. Any human cell is suitable for use with the codon-optimized M-SmallCas9 system disclosed herein.

In some embodiments, a cell ex vivo or in vitro includes: (a) a nucleic acid comprising a codon-optimized polynucleotide sequence encoding a M-SmallCas9 polypeptide or variant described herein, or a M-SmallCas9 polypeptide or variant thereof expressed from the nucleic acid; and (b) a gRNA or nucleic acid encoding the gRNA, wherein the gRNA is capable of guiding the M-SmallCas9 polypeptide or variant thereof to a target polynucleotide sequence. In some embodiments, the cell comprises the nucleic acid comprising the codon-optimized polynucleotide sequence. In some embodiments, the cell comprises the gRNA. In some embodiments, the cell comprises nucleic acid encoding the gRNA. In some embodiments, the gRNA is a single guide RNA (sgRNA). In some embodiments, the cell comprises one or more additional gRNAs or nucleic acid encoding the one or more additional gRNAs. In some embodiments, the cell further comprises a donor template.

In one aspect, some embodiments disclosed herein relate to a method of transforming a cell that includes introducing into a host cell, such as an animal cell, a nucleic acid as provided herein, and selecting or screening for a transformed cell. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Techniques for transforming a wide variety of the above-mentioned host cells and species are known in the art and described in the technical and scientific literature. Accordingly, cell cultures comprising at least one recombinant cell as disclosed herein are also within the scope of this application. Methods and systems suitable for generating and maintaining cell cultures are known in the art.

In a related aspect, some embodiments relate to recombinant host cells, for example, recombinant animal cells that include a nucleic acid described herein. The nucleic acid can be stably integrated in the host genome, or can be episomally replicating, or present in the recombinant host cell as a mini-circle expression vector for a stable or transient expression. Accordingly, in some embodiments disclosed herein, the nucleic acid is maintained and replicated in the recombinant host cell as an episomal unit. In some embodiments, the nucleic acid is stably integrated into the genome of the recombinant cell. In some embodiments, the nucleic acid present in the recombinant host cell as a mini-circle expression vector for a stable or transient expression.

In some embodiments, host cells can be genetically engineered (e.g. transduced or transformed or transfected) with, for example, a vector construct of the present application that can be, for example, a vector for homologous recombination that includes nucleic acid sequences homologous to a portion of the genome of the host cell, or can be an expression vector for the expression of any or a combination of the genes of interest. The vector can be, for example, in the form of a plasmid, a viral particle, a phage, etc. In some embodiments, a vector for expression of a polypeptide of interest can also be designed for integration into the host, e.g., by homologous recombination.

In some embodiments, the disclosure provides a genetically modified host cell, e.g. isolated genetically modified host cell, where a genetically modified host cell includes: 1) an exogenous guide RNA; 2) an exogenous nucleic acid comprising a nucleotide sequence encoding a guide RNA; 3) an exogenous nucleic acid comprising a codon-optimized polynucleotide sequence encoding a M-SmallCas9 polypeptide or variant thereof; 4) an exogenous M-SmallCas9 polypeptide or variant thereof expressed from a nucleic acid comprising a codon-optimized polynucleotide sequence; or 5) any combination of the above. In some embodiments, the genetically modified cell is generated by genetically modifying a host cell with, for example: 1) an exogenous guide RNA; 2) an exogenous nucleic acid comprising a nucleotide sequence encoding a guide RNA; 3) an exogenous nucleic acid comprising a codon-optimized polynucleotide sequence encoding a M-SmallCas9 polypeptide or variant thereof; 4) an exogenous M-SmallCas9 polypeptide or variant thereof expressed from a nucleic acid comprising a codon-optimized polynucleotide sequence; or 5) any combination of the above.

All cells suitable to be a target cell as discussed above are also suitable to be a genetically modified host cell. For example, a genetically modified host cells of interest can be a cell from any organism, e.g., a bacterial cell, an archaeal cell, a cell of a single-cell eukaryotic organism, a plant cell, an algal cell (e.g., *Botryococcus braunii, Chlamydomonas reinhardtii, Nannochloropsis* gaditana, *Chlorela pyrenoidosa, Sargassum patens* (*C. agardh*), and the like), a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent. a rat, a mouse, a non-human primate, a human, etc.). In some embodiments, the genetically modified host cell can be any cell from a human.

In some embodiments, the genetically modified host cell of the disclosure has been genetically modified with an exogenous nucleic acid comprising a nucleotide sequence encoding a M-SmallCas9 polypeptide or variant thereof. In some embodiments, the genetically modified host cell has been genetically modified with an exogenous nucleic acid comprising a nucleotide sequence encoding for a M-SmallCas9 polypeptide or a variant described herein. The DNA of a genetically modified host cell can be targeted for modification by introducing into the cell a guide RNA (or a DNA encoding a guide RNA, which determines the genomic location/sequence to be modified) and optionally a donor nucleic acid. In some embodiments, the nucleotide sequence encoding a M-SmallCas9 polypeptide or variant thereof is operably linked to an inducible promoter (e.g. heat shock promoter, Tetracycline-regulated promoter, Steroid-regulated promoter, Metal-regulated promoter, estrogen receptor-regulated promoter, etc.). In some embodiments, the codon-optimized nucleotide sequence encoding a M-SmallCas9 polypeptide or variant thereof is operably linked to a spatially restricted and/or temporally restricted promoter (e.g. a tissue specific promoter, a cell type specific promoter, a cell cycle specific promoter). In some embodiments, the codon-optimized nucleotide sequence encoding a M-SmallCas9 polypeptide or variant thereof is operably linked to a constitutive promoter.

In some embodiments, a genetically modified host cell is in vitro. In some embodiments, a genetically modified host cell is in vivo. In some embodiments, a genetically modified host cell is a prokaryotic cell or is derived from a prokaryotic cell. In some embodiments, a genetically modified host cell is a bacterial cell or is derived from a bacterial cell. In some embodiments, a genetically modified host cell is an archaeal cell or is derived from an archaeal cell. In some embodiments, a genetically modified host cell is a eukaryotic cell or is derived from a eukaryotic cell. In some embodiments, a genetically modified host cell is a plant cell or is derived from a plant cell. In some embodiments, a genetically modified host cell is an animal cell or is derived from an animal cell. In some embodiments, a genetically modified host cell is an invertebrate cell or is derived from an invertebrate cell. In some embodiments, a genetically modified host cell is a vertebrate cell or is derived from a vertebrate cell. In some embodiments, a genetically modified host cell is a mammalian cell or is derived from a mammalian cell. In some embodiments, a genetically modified host cell is a rodent cell or is derived from a rodent cell. In some embodiments, a genetically modified host cell is a human cell or is derived from a human cell. In some embodiments, the genetically modified host cell is a human cell or is derived from a human cell.

The present disclosure further provides progeny of a genetically modified cell, where the progeny can include the same exogenous nucleic acid or polypeptide as the genetically modified cell from which it was derived. The present disclosure further provides, in some embodiments, a composition comprising a genetically modified host cell.

In some embodiments, a genetically modified host cell is a genetically modified stem cell or progenitor cell. Suitable host cells include, e.g. stem cells (adult stem cells, embryonic stem cells, iPS cells, etc.) and progenitor cells (e.g., cardiac progenitor cells, neural progenitor cells, etc.). Other suitable host cells include mammalian stem cells and progenitor cells, such as, e.g., rodent stem cells, rodent progenitor cells, human stem cells, human progenitor cells, etc. Other suitable host cells include in vitro host cells, e.g., isolated host cells. In some embodiments, a genetically modified host cell includes an exogenous guide RNA nucleic acid. In some embodiments, a genetically modified host cell includes an exogenous nucleic acid comprising a nucleotide sequence encoding a guide RNA. In some embodiments, a genetically modified host cell includes an exogenous M-SmallCas9 polypeptide or variant thereof expressed from a codon-optimized nucleotide sequence. In some embodiments, a genetically modified host cell includes an exogenous nucleic acid comprising a codon-optimized nucleotide sequence encoding a M-SmallCas9 polypeptide or variant thereof. In some embodiments, a genetically modified host cell includes exogenous nucleic acid comprising 1) a nucleotide sequence encoding a guide RNA and 2) a codon-optimized nucleotide sequence encoding a M-SmallCas9 polypeptide or variant thereof.

Non-Human Genetically Modified Organisms

In some embodiments, a genetically modified host cell has been genetically modified with an exogenous nucleic acid comprising a codon-optimized nucleotide sequence encoding a M-SmallCas9 polypeptide or variant thereof. If such a cell is a eukaryotic single-cell organism, then the modified cell can be considered a genetically modified organism. In some embodiments, the non-human genetically modified organism is a M-SmallCas9 transgenic multicellular organism.

In some embodiments, a genetically modified non-human host cell (e.g. a cell that has been genetically modified with an exogenous nucleic acid comprising a codon-optimized nucleotide sequence encoding a M-SmallCas9 polypeptide or variant thereof) can generate a genetically modified nonhuman organism (e.g. a mouse, a fish, a frog, a fly, a worm, etc.). For example, if the genetically modified host cell is a pluripotent stem cell (e.g., PSC) or a germ cell (e.g. sperm, oocyte, etc.), an entire genetically modified organism can be derived from the genetically modified host cell. In some embodiments, the genetically modified host cell is a pluripotent stem cell (e.g. ESC, iPSC, pluripotent plant stem cell, etc.) or a germ cell (e.g. sperm cell, oocyte, etc.), either in vivo or in vitro that can give rise to a genetically modified organism. In some embodiments the genetically modified host cell is a vertebrate PSC (e.g. ESC, iPSC, etc.) and is used to generate a genetically modified organism (e.g. by injecting a PSC into a blastocyst to produce a chimeric/mosaic animal, which could then be mated to generate non-chimeric/non-mosaic genetically modified organisms; grafting in the case of plants; etc.). Any suitable method/protocol for producing a genetically modified organism, including the methods described herein, is suitable for producing a genetically modified host cell comprising an exogenous nucleic acid comprising a codon-optimized nucleotide sequence encoding a M-SmallCas9 polypeptide or variant thereof. Methods of producing genetically modified organisms are known in the art. For example, see Cho et al., Curr Protoc Cell Biol. 2009 March; Chapter 19: Unit 19.11: Generation of transgenic mice; Gama et al., Brain Struct Funct. 2010 March; 214 (2-3): 91-109. Epub 2009 Nov. 25: Animal transgenesis: an overview; Husaini et al., GM Crops. 2011 June-December; 2 (3): 150-62. Epub 2011 Jun. 1: Approaches for gene targeting and targeted gene expression in plants.

In some embodiments, a genetically modified organism comprises a target cell for methods of the disclosure, and thus can be considered a source for target cells. For example, if a genetically modified cell comprising an exogenous nucleic acid comprising a codon-optimized nucleotide sequence encoding a M-SmallCas9 polypeptide or variant thereof is used to generate a genetically modified organism, then the cells of the genetically modified organism comprise the exogenous nucleic acid comprising a codon-optimized nucleotide sequence encoding a M-SmallCas9 polypeptide or variant thereof. In some such embodiments, the DNA of a cell or cells of the genetically modified organism can be targeted for modification by introducing into the cell or cells a guide RNA (or a DNA encoding a guide RNA) and optionally a donor nucleic acid. For example, the introduction of a guide RNA (or a DNA encoding a guide RNA) into a subset of cells (e.g. brain cells, intestinal cells, kidney cells, lung cells, blood cells, etc.) of the genetically modified organism can target the DNA of such cells for modification, the genomic location of which will depend on the DNA-targeting sequence of the introduced guide RNA.

In some embodiments, a genetically modified organism is a source of target cells for methods of the disclosure. For example, a genetically modified organism comprising cells that are genetically modified with an exogenous nucleic acid comprising a codon-optimized nucleotide sequence encoding a M-SmallCas9 polypeptide or variant thereof can provide a source of genetically modified cells, for example PSCs (e.g. ESCs, iPSCs, sperm, oocytes, etc.), neurons, progenitor cells, cardiomyocytes, etc.

In some embodiments, a genetically modified cell is a PSC comprising an exogenous nucleic acid comprising a codon-optimized nucleotide sequence encoding a M-SmallCas9 polypeptide or variant thereof. As such, the PSC can be a target cell such that the DNA of the PSC can be targeted for modification by introducing into the PSC a guide RNA (or a DNA encoding a guide RNA) and optionally a donor nucleic acid, and the genomic location of the modification will depend on the DNA-targeting sequence of the introduced guide RNA. Thus, in some embodiments, the methods described herein can be used to modify the DNA (e.g. delete and/or replace any desired genomic location) of PSCs derived from a genetically modified organism. Such modified PSCs can then be used to generate organisms having both (i) an exogenous nucleic acid comprising a codon-optimized nucleotide sequence encoding a M-SmallCas9 polypeptide or variant thereof and (ii) a DNA modification that was introduced into the PSC.

In some embodiments, the exogenous nucleic acid can be under the control of (e.g., operably linked to) an unknown promoter (e.g. when the nucleic acid randomly integrates into a host cell genome) or can be under the control of (e.g., operably linked to) a known promoter. Suitable known promoters can be any known promoter and include constitutively active promoters (e.g. CMV promoter), inducible promoters (e.g. heat shock promoter, Tetracycline-regulated promoter, Steroid-regulated promoter, Metal-regulated promoter, estrogen receptor-regulated promoter, etc.), spatially restricted and/or temporally restricted promoters (e.g. a tissue specific promoter, a cell type specific promoter, etc.), etc.

A genetically modified organism (e.g. an organism whose cells comprise a codon-optimized nucleotide sequence encoding a M-SmallCas9 polypeptide or variant thereof) can be any organism including for example, a plant; algae; an invertebrate (e.g. a cnidarian, an echinoderm, a worm, a fly, etc.); a vertebrate (e.g. a fish (e.g. zebrafish, puffer fish, gold fish, etc.), an amphibian (e.g. salamander, frog, etc.), a reptile, a bird, a mammal, etc.); an ungulate (e.g. a goat, a pig, a sheep, a cow, etc.); a rodent (e.g. a mouse, a rat, a hamster, a guinea pig); a lagomorpha (e.g. a rabbit); etc.

In some embodiments, the active portion are the RNase domains. In some embodiments, the active portions are the DNase domain.

Transgenic Non-Human Animals

As described above, in some embodiments, a nucleic acid (e.g. a codon-optimized nucleotide sequence encoding a M-SmallCas9 polypeptide or variant thereof) or a recombinant expression vector is used as a transgene to generate a transgenic animal that produces a M-SmallCas9 polypeptide or variant thereof. Thus, the present disclosure further provides a transgenic non-human animal, which animal comprises a transgene comprising a nucleic acid comprising a codon-optimized nucleotide sequence encoding a M-SmallCas9 polypeptide or variant thereof, as described above. In some embodiments, the genome of the transgenic non-human animal comprises a codon-optimized nucleotide sequence encoding a M-SmallCas9 polypeptide or variant thereof. In some embodiments, the transgenic non-human animal is homozygous for the genetic modification. In some embodiments, the transgenic non-human animal is heterozygous for the genetic modification. In some embodiments, the transgenic non-human animal is a vertebrate, for example, a fish (e.g. zebra fish, gold fish, puffer fish, cave fish, etc.), an amphibian (frog, salamander, etc.), a bird (e.g. chicken, turkey, etc.), a reptile (e.g. snake, lizard, etc.), a mammal (e.g. an ungulate, e.g. a pig, a cow, a goat, a sheep, etc.; a lagomorph (e.g. a rabbit); a rodent (e.g. a rat, a mouse); a nonhuman primate; etc.), etc.

In some embodiments, the nucleic acid is an exogenous nucleic acid comprising a codon-optimized nucleotide sequence encoding a M-SmallCas9 polypeptide or variant thereof. In some embodiments, the exogenous nucleic acid can be under the control of (e.g., operably linked to) an unknown promoter (e.g. when the nucleic acid randomly integrates into a host cell genome) or can be under the control of (e.g., operably linked to) a known promoter. Suitable known promoters can be any known promoter and include constitutively active promoters (e.g. CMV promoter), inducible promoters (e.g. heat shock promoter, Tetracycline-regulated promoter, Steroid-regulated promoter, Metal-regulated promoter, estrogen receptor-regulated promoter, etc.), spatially restricted and/or temporally restricted promoters (e.g. a tissue specific promoter, a cell type specific promoter, etc.), etc.

Introducing Nucleic Acids into a Host Cell

In some embodiments, the methods of the disclosure include involve introducing into a host cell (or a population of host cells) one or more nucleic acids comprising a nucleotide sequence encoding a guide RNA and/or a codon-optimized nucleotide sequence encoding a M-SmallCas9 polypeptide or variant thereof. In some embodiments, a cell comprising a target DNA is in vitro. In some embodiments, a cell comprising a target DNA is in vivo. In some embodiments, the nucleotide sequence encoding a guide RNA and/or a M-SmallCas9 polypeptide or variant thereof is operably linked to an inducible promoter. In some embodiments, a nucleotide sequence encoding a guide RNA and/or a M-SmallCas9 polypeptide or variant thereof is operably linked to a constitutive promoter.

A guide RNA, or a nucleic acid comprising a nucleotide sequence encoding same, can be introduced into a host cell by any of a variety of well-known methods. Similarly, where a method involves introducing into a host cell a nucleic acid comprising a codon-optimized nucleotide sequence encoding a M-SmallCas9 polypeptide or variant thereof, such a nucleic acid can be introduced into a host cell by any of a variety of well-known methods. Guide polynucleotides (RNA or DNA) and/or M-SmallCas9 polynucleotides (RNA or DNA) can be delivered by viral or non-viral delivery vehicles known in the art.

Methods of introducing a nucleic acid into a host cell are known in the art, and any known method can be used to introduce a nucleic acid (e.g. an expression construct) into a stem cell or progenitor cell. Suitable methods include, e.g. viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g. Panyam et., al Adv Drug Deliv Rev. 2012 Sep. 13. pii: 50169-409X (12) 00283-9. doi: 10.1016/j.addr.2012.09.023), and the like, including but not limiting to exosome delivery.

Polynucleotides may be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18:1127-1133 (2011) (which focuses on non-viral delivery vehicles for siRNA that are also useful for delivery of other polynucleotides).

Suitable systems and techniques for delivering a nucleic acid of the disclosure (e.g., mRNA and sgRNA) for gene editing is include lipid nanoparticles (LNPs). As used herein, the term "lipid nanoparticles" includes liposomes irrespective of their lamellarity, shape or structure and lipoplexes as described for the introduction of nucleic acids and/or polypeptides into cells. These lipid nanoparticles can be complexed with biologically active compounds (e.g., nucleic acids and/or polypeptides) and are useful as in vivo delivery vehicles. In general, any method known in the art can be applied to prepare the lipid nanoparticles comprising one or more nucleic acids of the present disclosure and to prepare complexes of biologically active compounds and said lipid nanoparticles. Examples of such methods are widely disclosed, e.g. in Biochim Biophys Acta 1979, 557:9; Biochim et Biophys Acta 1980, 601:559; Liposomes: A practical approach (Oxford University Press, 1990); Pharmaceutica Acta Helvetiae 1995, 70:95; Current Science 1995, 68:715; Pakistan Journal of Pharmaceutical Sciences 1996, 19:65; Methods in Enzymology 2009, 464:343). Particularly suitable systems and techniques for preparing LNP formulations comprising one or more nucleic acids and/or polypeptides of the present disclosure include, but are not limited to, those developed by Intellia (see e.g., WO2017173054A1), Alnylam (see, e.g., WO2014008334A1), Modernatx (see., e.g., WO2017070622A1 and WO2017099823A1), TranslateBio, Acuitas (see, e.g., WO2018081480A1), Genevant Sciences, Arbutus Biopharma, Tekmira, Arcturus, Merck (see, e.g., WO2015130584A2), Novartis (see, e.g., WO2015095340A1), and Dicerna; all of which are herein incorporated by reference in their entireties.

Suitable nucleic acids comprising nucleotide sequences encoding a guide RNA and/or a M-SmallCas9 polypeptide or variant thereof include expression vectors, where an expression vector comprising a nucleotide sequence encoding a guide. In some embodiments, the expression vector is a viral construct, e.g. a recombinant adeno-associated virus construct (see, e.g. U.S. Pat. No. 7,078,387), a recombinant adenoviral construct, a recombinant lentiviral construct, a recombinant retroviral construct, etc. Suitable expression vectors include, but are not limited to, viral vectors (e.g. viral vectors based on vaccinia virus; poliovirus; adenovirus (see, e.g. Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:10881097, 1999; WO 94/12649, WO 93/03769; WO 93/19191; WO 94/28938; WO 95/11984 and WO 95/00655); adeno-associated virus (see, e.g. Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683-690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Viral. (1988) 166:154-165; and Flotte et al., PNAS (1993) 90:10613-10617); SV40; herpes simplex virus; human immunodeficiency virus (see, e.g. Miyoshi et al., PNAS 94:10319 23, 1997; Takahashi et al., J Virol 73:7812 7816, 1999); a retroviral vector (e.g. Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

A recombinant adeno-associated virus (AAV) vector may be used for delivery. Known techniques to produce rAAV particles in the art is to provide a cell with a polynucleotide to be delivered between two AAV invert terminal repeats (ITRs), AAV rep and cap genes and helper virus functions. Production of rAAV requires that the following components are present within a single cell (denoted herein as a packaging cell): a polynucleotide of interest between two ITRs, AAV rep and cap genes separate from (i.e., not in) the AAV genome, and helper virus functions. The AAV rep and cap genes may be from any AAV serotype for which recombinant virus can be derived and may be from a different serotype of AAV than that of ITRs on a packaged polynucleotide, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh.74. Production of pseudotyped rAAV is disclosed in, for example, WO 01/83692.

| AAV Serotype | Genbank Accession No. |
|---|---|
| AAV-1 | NC_002077.1 |
| AAV-2 | NC_001401.2 |
| AAV-3 | NC_001729.1 |
| AAV-38 | AF028705.1 |
| AAV-4 | NC_001829.1 |
| AAV-5 | NC_006152.1 |
| AAV-6 | AF028704.1 |
| AAV-7 | NC_006260.1 |
| AAV-8 | NC_006261.1 |
| AAV-9 | AX753250.1 |
| AAV-10 | AY631965.1 |
| AAV-11 | AY631966.1 |
| AAV-12 | 00813647.1 |
| AAV-13 | EU285562.1 |

A method of generating a packaging cell is to create a cell line that stably expresses all the necessary components for AAV particle production. For example, a plasmid (or multiple plasmids) comprising a polynucleotide of interest between AAV ITRs, AAV rep and cap genes separate from the AAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. Sci. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Bioi. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial, and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); Mclaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes used for transduction are dependent on target cell types. For example, the following exemplary cell types are known to be transduced by the indicated AAV serotypes among others.

| Tissue/Cell Type | Serotype |
|---|---|
| Liver | AAV8, AAV9 |
| Skeletal muscle | AAV1, AAV7, AAV6, AAV8, AAV9 |
| Central nervous system | AAV5, AAV1, AAV4 |
| RPE | AAV5, AAV4 |
| Photoreceptor cells | AAV5 |
| Lung | AAV9 |
| Heart | AAV8 |
| Pancreas | AAV8 |
| Kidney | AAV2 |

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g. Bitter et al. (1987) Methods in Enzymology, 153:516-544).

In some embodiments, a guide RNA and/or a M-SmallCas9 polypeptide or variant thereof can be provided as RNA. In such cases, the guide RNA and/or the RNA encoding the M-SmallCas9 polypeptide or variant thereof can be produced by direct chemical synthesis or may be transcribed in vitro from a DNA encoding the guide RNA. Methods of synthesizing RNA from a DNA template are well known in the art. In some embodiments, the guide RNA and/or the RNA encoding the M-SmallCas9 polypeptide or variant thereof will be synthesized in vitro using an RNA polymerase enzyme (e.g. T7 polymerase, T3 polymerase, SP6 polymerase, etc.). Once synthesized, the RNA may directly contact a target DNA or may be introduced into a cell by any of the well-known techniques for introducing nucleic acids into cells (e.g. microinjection, electroporation, transfection, etc.).

Nucleotides encoding a guide RNA (introduced either as DNA or RNA) and/or a M-SmallCas9 polypeptide or variant thereof (introduced as DNA or RNA) and/or a donor polynucleotide may be provided to the cells using well-developed transfection techniques; see, e.g. Angel and Yanik (2010) PLOS ONE 5(7): e 11756, and the commercially available TransMessenger® reagents from Qiagen, Stemfect™ RNA Transfection Kit from Stemgent, and TransiT®-mRNA Transfection Kit from Mims Bio. See also Beumer et al. (2008) Efficient gene targeting in *Drosophila* by direct embryo injection with zinc-finger nucleases. PNAS 105 (50): 19821-19826. In addition or alternatively, nucleic acids encoding a guide RNA and/or a M-SmallCas9 polypeptide or variant thereof and/or a M-SmallCas9 fusion polypeptide or variant thereof and/or a donor polynucleotide may be provided on DNA vectors. Many vectors, e.g., plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the cells. In other words, the cells are contacted with vectors comprising the nucleic acid encoding guide RNA and/or a M-SmallCas9 polypeptide or variant thereof and/or a M-SmallCas9 fusion polypeptide or variant thereof and/or a donor polynucleotide such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a guide RNA and/or a M-SmallCas9 polypeptide or variant thereof and/or a M-SmallCas9 fusion polypeptide or variant thereof and/or a donor polynucleotide. Retroviruses, for example, lentiviruses, are particularly suitable to the method of the present disclosure. Commonly used retroviral vectors are "defective", e.g., unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also be introduced by direct micro-injection (e.g. injection of RNA into a zebrafish embryo).

Vectors used for providing the nucleic acids encoding guide RNA and/or a M-SmallCas9 polypeptide or variant thereof and/or a M-SmallCas9 fusion polypeptide or variant thereof and/or a donor polynucleotide to the cells will generally comprise suitable promoters for driving the expression, that is, transcriptional activation, of the nucleic acid of interest. In other words, the nucleic acid of interest will be operably linked to a promoter. This may include ubiquitously active promoters, for example, the CMV-13-actin promoter, or inducible promoters, such as promoters that are active in particular cell populations or that respond to the presence of drugs such as tetracycline. By transcriptional activation, it is intended that transcription will be increased above basal levels in the target cell by at least 10 fold, by at least 100 fold, more typically by at least 1000 fold. In addition, vectors used for providing a guide RNA and/or a M-SmallCas9 polypeptide or variant thereof and/or a M-SmallCas9 fusion polypeptide or variant thereof and/or a donor polynucleotide to the cells may include nucleic acid sequences that code for selectable markers in the target cells, so as to identify cells that have taken up the guide RNA and/or a M-SmallCas9 polypeptide or variant thereof and/or a M-SmallCas9 fusion polypeptide or variant thereof and/or a donor polynucleotide.

A guide RNA and/or a M-SmallCas9 polypeptide or variant thereof and/or a M-SmallCas9 fusion polypeptide or variant thereof may instead be used to contact DNA or introduced into cells as RNA. Methods of introducing RNA into cells are known in the art and may include, for example, direct injection, transfection, or any other method used for the introduction of DNA. A M-SmallCas9 polypeptide or variant thereof may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, the M-SmallCas9 polypeptide or variant thereof may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (this sequence is not a disclosure under this patent application). As another example, the permeant peptide comprises the HIV-1 tat basic region amino acid sequence, which may include, for example, amino acids 49-57 of naturally occurring tat protein.

Other permeant domains include poly-arginine motifs, for example, the region of amino acids 34-56 of HIV-1 rev protein, nona-arginine, acta-arginine, and the like. (See, for example, Futaki et al. (2003) Curr Protein Pept Sci. 2003 April; 4 (2): 87-9 and 446; and Wender et al. (2000) Proc. Natl. Acad. Sci. U.S.A. 2000 Nov. 21; 97 (24): 13003-8; published US Patent Application Publications Nos. 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site may be determined by routine experimentation. In some embodiments the polypeptide permeant domain is chemically modified in order to increase the bioavailability of the PTD. Exemplary modifications are disclosed in Expert Opin Drug Deliv. 2009 November; 6 (11): 1195-205.

Generally, an effective amount of the guide RNA and/or M-SmallCas9 polypeptide or variant thereof and/or donor polynucleotide is provided to the target DNA or cells to induce targeted modification. An effective amount of the guide RNA and/or M-SmallCas9 polypeptide or variant thereof and/or donor polynucleotide is the amount to induce a 2-fold increase or more in the amount of targeted modification observed with the gRNA relative to a negative control, e.g., a cell contacted with an empty vector or irrelevant polypeptide. That is to say, an effective amount or dose of the guide RNA and/or M-SmallCas9 polypeptide or variant thereof and/or donor polynucleotide will induce a 2-fold increase, a 3-fold increase, a 4-fold increase or more in the amount of target modification observed at a target DNA region, in some embodiments a 5-fold increase, a 6-fold increase or more, sometimes a 7-fold or 8-fold increase or more in the amount of recombination observed, e.g., an increase of 10-fold, 50-fold, or 100-fold or more, in some embodiments, an increase of 200-fold, 500-fold, 700-fold, or 1000-fold or more, e.g., a 5000-fold, or 10,000-fold increase in the amount of recombination observed. The amount of target modification may be measured by any suitable method. For example, a split reporter construct comprising complementary sequence to the spacer of the guide RNA flanked by homologous sequences that, when recombined, will reconstitute a nucleic acid encoding an active reporter may be cotransfected into the cells, and the amount of reporter protein assessed after contact with the guide RNA and/or M-SmallCas9 polypeptide or variant thereof and/or donor polynucleotide, e.g. 2 hours, 4 hours, 8 hours, 12 hours, 24 hours, 36 hours, 48 hours, 72 hours or more after contact with the guide RNA and/or M-SmallCas9 polypeptide or variant thereof and/or donor polynucleotide. As another, more sensitivity assay, for example, the extent of recombination at a genomic DNA region of interest comprising target DNA sequences may be assessed by PCR or Southern hybridization of the region after contact with a guide RNA and/or M-SmallCas9 polypeptide or variant thereof and/or donor polynucleotide, e.g. 2 hours, 4 hours, 8 hours, 12 hours, 24 hours, 36 hours, 48 hours, 72 hours or more after contact with the guide RNA and/or M-SmallCas9 polypeptide or variant thereof and/or donor polynucleotide.

Contacting the cells with a guide RNA and/or M-SmallCas9 polypeptide or variant thereof and/or donor polynucleotide may occur in any culture media and under any culture conditions that promote the survival of the cells. For example, cells may be suspended in any appropriate nutrient medium that is suitable, such as Iscove's modified DMEM or RPMI1640, supplemented with fetal calf serum or heat inactivated fetal bovine serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are generally permissive of nonhomologous end joining and homology-directed repair. In applications in which it is desirable to insert a polynucleotide sequence into a target DNA sequence, a polynucleotide comprising a donor sequence to be inserted is also provided to the cell. By a "donor sequence" or "donor polynucleotide" it is meant a nucleic acid sequence to be inserted at the cleavage site induced by a M-SmallCas9 polypeptide or variant thereof. The donor polynucleotide will contain sufficient sequence homology to the flanking genomic regions of the cleavage site, e.g. 70%, 80%, 85%, 90%, 95%, or 100% sequence identity with the nucleotide sequences flanking the cleavage site, e.g. within about 50 bases or less of the cleavage site, e.g. within about 30 bases, within about 15 bases, within about 10 bases, within about 5 bases, or immediately flanking the cleavage site, to support homology-directed repair between it and the genomic sequence to which it bears homology. Approximately 25, 50, 100, or 200 nucleotides, or more than 200 nucleotides, of homologous sequences between a donor and a genomic sequence (or any integral value between 10 and 200 nucleotides, or more) will support homology-directed repair. Donor sequences can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is generally not identical to the genomic sequence that it replaces. Rather, the donor sequence may contain at least one or more single base substitutions, insertions, deletions, inversions or rearrangements with respect to the genomic sequence, so long as sufficient sequence identity is present to support homology-directed repair. In some embodiments, the donor sequence comprises a non-homologous sequence flanked by two regions homologous to the target DNA region (also referred to as homology arms), such that homology-directed repair between the target DNA region and the two flanking homology arms results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide. The donor sequence may comprise certain sequence differences as compared to the genomic sequence, e.g. restriction sites, nucleotide polymorphisms, selectable markers (e.g. drug resistance genes, fluorescent proteins, enzymes etc.), etc., which may be used to assess for successful insertion of the donor sequence at the cleavage site or in some cases may be used for other purposes (e.g. to signify expression at the targeted genomic locus). In some embodiments, if located in a coding region, such nucleotide sequence differences will not change the amino acid sequence, or will make amino acid changes which do not substantially affect the structure or function of the protein. Alternatively, these sequences differences may include flanking recombination sequences such as FLPs, IoxP sequences, or the like, that can be activated at a later time for removal of the marker sequence.

The donor sequence may be provided to the cell as single-stranded DNA, single-stranded RNA, double-stranded DNA, or double-stranded RNA. It may be introduced into a cell in linear or circular form. If introduced in linear form, the ends of the donor sequence may be protected (e.g. from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) Proc. Natl. Acad. Sci. USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the homology arms that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked (e.g. unmodified) nucleic acid, as nucleic acid complexed with an agent such as a liposome or poloxamer, or can be delivered by viruses (e.g. adenovirus, AAV), as described above for nucleic acids encoding a guide RNA and/or M-SmallCas9 polypeptide or variant thereof and/or donor polynucleotide.

Following the methods described above, a DNA region of interest may be cleaved and modified, e.g., "genetically modified", ex vivo. In some embodiments, as when a selectable marker has been inserted into the DNA region of interest, the population of cells may be enriched for those comprising the genetic modification by separating the genetically modified cells from the remaining population. Prior to enriching, the "genetically modified" cells may make up only about 1% or more (e.g. 2% or more, 3% or more, 4% or more, 5% or more, 6% or more, 7% or more, 8% or more, 9% or more, 10% or more, 15% or more, or 20% or more) of the cellular population. Separation of "genetically modified" cells may be achieved by any suitable separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other suitable technique. Techniques providing accurate separation include fluorescence activated cell sorters, which can have varying degrees of sophistication. Such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells. Cell compositions that are highly enriched for cells comprising modified DNA are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. In addition or alternatively, the cells may be frozen at liquid nitrogen temperatures and stored for long periods of time, being thawed and capable of being reused. In such cases, the cells will generally be frozen in 10% dimethylsulfoxide (DMSO), 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro under various culture conditions. The cells may be expanded in culture, e.g., grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the respective cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Cells that have been genetically modified in this way may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals (e.g. mouse, rat, guinea pig, hamster, lagomorpha (e.g. rabbit), etc.) may be used for experimental investigations.

Cells may be provided to the subject alone or with a suitable substrate or matrix, e.g. to support their growth and/or organization in the tissue to which they are being transplanted. Generally, at least $1\times10^3$ cells will be administered, for example $5\times10^3$ cells, $1\times10^4$ cells, $5\times10^4$ cells, $1\times10^5$ cells, $1\times10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g., U.S. application No. 20070254842, incorporated herein by reference); or by implanting a device upon which the cells have been reversibly affixed (see e.g. U.S. application Nos. 20080081064 and 20090196903, incorporated herein by reference). Cells may also be introduced into an embryo (e.g. a blastocyst) for the purpose of generating a transgenic animal (e.g. a transgenic mouse)

In some embodiments, a nucleotide sequence encoding a guide RNA and/or a M-SmallCas9 polypeptide or variant thereof is operably linked to a control element, e.g. a transcriptional control element, such as a promoter. The transcriptional control element is generally functional in either a eukaryotic cell, such as a mammalian cell (e.g., human cell); or a prokaryotic cell (e.g. bacterial or archaeal cell). In some embodiments, a nucleotide sequence encoding a guide RNA and/or a M-SmallCas9 polypeptide or variant thereof is operably linked to multiple control elements that allow expression of the nucleotide sequence encoding a guide RNA and/or a M-SmallCas9 polypeptide or variant thereof in both prokaryotic and eukaryotic cells.

A promoter can be a constitutively active promoter (e.g., a promoter that is constitutively in an active "ON" state), it may be an inducible promoter (e.g., a promoter whose state, active/"ON" or inactive/"OFF", is controlled by an external stimulus, e.g. the presence of a particular temperature, compound, or protein.), it may be a spatially restricted promoter (e.g., transcriptional control element, enhancer, etc.) (e.g. tissue specific promoter, cell type specific promoter, etc.), and it may be a temporally restricted promoter (e.g., the promoter is in the "ON" state or "OFF" state during specific stages of embryonic development or during specific stages of a biological process, e.g. hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g. pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a Rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31 (17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter (e.g. Tet-ON, Tet-OFF, etc.), Steroid-regulated promoter, Metal-regulated promoter, estrogen receptor-regulated promoter, etc. Inducible promoters can therefore be regulated by molecules including, but not limited to, doxycycline; RNA polymerase, e.g. T7 RNA polymerase; an estrogen receptor; an estrogen receptor fusion; etc.

In some embodiments, the promoter is a spatially restricted promoter (e.g., cell type specific promoter, tissue specific promoter, etc.) such that in a multi-cellular organism, the promoter is active (e.g., "ON") in a subset of specific cells. Spatially restricted promoters may also be referred to as enhancers, transcriptional control elements, control sequences, etc. Any suitable spatially restricted promoter may be used and the choice of suitable promoter (e.g. a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a M-SmallCas9 polypeptide or variant thereof in a wide variety of different tissues and cell types, depending on the organism. Some spatially restricted promoters are also temporally restricted such that the promoter is in the "ON" state or "OFF" state during specific stages of embryonic development or during specific stages of a biological process (e.g. hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g. EMBL HSEN02, X51956); an aromatic amino acid decarboxylase (AADC) promoter; a neurofilament promoter (see, e.g. GenBank HUMNFL, L04147); a synapsin promoter (see, e.g. GenBank HUMSYNIB, M55301); a thy-1 promoter (see, e.g. Chen et al. (1987) Ce/151:7-19; and Llewellyn, et al. (2010) Nat. Med. 16 (10): 1161-1166); a serotonin receptor promoter (see, e.g. GenBank S62283); a tyrosine hydroxylase promoter (TH) (see, e.g. Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g. Radovick et al. (1991) Proc. Natl. Acad. Sci. USA 88:3402-3406); an L7 promoter (see, e.g. Oberdick et al. (1990) Science 248:223-226); a DNMT promoter (see, e.g. Bartge et al. (1988) Proc. Nat/. Acad. Sci. USA 85:3648-3652); an enkephalin promoter (see, e.g. Comb et al. (1988) EMBO J. 17:3793-3805); a myelin basic protein (MBP) promoter; a Ca2+-calmodulin-dependent protein kinase 11-alpha (CamKlla) promoter (see, e.g. Mayford et al. (1996) Proc. Nat/. Acad. Sci. USA 93:13250; and Casanova et al. (2001) Genesis 31:37); a CMV enhancer/platelet-derived growth factor-0 promoter (see, e.g. Liu et al. (2004) Gene Therapy 11:52-60); and the like.

Adipocyte-specific spatially restricted promoters include, but are not limited to aP2 gene promoter/enhancer, e.g. a region from −5.4 kb to +21 bp of a human aP2 gene (see, e.g. Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g. Knight et al. (2003) Proc. Nat/. Acad. Sci. USA 100:14725); a fatty acid translocase (FAT/CD36) promoter (see, e.g. Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g. Mason et al. (1998) Endocrinol. 139:1013; and Chen et al. (1999) Biochem. Biophys. Res. Comm. 262:187); an adiponectin promoter (see, e.g. Kita et al. (2005) Biochem. Biophys. Res. Comm. 331:484; and Chakrabarti (2010) Endocrinol. 151:2408); an adipsin promoter (see, e.g. Platt et al. (1989) Proc. Nat/. Acad. Sci. USA 86:7490); a resistin promoter (see, e.g. Seo et al. (2003) Malec. Endocrinol. 17:1522); and the like.

Cardiomyocyte-specific spatially restricted promoters include, but are not limited to control sequences derived from the following genes: myosin light chain-2, a-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22a promoter (see, e.g. Akyilrek et al. (2000) Mol. Med. 6:983; and U.S. Pat. No. 7,169,874); a smoothelin promoter (see, e.g. WO 2001/018048); an α-smooth muscle actin promoter; and the like. For example, a 0.4 kb region of the SM22a promoter, within which lie two CArG elements, has been shown to mediate vascular smooth muscle cell-specific expression (see, e.g. Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Compositions Comprising a Guide RNA

In some embodiments, provided herein is a composition comprising a guide RNA. The composition can comprise, in addition to the guide RNA, one or more of: a salt, e.g. NaCl, $MgCl_2$, KCl, $MgSO_4$, etc.; a buffering agent, e.g. a Tris buffer, N-(2-Hydroxyethyl) piperazine-N'-(2-ethanesulfonic acid) (HEPES), 2-(N-Morpholino) ethanesulfonic acid (MES), MES sodium salt, 3-(N-Morpholino) propanesulfonic acid (MOPS), N-tris [Hydroxymethyl]methyl-3-aminopropanesulfonic acid (TAPS), etc.; a solubilizing agent; a detergent, e.g. a non-ionic detergent such as Tween-20, etc.; a nuclease inhibitor; and the like. For example, in some embodiments, a composition comprises a guide RNA and a buffer for stabilizing nucleic acids.

In some embodiments, a guide RNA present in a composition is pure, e.g. at least 75%, at least 80%, at least 85%, at least 90%, at least 95%, at least 98%, at least 99%, or more than 99% pure, where "% purity" means that guide RNA is the recited percent free from other macromolecules, or contaminants that may be present during the production of the guide RNA.

Compositions Comprising a M-SmallCas9 Polypeptide

In some embodiments, provided herein is a composition comprising a M-SmallCas9 polypeptide or variant thereof expressed from a codon-optimized polynucleotide sequence. The composition can comprise, in addition to the M-SmallCas9 polypeptide or variant thereof, one or more of: a salt, e.g. NaCl, $MgCl_2$, KCl, $MgSO_4$, etc.; a buffering agent, e.g. a Tris buffer, HEPES, MES, MES sodium salt, MOPS, TAPS, etc.; a solubilizing agent; a detergent, e.g. a non-ionic detergent such as Tween-20, etc.; a protease inhibitor; a reducing agent (e.g. dithiothreitol); and the like.

In some embodiments, a M-SmallCas9 polypeptide or variant thereof present in a composition is pure, e.g. at least 75%, at least 80%, at least 85%, at least 90%, at least 95%, at least 98%, at least 99%, or more than 99% pure, where "% purity" means that the M-SmallCas9 polypeptide or variant thereof is the recited percent free from other proteins, other macromolecules, or contaminants that may be present during the production of the M-SmallCas9 polypeptide or variant thereof.

Compositions Comprising a Guide RNA and a Site-Directed Modifying Polypeptide

In some embodiments, provided herein is a composition comprising: (i) a guide RNA or a polynucleotide encoding the guide RNA; and ii) a nucleic acid comprising a codon-optimized polynucleotide sequence encoding a M-SmallCas9 polypeptide or variant thereof, or a M-SmallCas9 polypeptide or variant thereof expressed from the nucleic acid. In some embodiments, the M-SmallCas9 polypeptide or variant thereof exhibits enzymatic activity that modifies a target DNA. In some embodiments, the M-SmallCas9 polypeptide or variant thereof exhibits enzymatic activity that modifies a polypeptide encoded by a target DNA. In some embodiments, the M-SmallCas9 polypeptide or variant thereof modulates transcription from the target DNA.

In some embodiments, the components of the composition are individually pure, e.g. each of the components is at least 75%, at least 80%, at least 90%, at least 95%, at least 98%, at least 99%, or at least 99%, pure. In some embodiments, the individual components of a composition are pure before being added to the composition.

Kits

In some embodiments, a kit is provided for carrying out a method described herein. A kit can include one or more of: a M-SmallCas9 polypeptide or variant thereof expressed from, for example, a codon-optimized polynucleotide sequence; a guide RNA; a nucleic acid comprising a nucleotide sequence encoding a guide RNA. A kit can include a complex that includes two or more of: a M-SmallCas9 polypeptide or variant thereof; a nucleic acid comprising a nucleotide encoding a M-SmallCas9 polypeptide or variant thereof; a guide RNA; a nucleic acid comprising a nucleotide sequence encoding a guide RNA. In some embodiments, a kit includes a M-SmallCas9 polypeptide or variant thereof, or a polynucleotide encoding the same. In some embodiments, the activity portion of the M-SmallCas9 polypeptide or variant thereof exhibits reduced or inactivated nuclease activity. In some embodiments, the M-SmallCas9 polypeptide or variant thereof is a M-SmallCas9 fusion protein.

In some embodiments, a kit includes: (a) a nucleic acid comprising a codon-optimized polynucleotide sequence encoding a M-SmallCas9 polypeptide or variant thereof, or a M-SmallCas9 polypeptide or variant thereof expressed from the nucleic acid; and (b) a gRNA or nucleic acid encoding the gRNA, wherein the gRNA is capable of guiding the M-SmallCas9 polypeptide or variant thereof to a target polynucleotide sequence. In some embodiments, the kit comprises the nucleic acid comprising the codon-optimized polynucleotide sequence. A kit comprising a M-SmallCas9 polypeptide or variant thereof expressed from a codon-optimized polynucleotide sequence, or a nucleic acid comprising the codon-optimized polynucleotide sequence, can further include one or more additional reagents, where such additional reagents can be selected from: a buffer for introducing the M-SmallCas9 polypeptide or variant thereof into a cell; a wash buffer; a control reagent; a control expression vector or polyribonucleotide; a reagent for in vitro production of the M-SmallCas9 polypeptide or variant thereof from DNA, and the like.

In some embodiments of any of the kits described herein, the kit includes an sgRNA. In some embodiments, the kit includes two or more sgRNAs.

In some embodiments of any of the kits described herein, a gRNA (including, e.g., two or more guide RNAs) can be provided as an array (e.g. an array of RNA molecules, an array of DNA molecules encoding the guide RNA(s), etc.). Such kits can be useful, for example, for use in conjunction with the above described genetically modified host cells that include a M-SmallCas9 polypeptide or variant thereof.

In some embodiments of any of the kits described herein, the kit further includes a donor polynucleotide to effect the desired genetic modification.

Components of a kit can be in separate containers; or can be combined in a single container.

Any of the kits described herein can further include one or more additional reagents, where such additional reagents can be selected from: a dilution buffer; a reconstitution solution; a wash buffer; a control reagent; a control expression vector or Polyribonucleotide; a reagent for in vitro production of the M-SmallCas9 polypeptide or variant thereof from DNA, and the like.

In addition to above-mentioned components, a kit can further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or subpackaging) etc. In some embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods of The Disclosure

Methods of Modifying a Target DNA and/or a Polypeptide Encoded by a Target DNA

In some embodiments, provided herein are methods for modifying a target DNA and/or a polypeptide encoded by a target DNA. In some embodiments, the method involves providing (i) a nucleic acid encoding SEQ ID NO: 1 or a variant thereof having at least 90% sequence identity to SEQ ID NO: 1 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 2 or a variant thereof having at least 90% sequence identity to SEQ ID NO: 2 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 3 or a variant thereof having at least 90% sequence identity to SEQ ID NO: 3 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 4 or a variant thereof having at least 90% sequence identity to SEQ ID NO: 4 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 5 or a variant thereof having at least 90% sequence identity to SEQ ID NO: 5 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 6 or a variant thereof having at least 90% sequence identity to SEQ ID NO: 6 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 7 or a variant thereof having at least 90% sequence identity to SEQ ID NO: 7 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 8 or a variant thereof having at least 90% sequence identity to SEQ ID NO: 8 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 9 or a variant thereof having at least 90% sequence identity to SEQ ID NO: 9 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, the method involves providing (i) a nucleic acid encoding SEQ ID NO: 133 or a variant thereof having at least 90% sequence identity to SEQ ID NO: 133 encoding a M-SmallCas9 polypeptide or variant thereof, or a M-SmallCas9 polypeptide or variant thereof expressed from the nucleic acid; and (ii) a gRNA or nucleic acid encoding the gRNA, wherein the gRNA is capable of guiding the M-SmallCas9 polypeptide or variant thereof to a target polynucleotide sequence, such that a complex (a "targeting complex") comprising the M-SmallCas9 polypeptide or variant thereof and the gRNA is formed and comes in contact with a target DNA comprising the target polynucleotide sequence.

In some embodiments, provided herein is a method of targeting, editing, modifying, or manipulating a target DNA at one or more locations in a cell or in vitro environment, comprising introducing into the cell or in vitro environment (a) a nucleic acid comprising e.g., a codon-optimized polynucleotide sequence encoding a M-SmallCas9 polypeptide or variant thereof, or a M-SmallCas9 polypeptide or variant thereof expressed from the nucleic acid; and (b) a gRNA or nucleic acid encoding the gRNA, wherein the gRNA is capable of guiding the M-SmallCas9 polypeptide or variant thereof to a target polynucleotide sequence in the target DNA. In some embodiments, the method comprises introducing into the cell or in vitro environment the nucleic acid comprising the codon-optimized polynucleotide sequence. In some embodiments, the method comprises introducing into the cell or in vitro environment the M-SmallCas9 polypeptide or variant thereof expressed from the nucleic acid. In some embodiments, the M-SmallCas9 polypeptide comprises (or consists of) the amino acid sequence of SEQ ID NOs: 1 to 9, or 133. In some embodiments, the method comprises introducing into the cell or in vitro environment the gRNA. In some embodiments, the method comprises introducing into the cell or in vitro environment nucleic acid encoding the gRNA. In some embodiments, the gRNA is a single guide RNA (sgRNA). In some embodiments, the method comprises introducing into the cell or in vitro environment one or more additional gRNAs or nucleic acid encoding the one or more additional gRNAs targeting the target DNA. In some embodiments, the method further comprises introducing into the cell or in vitro environment a donor template.

In some embodiments, provided herein is a method of targeting, editing, modifying, or manipulating a target DNA at one or more locations in a cell or in vitro environment, comprising introducing into the cell or in vitro environment (a) a nucleic acid encoding a M-SmallCas9 polypeptide or variant thereof, or a M-SmallCas9 polypeptide or variant thereof expressed from such a nucleic acid; and (b) a gRNA or nucleic acid encoding the gRNA, wherein the gRNA is capable of guiding the M-SmallCas9 polypeptide or variant thereof to a target polynucleotide sequence in the target DNA. In some embodiments, the method comprises introducing into the cell or in vitro environment the M-SmallCas9 polypeptide or variant thereof expressed from the nucleic acid. In some embodiments, the M-SmallCas9 polypeptide or variant thereof comprises the amino acid sequence of SEQ ID NOs: 1 to 9, or 133 or a variant thereof having at least 95% sequence identity to those amino acid sequences. In some embodiments, the method comprises introducing into the cell or in vitro environment the gRNA. In some embodiments, the method comprises introducing into the cell or in vitro environment nucleic acid encoding the gRNA. In some embodiments, the gRNA is a single guide RNA (sgRNA). In some embodiments, the method comprises introducing into the cell or in vitro environment one or more additional gRNAs or nucleic acid encoding the one or more additional gRNAs targeting the target DNA. In some embodiments, the method further comprises introducing into the cell or in vitro environment a donor template.

As discussed above, a gRNA or sgRNA and a M-SmallCas9 polypeptide or variant thereof may form a ribonucleoprotein complex. The guide RNA provides target specificity to the complex by including a nucleotide sequence that is complementary to a sequence of a target DNA. The M-SmallCas9 polypeptide or variant thereof of the complex provides the endonuclease activity. In some embodiments, a complex modifies a target DNA, leading to, for example, DNA cleavage, DNA methylation, DNA damage, DNA repair, etc. In some embodiments, a complex modifies a target polypeptide associated with target DNA (e.g. a histone, a DNA-binding protein, etc.), leading to, for example, histone methylation, histone acetylation, histone ubiquitination, and the like. The target DNA may be, for example, naked (e.g. unbound by DNA associated proteins) DNA in vitro, chromosomal DNA in cells in vitro, chromosomal DNA in cells in vivo, etc.

The nuclease activity of a M-SmallCas9 polypeptide or variant thereof described herein may cleave target DNA to produce double strand breaks. These breaks are then repaired by the cell in one of two ways: non-homologous end joining, and homology-directed repair. In non-homologous end joining (NHEJ), the double-strand breaks are repaired by direct ligation of the break ends to one another. In the process a few base pairs can be inserted or deleted at the cleavage site. In homology-directed repair, a donor polynucleotide with homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. In some embodiments, a target DNA is contacted with a donor polynucleotide. In some embodiments, a donor polynucleotide is introduced into a cell. The modifications of the target DNA due to NHEJ and/or homology-directed repair lead to, for example, gene correction, gene replacement, gene tagging, transgene insertion, nucleotide deletion, nucleotide insertion, gene disruption, gene mutation, sequence replacement, etc. Accordingly, cleavage of DNA by a M-SmallCas9 polypeptide or variant thereof may be used to delete nucleic acid material from a target DNA sequence (e.g. to disrupt a gene that makes cells susceptible to infection (e.g. the CCRS or CXCR4 gene, which makes T cells susceptible to HIV infection, to remove disease-causing trinucleotide repeat sequences in neurons, to create gene knockouts and mutations as disease models in research, etc.) by cleaving the target DNA sequence and allowing the cell to repair the sequence in the absence of an exogenously provided donor polynucleotide. Thus, the methods can be used to knock out a gene (resulting in complete lack of transcription/translation or altered transcription/translation) or to knock in genetic material into a locus of choice in the target DNA In addition or alternatively, if a guide RNA and a M-SmallCas9 polypeptide or variant thereof are co-administered to cells with a donor polynucleotide sequence that includes at least a segment with homology to the target DNA sequence, the subject methods may be used to add, e.g., insert or replace, nucleic acid material to a target DNA sequence (e.g. to “knock in” a nucleic acid that encodes for a protein, an siRNA, an miRNA, etc.), to add a tag (e.g. 6×His, a fluorescent protein (e.g. a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g. introduce a mutation), and the like. As such, a complex comprising a guide RNA and a M-SmallCas9 polypeptide or variant thereof is useful in any in vitro or in vivo application in which it is desirable to modify DNA in a site-specific, e.g., “targeted”, way, for example gene knock-out, gene knock-in, gene editing, gene tagging, sequence replacement, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In some embodiments, the methods described herein employ a M-SmallCas9 polypeptide or variant thereof including a heterologous sequence (e.g. a M-SmallCas9 fusion polypeptide). In some embodiments, a heterologous sequence can provide for subcellular localization of the M-SmallCas9 polypeptide or variant thereof (e.g. a nuclear localization signal (NLS) for targeting to the nucleus; a mitochondrial localization signal for targeting to the mitochondria; a chloroplast localization signal for targeting to a chloroplast; an ER retention signal; and the like). In some embodiments, a heterologous sequence can provide a tag for ease of tracking or purification (e.g. a fluorescent protein, e.g. green fluorescent protein (GFP), YFP, RFP, CFP, mCherry, tdTomato, and the like; a histidine tag, e.g. a 6×His tag; a hemagglutinin (HA) tag; a FLAG tag; a Myc tag; and the like). In some embodiments, the heterologous sequence can provide for increased or decreased stability.

In some embodiments, the methods described herein employ a guide RNA and a M-SmallCas9 polypeptide or variant thereof used as an inducible system for shutting off gene expression in target cells. In some embodiments, nucleic acids encoding an appropriate guide RNA and/or an appropriate M-SmallCas9 polypeptide or variant thereof are incorporated into the chromosome of a target cell and are under control of an inducible promoter. When the guide RNA and/or the M-SmallCas9 polypeptide or variant thereof are induced, the target DNA is cleaved (or otherwise modified) at the location of interest (e.g. a target gene on a separate plasmid), when both the guide RNA and the M-SmallCas9 polypeptide or variant thereof are present and form a complex. As such, in some embodiments, target cells are engineered to include nucleic acid sequences encoding an appropriate M-SmallCas9 polypeptide or variant thereof in the genome and/or an appropriate guide RNA on a plasmid (e.g. under control of an inducible promoter), allowing experiments in which the expression of any targeted gene (expressed from a separate plasmid introduced into the strain) could be controlled by inducing expression of the guide RNA and the M-SmallCas9 polypeptide or variant thereof. In some embodiments, the M-SmallCas9 polypeptide or variant thereof has enzymatic activity that modifies target DNA in ways other than introducing double strand breaks. Enzymatic activity of interest that may be used to modify target DNA (e.g. by fusing a heterologous polypeptide with enzymatic activity to a M-SmallCas9 polypeptide or variant thereof, thereby generating a M-SmallCas9 fusion polypeptide or variant thereof) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). Methylation and demethylation is recognized in the art as an important mode of epigenetic gene regulation while repair of DNA damage is essential for cell survival and for proper genome maintenance in response to environmental stresses. As such, the methods herein find use in the epigenetic modification of target DNA and may be employed to control epigenetic modification of target DNA at any location in a target DNA by introducing the desired sequence into the spacer region of a guide RNA. The methods herein also find use in the intentional and controlled damage of DNA at any desired location within the target DNA. The methods herein also find use in the sequence-specific and controlled repair of DNA at any desired location within the target DNA. Methods to target DNA-modifying enzymatic activities to specific locations in target DNA find use in both research and clinical applications.

In some embodiments, multiple guide RNAs are used to simultaneously modify different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

In some embodiments, the M-SmallCas9 polypeptide or variant thereof is provided directly as a protein. As one non-limiting example, fungi (e.g. yeast) can be transformed with exogenous protein and/or nucleic acid using spheroplast transformation (see Kawai et al., Bioeng Bugs. 2010 November-December; 1 (6): 395-403: 'Transformation of *Saccharomyces cerevisiae* and other fungi: methods and possible underlying mechanism"; and Tanka et al., Nature. 2004 Mar. 18; 428 (6980): 323-8: "Conformational variations in an infectious protein determine prion strain differences"; both of which are herein incorporated by reference in their entirety). Thus, a M-SmallCas9 polypeptide or variant thereof can be incorporated into a spheroplast (with or without nucleic acid encoding a guide RNA and with or without a donor polynucleotide) and the spheroplast can be used to introduce the content into a yeast cell. A M-SmallCas9 polypeptide or variant thereof can be introduced into a cell (provided to the cell) by any suitable method; such methods are known to those of ordinary skill in the art. As another non-limiting example, a M-SmallCas9 polypeptide or variant thereof can be injected directly into a cell (e.g. with or without nucleic acid encoding a guide RNA and with or without a donor polynucleotide), e.g. a cell of a zebrafish embryo, the pronucleus of a fertilized mouse oocyte, etc.

Methods of Modulating Transcription

In some embodiments, provided herein are methods of modulating transcription of a target nucleic acid in a host cell. The methods generally involve contacting the target nucleic acid with an enzymatically inactive M-SmallCas9 polypeptide and a guide RNA. The methods are useful in a variety of applications, which are also provided.

A transcriptional modulation method of the present disclosure overcomes some of the drawbacks of methods involving RNAi. A transcriptional modulation method of the present disclosure finds use in a wide variety of applications, including research applications, drug discovery (e.g. high throughput screening), target validation, industrial applications (e.g. crop engineering; microbial engineering, etc.), diagnostic applications, therapeutic applications, and imaging techniques.

In some embodiments, provided herein is a method of selectively modulating transcription of a target DNA in a host cell, e.g., a human cell. The method generally involves: a) introducing into the host cell: i) a guide RNA, or a nucleic acid comprising a nucleotide sequence encoding the guide RNA; and ii) a M-SmallCas9 polypeptide or variant thereof, or a nucleic acid comprising a nucleotide sequence encoding the M-SmallCas9 polypeptide or variant thereof, where the M-SmallCas9 polypeptide or variant thereof exhibits reduced endodeoxyribonuclease activity. The guide RNA and the M-SmallCas9 polypeptide or variant thereof form a complex in the host cell; the complex selectively modulates transcription of a target DNA in the host cell.

In some embodiments, the methods described herein employ a modified form of the M-SmallCas9 protein. In some embodiments, the modified form of the M-SmallCas9 protein includes an amino acid change (e.g. deletion, insertion, or substitution) that reduces the nuclease activity of the M-SmallCas9 protein. For example, in some embodiments, the modified form of the M-SmallCas9 protein has less than 50%, less than 40%, less than 30%, less than 20%, less than 10%, less than 5%, or less than 1% of the nuclease activity of the corresponding unmodified M-SmallCas9 polypeptide. In some embodiments, the modified form of the M-SmallCas9 polypeptide has no substantial nuclease activity. When a M-SmallCas9 polypeptide or variant thereof is a modified form of the M-SmallCas9 polypeptide that has no substantial nuclease activity, it can be referred to as "dM-SmallCas9."

In some embodiments, a transcription modulation method described herein allows for selective modulation (e.g. reduction or increase) of a target nucleic acid in a host cell. For example, "selective" reduction of transcription of a target nucleic acid reduces transcription of the target nucleic acid by at least 10%, at least 20%, at least 30%, at least 40%, at least 50%, at least 60%, at least 70%, at least 80%, at least 90%, or greater than 90%, compared to the level of transcription of the target nucleic acid in the absence of a guide RNA/M-SmallCas9 polypeptide or variant thereof complex. Selective reduction of transcription of a target nucleic acid reduces transcription of the target nucleic acid, but does not substantially reduce transcription of a non-target nucleic acid, e.g. transcription of a non-target nucleic acid is reduced, if at all, by less than 10% compared to the level of transcription of the non-target nucleic acid in the absence of the guide RNA/M-SmallCas9 polypeptide or variant thereof complex.

In some embodiments, the M-SmallCas9 polypeptide or variant thereof has activity that modulates the transcription of target DNA (e.g. in the case of a M-SmallCas9 fusion polypeptide or variant thereof, etc.). In some embodiments, a M-SmallCas9 fusion polypeptide or variant thereof comprising a heterologous polypeptide that exhibits the ability to increase or decrease transcription (e.g. transcriptional activator or transcription repressor polypeptides) is used to increase or decrease the transcription of target DNA at a specific location in a target DNA, which is guided by the spacer of the guide RNA. Examples of source polypeptides for providing a M-SmallCas9 fusion polypeptide or variant thereof with transcription modulatory activity include, but are not limited to light-inducible transcription regulators, small molecule/drug-responsive transcription regulators, transcription factors, transcription repressors, etc. In some embodiments, the method is used to control the transcription of a targeted gene-coding RNA (protein-encoding mRNA) and/or a targeted non-coding RNA (e.g. tRNA, rRNA, snoRNA, siRNA, miRNA, long ncRNA, etc.). In some embodiments, the M-SmallCas9 polypeptide or variant thereof has enzymatic activity that modifies a polypeptide associated with DNA (e.g. histone). In some embodiments, the enzymatic activity is methyltransferase activity, demethylase activity, acetyltransferase activity, deacetylase activity, kinase activity, phosphatase activity, ubiquitin ligase activity (e.g., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g. from GlcNAc transferase) or deglycosylation activity. The enzymatic activities listed herein catalyze covalent modifications to proteins. Such modifications are known in the art to alter the stability or activity of the target protein (e.g. phosphorylation due to kinase activity can stimulate or silence protein activity depending on the target protein). Of particular interest as protein targets are histones. Histone proteins are known in the art to bind DNA and form complexes known as nucleosomes. Histones can be modified (e.g. by methylation, acetylation, ubiquitination, phosphorylation) to elicit structural changes in the surrounding DNA, thus controlling the accessibility of potentially large portions of DNA to interacting factors such as transcription factors, polymerases and the like. A single histone can be modified in many different ways and in many different combinations (e.g. trimethylation of lysine 27 of histone 3, H3K27, is associated with DNA regions of repressed transcription while trimethylation of lysine 4 of histone 3, H3K4, is associated with DNA regions of active transcription). Thus, a M-SmallCas9 fusion polypeptide or variant thereof with histone-modifying activity finds use in the site specific control of chromosomal structure and can be used to alter the histone modification pattern in a selected region of target DNA. Such methods find use in both research and clinical applications.

Increased Transcription

"Selective" increased transcription of a target DNA can increase transcription from the target DNA by at least 1.1 fold (e.g. at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.5 fold, at least 3 fold, at least 3.5 fold, at least 4 fold, at least 4.5 fold, at least 5 fold, at least 6 fold, at least 7 fold, at least 8 fold, at least 9 fold, at least 10 fold, at least 12 fold, at least 15 fold, or at least 20-fold) compared to the level of transcription from the target DNA in the absence of a guide RNA/M-SmallCas9 polypeptide or variant thereof complex. Selective increase of transcription of a target DNA increases transcription from the target DNA, but does not substantially increase transcription of a non-target DNA, e.g. transcription of a non-target DNA is increased, if at all, by less than about 5-fold (e.g. less than about 4-fold, less than about 3-fold, less than about 2-fold, less than about 1.8-fold, less than about 1.6-fold, less than about 1.4-fold, less than about 1.2-fold, or less than about 1.1-fold) compared to the level of transcription of the non-targeted DNA in the absence of the guide RNA/M-SmallCas9 polypeptide or variant thereof complex.

As a non-limiting example, increased transcription can be achieved by fusing dM-SmallCas9 to a heterologous sequence. Suitable fusion partners include, but are not limited to, a polypeptide that provides an activity that indirectly increases transcription by acting directly on the target DNA or on a polypeptide (e.g. a histone or other DNA-binding protein) associated with the target DNA. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, crotonylation, decrotonylation, propionylation, depropionylation, myristoylation activity, or demyristoylation activity.

Additional suitable fusion partners include, but are not limited to, a polypeptide that directly provides for increased transcription of the target nucleic acid (e.g. a transcription activator or a fragment thereof, a protein or fragment thereof that recruits a transcription activator, a small molecule/drug-responsive transcription regulator, etc.).

A non-limiting example of a method using a dM-SmallCas9 fusion protein to increase transcription in a prokaryote includes a modification of the bacterial one-hybrid (B1H) or two-hybrid (B2H) system. In the B1H system, a DNA binding domain (BD) is fused to a bacterial transcription activation domain (AD, e.g. the alpha subunit of the *Escherichia coli* RNA polymerase (RNAPa)). Thus, a dM-SmallCas9 can be fused to a heterologous sequence comprising an AD. When the dM-SmallCas9 fusion protein arrives at the upstream region of a promoter (targeted there by the guide RNA) the AD (e.g. RNAPa) of the dM-SmallCas9 fusion protein recruits the RNAP holoenzyme, leading to transcription activation. In the B2H system, the BD is not directly fused to the AD; instead, their interaction is mediated by a protein-protein interaction (e.g. GAL11P-GAL4 interaction). To modify such a system for use in the methods, dM-SmallCas9 can be fused to a first protein sequence that provides for protein-protein interaction (e.g. the yeast GAL11P and/or GAL4 protein) and RNAa can be fused to a second protein sequence that completes the protein-protein interaction (e.g. GAL4 if GAL11P is fused to dM-SmallCas9, GAL11P if GAL4 is fused to dM-SmallCas9, etc.). The binding affinity between GAL11P and GAL4 increases the efficiency of binding and transcription firing rate.

A non-limiting example of a method using a dM-SmallCas9 fusion protein to increase transcription in eukaryotes includes fusion of dM-SmallCas9 to an activation domain (AD) (e.g. GAL4, herpesvirus activation protein VP16 or VP64, human nuclear factor NF-κB p65 subunit, etc.). To render the system inducible, expression of the dM-SmallCas9 fusion protein can be controlled by an inducible promoter (e.g. Tet-ON, Tet-OFF, etc.). The guide RNA can be designed to target known transcription response elements (e.g. promoters, enhancers, etc.), known upstream activating sequences (UAS), sequences of unknown or known function that are suspected of being able to control expression of the target DNA, etc.

Additional Fusion Partners

Non-limiting examples of fusion partners to accomplish increased or decreased transcription include, but are not limited to, transcription activator and transcription repressor domains (e.g. the Krüppel associated box (KRAB or SKD); the Mad mSIN3 interaction domain (SID); the ERF repressor domain (ERD), etc.). In some such cases, the dM-SmallCas9 fusion protein is targeted by the guide RNA to a specific location (e.g., sequence) in the target DNA and exerts locus-specific regulation such as blocking RNA polymerase binding to a promoter (which selectively inhibits transcription activator function), and/or modifying the local chromatin status (e.g. when a fusion sequence is used that modifies the target DNA or modifies a polypeptide associated with the target DNA). In some embodiments, the changes are transient (e.g. transcription repression or activation). In some embodiments, the changes are inheritable (e.g. when epigenetic modifications are made to the target DNA or to proteins associated with the target DNA, e.g. nucleosomal histones). In some embodiments, the heterologous sequence can be fused to the C-terminus of the dM-SmallCas9 polypeptide. In some embodiments, the heterologous sequence can be fused to the N-terminus of the dM-SmallCas9 polypeptide. In some embodiments, the heterologous sequence can be fused to an internal portion (e.g., a portion other than the N- or C-terminus) of the dM-SmallCas9 polypeptide. The biological effects of a method using a dM-SmallCas9 fusion protein can be detected by any suitable method (e.g. gene expression assays; chromatin-based assays, e.g. Chromatin ImmunoPrecipitation (ChIP), Chromatin in vivo Assay (CiA), etc.).

In some embodiments, a method involves use of two or more different guide RNAs. For example, two different guide RNAs can be used in a single host cell, where the two different guide RNAs target two different target sequences in the same target nucleic acid. In some embodiments, use of two different guide RNAs targeting two different targeting sequences in the same target nucleic acid provides for increased modulation (e.g. reduction or increase) in transcription of the target nucleic acid.

As another example, two different guide RNAs can be used in a single host cell, where the two different guide RNAs target two different target nucleic acids. Thus, for example, a transcriptional modulation method can further comprise introducing into the host cell a second guide RNA, or a nucleic acid comprising a nucleotide sequence encoding the second guide RNA.

In some embodiments, a nucleic acid (e.g. a guide RNA, e.g. a single-molecule guide RNA; a donor polynucleotide; a nucleic acid encoding a M-SmallCas9 polypeptide or variant thereof; etc.) comprises a modification or sequence that provides for an additional desirable feature (e.g. modified or regulated stability; subcellular targeting; tracking, e.g. a fluorescent label; a binding site for a protein or protein complex; etc.). Non-limiting examples include: a 5' cap (e.g. a 7-methylguanylate cap (m 7G)); a 3' polyadenylated tail (e.g., a 3' poly(A) tail); a riboswitch sequence or an aptamer sequence (e.g. to allow for regulated stability and/or regulated accessibility by proteins and/or protein complexes); a terminator sequence; a sequence that forms a dsRNA duplex (e.g., a hairpin)); a modification or sequence that targets the RNA to a subcellular location (e.g. nucleus, mitochondria, chloroplasts, and the like); a modification or sequence that provides for tracking (e.g. direct conjugation to a fluorescent molecule, conjugation to a moiety that facilitates fluorescent detection, a sequence that allows for fluorescent detection, etc.); a modification or sequence that provides a binding site for proteins (e.g. proteins that act on DNA, including transcriptional activators, transcriptional repressors, DNA methyltransferases, DNA demethylases, histone acetyltransferases, histone deacetylases, and the like); a modification of RNA that alters the structure of such RNA, consequently the M-SmallCas9 ribonucleoprotein; and combinations thereof.

Multiple Simultaneous Guide RNAs

In some embodiments, multiple guide RNAs are used simultaneously in the same cell to simultaneously modulate transcription at different locations on the same target DNA or on different target DNAs. In some embodiments, two or more guide RNAs target the same gene or transcript or locus. In some embodiments, two or more guide RNAs target different unrelated loci. In some embodiments, two or more guide RNAs target different, but related loci.

Because the guide RNAs are small and robust they can be simultaneously present on the same expression vector and can even be under the same transcriptional control if so desired. In some embodiments, two or more (e.g. 3 or more, 4 or more, 5 or more, 10 or more, 15 or more, 20 or more, 25 or more, 30 or more, 35 or more, 40 or more, 45 or more, or 50 or more) guide RNAs are simultaneously expressed in a target cell (from the same or different vectors/from the same or different promoters). In some embodiments, multiple guide RNAs can be encoded in an array mimicking naturally occurring CRISPR arrays of targeter RNAs. The targeting segments are encoded as approximately 30 nucleotide long sequences (can be about 16 to about 100 nt) and are separated by CRISPR repeat sequences. The array may be introduced into a cell by DNAs encoding the RNAs or as RNAs.

To express multiple guide RNAs, an artificial RNA processing system mediated by the Csy4 endoribonuclease can be used. For example, multiple guide RNAs can be concatenated into a tandem array on a precursor transcript (e.g. expressed from a U6 promoter), and separated by Csy4-specific RNA sequence. Co-expressed Csy4 protein cleaves the precursor transcript into multiple guide RNAs. Advantages for using an RNA processing system include: first, there is no need to use multiple promoters; second, since all guide RNAs are processed from a precursor transcript, their concentrations are normalized for similar dM-SmallCas9-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9%) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

Host Cells

In some embodiments, the methods of the disclosure may be employed to induce transcriptional modulation in mitotic or post-mitotic cells in vivo and/or ex vivo and/or in vitro. In some embodiments, the methods of the disclosure may be employed to induce DNA cleavage, DNA modification, and/or transcriptional modulation in mitotic or post-mitotic cells in vivo and/or ex vivo and/or in vitro (e.g. to produce genetically modified cells that can be reintroduced into an individual).

Because the guide RNA provides specificity by hybridizing to target DNA, a mitotic and/or post-mitotic cell can be any of a variety of host cell, where suitable host cells include, but are not limited to, a bacterial cell; an archaeal cell; a single-celled eukaryotic organism; a plant cell; an algal cell, e.g. *Botryococcus braunii, Chlamydomonas reinhardtii, Nannochloropsis gaditana, Chlorella pyrenoidosa, Sargassum patens, C. agardh*, and the like; a fungal cell; an animal cell; a cell from an invertebrate animal (e.g. an insect, a cnidarian, an echinoderm, a nematode, etc.); a eukaryotic parasite (e.g. a malarial parasite, e.g. *Plasmodium fakiparum*; a helminth; etc.); a cell from a vertebrate animal (e.g. fish, amphibian, reptile, bird, mammal); a mammalian cell, e.g. a rodent cell, a human cell, a non-human primate cell, etc. In some embodiments, the host cell can be any human cell. Suitable host cells include naturally occurring cells; genetically modified cells (e.g. cells genetically modified in a laboratory, e.g. by the "hand of man"); and cells manipulated in vitro in any way. In some embodiments, a host cell is isolated.

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g. a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, e.g., splittings, of the culture. For example, primary cultures include cultures that may have been passaged 0 times, 1 time, 2 times, 4 times, 5 times, 10 times, or 15 times, but not enough times go through the crisis stage. Primary cell lines can be are maintained for fewer than 10 passages in vitro. Target cells are, in some embodiments, unicellular organisms, or are grown in culture.

If the cells are primary cells, such cells may be harvested from an individual by any suitable method. For example, leukocytes may be suitably harvested by apheresis, leukocytapheresis, density gradient separation, etc., while cells from tissues such as skin, muscle, bone marrow, spleen, liver, pancreas, lung, intestine, stomach, etc. are most suitably harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., suitably supplemented with fetal calf serum or other naturally occurring factors, in conjunction with an acceptable buffer at low concentration, e.g. from 5-25 mM. Suitable buffers include HEPES, phosphate buffers, lactate buffers, etc. The cells may be used immediately, or they may be stored, frozen, for long periods of time, being thawed and capable of being reused. In such cases, the cells will generally be frozen in 10% dimethyl sulfoxide (DMSO), 50% serum, 40% buffered medium, or some other such solution as is commonly used in the art to preserve cells at such freezing temperatures, and thawed in a manner as commonly known in the art for thawing frozen cultured cells Uses A method for modulating transcription according to the present disclosure finds use in a variety of applications, which are also provided. Applications include research applications; diagnostic applications; industrial applications; and therapeutic applications.

Research applications include, e.g. determining the effect of reducing or increasing transcription of a target nucleic acid on, e.g. development, metabolism, expression of a downstream gene, and the like. High through-put genomic analysis can be carried out using a transcription modulation method, in which only the spacer of the guide RNA needs to be varied, while the protein-binding segment and the transcription termination segment can (in some cases) be held constant. A library comprising a plurality of nucleic acids used in the genomic analysis would include: a promoter operably linked to a guide RNA-encoding nucleotide sequence, where each nucleic acid would include a common protein-binding segment, a different spacer, and a common transcription termination segment. A chip could contain over $5\times10^4$ unique guide RNAs. Applications would include large-scale phenotyping, gene-to-function mapping, and meta-genomic analysis.

The methods disclosed herein find use in the field of metabolic engineering. Because transcription levels can be efficiently and predictably controlled by designing an appropriate guide RNA, as disclosed herein, the activity of metabolic pathways (e.g. biosynthetic pathways) can be precisely controlled and tuned by controlling the level of specific enzymes (e.g. via increased or decreased transcription) within a metabolic pathway of interest. Metabolic pathways of interest include those used for chemical (fine chemicals, fuel, antibiotics, toxins, agonists, antagonists, etc.) and/or drug production.

Biosynthetic pathways of interest include but are not limited to (1) the mevalonate pathway (e.g. HMG-CoA reductase pathway) (converts acetyl-GoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (e.g., the "2-C-methyl-D-erythritol 4-phosphate/1-deoxy-D-xylulose 5-phosphate pathway" or "MEP/DOXP pathway" or "DXP pathway") (also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e.g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate?-phosphate) synthesis pathway, (6) pathways that produce potential biofuels (such as short-chain alcohols and alkane, fatty acid methyl esters and fatty alcohols, isoprenoids, etc.), etc.

Networks and Cascades

The methods disclosed herein can be used to design integrated networks (e.g., a cascade or cascades) of control. For example, a guide RNA and M-SmallCas9 polypeptide or variant thereof may be used to control (e.g., modulate, e.g. increase, decrease) the expression of another DNA-targeting RNA or another M-SmallCas9 polypeptide or variant thereof. For example, a first guide RNA may be designed to target the modulation of transcription of a second fusion dM-SmallCas9 polypeptide with a function that is different than the first M-SmallCas9 polypeptide or variant thereof (e.g. methyltransferase activity, demethylase activity, acetyltransferase activity, deacetylase activity, etc.). In some embodiments, the second fusion dM-SmallCas9 polypeptide can be selected such that it may not interact with the first guide RNA. In some embodiments, the second fusion dM-SmallCas9 polypeptide can be selected such that it does interact with the first guide RNA. In some such cases, the activities of the two (or more) dM-SmallCas9 proteins may compete (e.g. if the polypeptides have opposing activities) or may synergize (e.g. if the polypeptides have similar or synergistic activities). Likewise, as noted above, any of the complexes (e.g., guide RNA/dM-SmallCas9 polypeptide) in the network can be designed to control other guide RNAs or dM-SmallCas9 polypeptides. Because a guide RNA and M-SmallCas9 polypeptide or variant thereof can be targeted to any desired DNA sequence, the methods described herein can be used to control and regulate the expression of any desired target. The integrated networks (e.g., cascades of interactions) that can be designed range from very simple to very complex, and are without limit.

In a network wherein two or more components (e.g. guide RNAs and dM-SmallCas9 polypeptides) are each under regulatory control of another guide RNA/dM-SmallCas9 polypeptide complex, the level of expression of one component of the network may affect the level of expression (e.g. may increase or decrease the expression) of another component of the network. Through this mechanism, the expression of one component may affect the expression of a different component in the same network, and the network may include a mix of components that increase the expression of other components, as well as components that decrease the expression of other components. As would be readily understood by one of skill in the art, the above examples whereby the level of expression of one component may affect the level of expression of one or more different component(s) are for illustrative purposes, and are not limiting. An additional layer of complexity may be optionally introduced into a network when one or more components are modified (as described above) to be manipulable (e.g., under experimental control, e.g. temperature control; drug control, e.g., drug inducible control; light control; etc.).

As one non-limiting example, a first guide RNA can bind to the promoter of a second guide RNA, which controls the expression of a target therapeutic/metabolic gene. In such a case, conditional expression of the first guide RNA indirectly activates the therapeutic/metabolic gene. RNA cascades of this type are useful, for example, for easily converting a repressor into an activator, and can be used to control the logics or dynamics of expression of a target gene.

A transcription modulation method can also be used for drug discovery and target validation.

Methods of Treating a Disease or Condition

In some aspects of the disclosure, the guide RNA and/or M-SmallCas9 polypeptide or variant thereof and/or donor polynucleotide are employed to modify cellular DNA in vivo, for purposes such as gene therapy, e.g. to treat a disease or as an antiviral, antipathogenic, or anticancer therapeutic, for the production of genetically modified organisms in agriculture, or for biological research. In these in vivo embodiments, components of a CRISPR/M-SmallCas9 system including (i) a guide RNA or nucleic acid encoding the gRNA; (ii) a nucleic acid comprising a codon-optimized polynucleotide sequence encoding a M-SmallCas9 polypeptide or variant thereof, or a M-SmallCas9 polypeptide or variant thereof expressed from the nucleic acid; and/or (iii) a donor polynucleotide are administered to the individual. Administration may be by any well-known method in the art for the administration of peptides, small molecules and nucleic acids to a subject. The CRISPR/M-SmallCas9 system components can be incorporated into a variety of formulations. More particularly, the CRISPR/M-SmallCas9 system components of the present disclosure can be formulated into pharmaceutical compositions by combination with appropriate pharmaceutically acceptable carriers or diluents.

In some embodiments, provided herein are pharmaceutical preparations or compositions comprising components of a CRISPR/M-SmallCas9 system including (i) a guide RNA or nucleic acid encoding the gRNA; (ii) a nucleic acid comprising a codon-optimized polynucleotide sequence encoding a M-SmallCas9 polypeptide or variant thereof, or a M-SmallCas9 polypeptide or variant thereof expressed from the nucleic acid; and/or (iii) a donor polynucleotide present in a pharmaceutically acceptable vehicle. "Pharmaceutically acceptable vehicles" may be vehicles approved by a regulatory agency of the Federal or a state government or listed in the US Pharmacopeia or other generally recognized pharmacopeia for use in mammals, such as humans. The term "vehicle" refers to a diluent, adjuvant, excipient, or carrier with which a compound of the disclosure is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semisolid, liquid or gaseous forms, such as tablets, capsules, powders, granules, ointments, solutions, suppositories, injections, inhalants, gels, microspheres, and aerosols. As such, administration of the CRISPR/M-SmallCas9 system components can be achieved in various ways, including oral, buccal, rectal, parenteral, intraperitoneal, intradermal, transdermal, intra-tracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the BBB entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the disclosure when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such asp-glycoprotein. Active transport moieties may also be conjugated to the therapeutic compounds for use in the disclosure to facilitate transport across the endothelial wall of the blood vessel. In addition or alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g., U.S. Application No. 20070254842, incorporated here by reference); or by implanting a device upon which the agent has been reversibly affixed (see e.g. U.S. application Nos. 20080081064 and 20090196903, incorporated herein by reference).

Generally, an effective amount of components of a CRISPR/M-SmallCas9 system including (i) a guide RNA or nucleic acid encoding the gRNA; (ii) a nucleic acid comprising a codon-optimized polynucleotide sequence encoding a M-SmallCas9 polypeptide or variant thereof, or a M-SmallCas9 polypeptide or variant thereof expressed from the nucleic acid; and/or (iii) a donor polynucleotide are provided. As discussed above with regard to ex vivo methods, an effective amount or effective dose of the CRISPR/M-SmallCas9 system components in vivo is the amount to induce a 2-fold increase or more in the amount of recombination observed between two homologous sequences relative to a negative control, e.g. a cell contacted with an empty vector or irrelevant polypeptide. The amount of recombination may be measured by any suitable method, e.g. as described above and known in the art. The calculation of the effective amount or effective dose of the CRISPR/M-SmallCas9 system components to be administered is within the skill of one of ordinary skill in the art, and will be routine to those persons skilled in the art. The final amount to be administered will be dependent upon the route of administration and upon the nature of the disorder or condition that is to be treated.

The effective amount given to a particular subject will depend on a variety of factors, several of which will differ from subject to subject. A competent clinician will be able to determine an effective amount of a therapeutic agent to administer to a subject to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions, which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the CRISPR/M-SmallCas9 system components may be obtained from a suitable commercial source. As a general proposition, the total pharmaceutically effective amount of the CRISPR/M-SmallCas9 system components administered parenterally per dose will be in a range that can be measured by a dose response curve.

Therapies based on the CRISPR/M-SmallCas9 system components, e.g., preparations of (i) a guide RNA or nucleic acid encoding the gRNA; (ii) a nucleic acid comprising a codon-optimized polynucleotide sequence encoding a M-SmallCas9 polypeptide or variant thereof, or a M-SmallCas9 polypeptide or variant thereof expressed from the nucleic acid; and/or (iii) a donor polynucleotide to be used for therapeutic administration, must be sterile. Sterility is readily accomplished by filtration through sterile filtration membranes (e.g. 0.2 micrometer membranes). Therapeutic compositions generally are placed into a container having a sterile access port, for example, an intravenous solution bag or vial having a stopper pierceable by a hypodermic injection needle. The therapies based on the CRISPR/M-SmallCas9 system components may be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g. increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g. sodium, potassium, calcium, magnesium, manganese}, and lipids.

Further guidance regarding formulations suitable for various types of administration can be found in Remington's Pharmaceutical Sciences, Mace Publishing Company, Philadelphia, Pa., 20th ed. (2003) and in The United States Pharmacopeia: The National Formulary (USP 24 NF19) published in 1999. For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population}. The dose ratio between toxic and therapeutic effects is the therapeutic index and it can be expressed as the ratio LD50/ED50. Therapies that exhibit large therapeutic indices are generally preferred.

The data obtained from cell culture and/or animal studies can be used in formulating a range of dosages for humans. The dosage of the active ingredient generally lines within a range of circulating concentrations that include the ED50 with low toxicity. The dosage can vary within this range depending upon the dosage form employed and the route of administration utilized. The components used to formulate the pharmaceutical compositions are generally of high purity and are substantially free of potentially harmful contaminants (e.g., at least National Food (NF) grade, generally at least analytical grade, and more typically at least pharmaceutical grade). Moreover, compositions intended for in vivo use are generally sterile. To the extent that a given compound must be synthesized prior to use, the resulting product is generally substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular subject will depend on a variety of factors, several of which will differ from subject to subject. A competent clinician will be able to determine an effective amount of a therapeutic agent to administer to a subject to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions that are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

The number of administrations of treatment to a subject may vary. Introducing the genetically modified cells into the subject may be a one-time event; but in certain situations, such treatment may elicit improvement for a limited period of time and require an on-going series of repeated treatments. In certain situations, multiple administrations of the genetically modified cells may be required before an effect is observed. The exact protocols depend upon the disease or condition, the stage of the disease and parameters of the individual subject being treated.

EQUIVALENTS

All technical features can be individually combined in all possible combinations of such features.

The invention may be embodied in other specific forms without departing from the spirit or essential characteristics thereof. The foregoing embodiments are therefore to be considered in all respects illustrative rather than limiting on the invention described herein.

EXAMPLES

The following non-limiting examples further illustrate embodiments of the inventions described herein.

Example 1: Screening M-Small Cas9 Nucleases

To determine whether mutated Cas9 nucleases had improved features, variants of M-SmallCas9: M-SauCas9-R420A, according to SEQ ID NO. 6; M-SluCas9-R414A, according to SEQ ID NO. 7; M-Gib11SpaCas9-1-M417L (according to SEQ ID NO. 133); and MGib11SpaCas9-3-E410A, according to SEQ ID NO. 8 are tested in comparison to a) SluCas9 (SEQ ID NO. 9), and
b) SauCas9 (NCBI GenPept database; Accession No. CRI31653.1; www.ncbi.nlm.nih.gov/protein/CRI31653.1; accessed on Nov. 21, 2018.)

in a fluorescence polarization-based biochemical cleavage assay. Protein variants are adjusted to same activity levels. Upon incubation of the variants- or SluCas9-RNP complex targeting the R01 or BFP oligonucleotide dsDNA substrate sequence or all possible single nucleotide exchanges of these sequence-cleavage is observed by changes in the fluorescence polarization and fluorescence intensity signal (decrease of polarization values and increase in fluorescence intensity over time upon successful cleavage).

As a quantitative estimate of the cleavage reaction, the initial slope of the graph is analyzed. Specificity is assessed by comparing the cleavage (slope) of any one of the 60 single nucleotide mismatch oligonucleotides to the cleavage (slope) of the original R01 and BFP sequence.

The results indicate that the variants M-SauCas9-R420A, M-SluCas9-R414A, and M-Gib11SpaCas9-3-E410A, M-Gib11SpaCas9-1-M417L, as well as the wildtype SluCas9 and SauCas9 successfully cleave an oligonucleotide substrate. Moreover the fidelity of the variants appears to be significantly increased when compared to the respective wildtype protein.

Example 2: Determination of Biochemical Specificity Profile for SluCas9 and M-SluCas9R414A To assess the specificity profile of SluCas9 (according to SEQ ID NO. 9) and M-SluCas9R414A (SEQ ID NO. 7), biochemical cleavage of an on-target sequence and all 60-derived single nucleotide mismatched dsDNA substrates (according to SEQ ID Nos. 11 to 132 used as pairs e.g. R01-1-A and R01-1-B with SEQ ID NOs. 11 and 12 represented one duplex pair) were determined. Oligonucleotide duplexes were prepared in 10 mM Tris (pH 7.8) 50 mM NaCl as 10 μM solutions (from 100 UM stocks) and annealed at 95° C. for 5 minutes then slowly cooled down in thermo cycler (6° C. per minute). The stocks were subsequently diluted in 10 mM Tris (pH 7.8), 50 mM NaCl, and 0.05% Pluronic. 20 μl of each oligonucleotide (20 nM) was immobilized on streptavidin coated plates, washed twice after 10 minutes and then incubated with a 20 μl sample for a kinetics of 60 minutes (excitation wavelength: 635 nm; emission wavelength: 670 nm). Prior to the cleavage the reaction RNP was formed. RNP was assembled by mixing 12.03 μl of the respective Cas9 protein (1.21 μg/μl) in 3200 μl 1×PBS+5 mM MgCl2 with and without sgRNA (SEQ ID NO. 10; 60 nM final concentration), RNPs were incubated 5 min at 37° C. prior to the reaction. 20 µl RNP was added to each well and the polarization was measured for 60 minutes at 37° C.

The cleavage kinetics were analyzed by calculating the initial slope of the oligonucleotide cleavage reaction. The slopes were calculated for each of the 61 substrates and normalized to the value of the on-target substrate (defined as 1). The normalized cleavage values for all 60 off-target substrates where then grouped according to their position. For each of the 20 nucleotide positions in the target sequence, the normalized cleavage value of the three single nucleotide mismatches was blotted to illustrate the position-specific nucleotide tolerance of the tested nuclease.

The results are shown in FIG. 1. Apparently M-SluCas9R414A was more specific than SluCas9 wild type.

Figure 2:
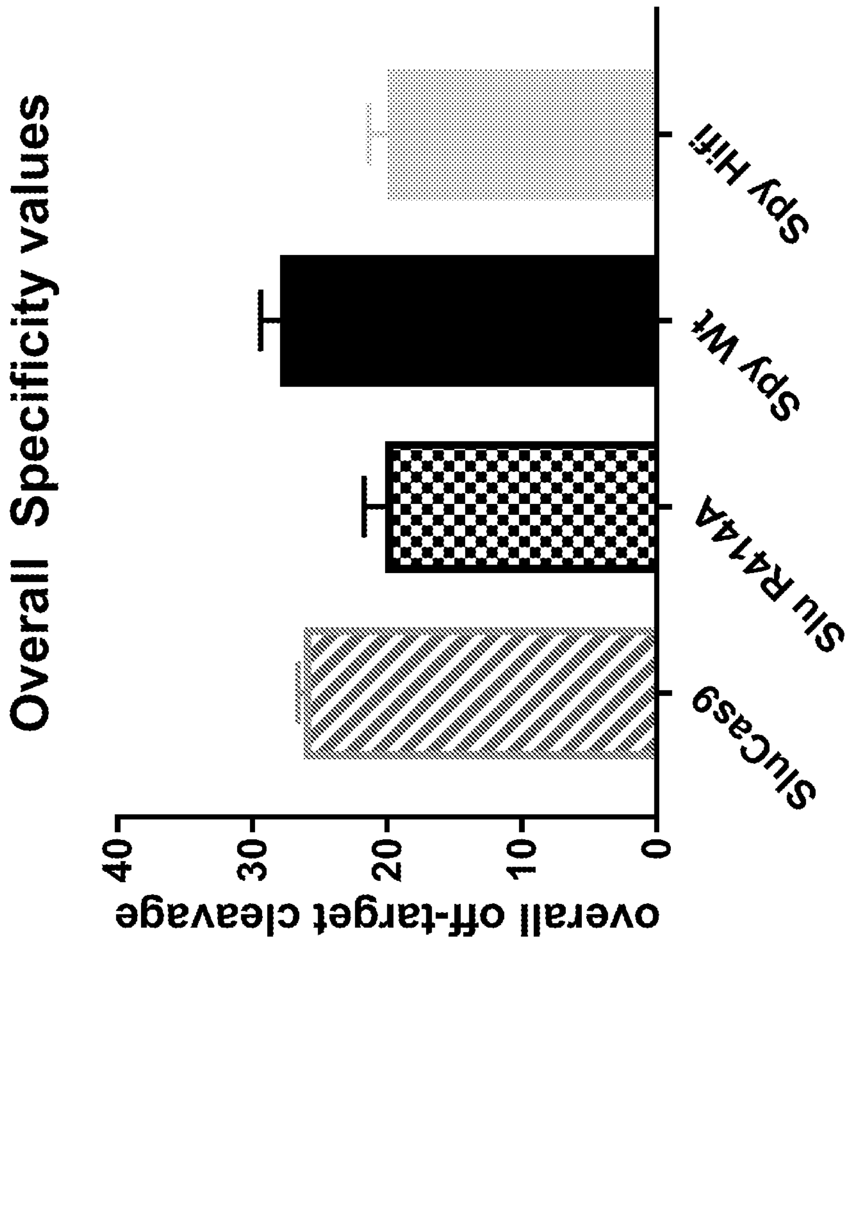
FIG. 2 is a bar graph depicting the results of experiments detecting the total specificity values of four different Cas enzymes: SluCas9 (SEQ ID NO: 9), M-SluCas9R414A (SEQ ID NO. 7), *Staphylococcus pyogenes* wild type (New England Biolabs), *Staphylococcus pyogenes* HiFi (Integrated DNA Technologies).

Overall Specificity of M-SmallCas Nucleases:

The cleavage kinetics for a) SluCas9 (SEQ ID NO: 9); b) M-SluCas9R414A (SEQ ID NO. 7); c) *Staphylococcus pyogenes* wild type (New England Biolabs), and d) *Staphylococcus pyogenes* HiFi (Integrated DNA Technologies), were analyzed by calculating the initial slope of the oligonucleotide cleavage reaction. The slopes were calculated for each of the 61 substrates and are normalized to the value of the on-target substrate (defined as 1). All normalized values across the entire panel of 60 off-target substrates were summed to yield an overall specificity value (as depicted in the bar graph in FIG. 2).

Reference for Sequence Listing

| SEQ ID NO: | Identifier | Remarks |
|---|---|---|
| 1 | M-SauCas9_X | |
| 2 | M-SluCas9_x | |
| 3 | M-SpaCas9_X | |
| 4 | M-ShyCas9_X | |
| 5 | M-SmiCas9_X | |
| 6 | M-SauCas9R420A | |
| 7 | M-SluCas9R414A | |
| 8 | MGib11SpaCas9-3E410A | |
| 9 | SluCas9 | Wildtype sequence of SluCas9 used in Examples |
| 10 | sgRNA_Ex1 | sgRNA sequence for Example 1 |
| 11 | R01-1-A | 5'-ATTO647N- |
| 12 | R01-1-B | 3'-Biotin |
| 13 | R01-2-A | 5'-ATTO647N- |
| 14 | R01-2-B | 3'-Biotin |
| 15 | R01-3-A | 5'-ATTO647N- |
| 16 | R01-3-B | 3'-Biotin |
| 17 | R01-4-A | 5'-ATTO647N- |
| 18 | R01-4-B | 3'-Biotin |
| 19 | R01-5-A | 5'-ATTO647N- |
| 20 | R01-5-B | 3'-Biotin |
| 21 | R01-6-A | 5'-ATTO647N- |
| 22 | R01-6-B | 3'-Biotin |
| 23 | R01-7-A | 5'-ATTO647N- |
| 24 | R01-7-B | 3'-Biotin |
| 25 | R01-8-A | 5'-ATTO647N- |
| 26 | R01-8-B | 3'-Biotin |
| 27 | R01-9-A | 5'-ATTO647N- |
| 28 | R01-9-B | 3'-Biotin |
| 29 | R01-10-A | 5'-ATTO647N- |
| 30 | R01-10-B | 3'-Biotin |
| 31 | R01-11-A | 5'-ATTO647N- |
| 32 | R01-11-B | 3'-Biotin |
| 33 | R01-12-A | 5'-ATTO647N- |
| 34 | R01-12-B | 3'-Biotin |
| 35 | R01-13-A | 5'-ATTO647N- |
| 36 | R01-13-B | 3'-Biotin |
| 37 | R01-14-A | 5'-ATTO647N- |
| 38 | R01-14-B | 3'-Biotin |
| 39 | R01-15-A | 5'-ATTO647N- |
| 40 | R01-15-B | 3'-Biotin |

-continued

Reference for Sequence Listing

| SEQ ID NO: | Identifier | Remarks |
|---|---|---|
| 41 | R01-16-A | 5'-ATTO647N- |
| 42 | R01-16-B | 3'-Biotin |
| 43 | R01-17-A | 5'-ATTO647N- |
| 44 | R01-17-B | 3'-Biotin |
| 45 | R01-18-A | 5'-ATTO647N- |
| 46 | R01-18-B | 3'-Biotin |
| 47 | R01-19-A | 5'-ATTO647N- |
| 48 | R01-19-B | 3'-Biotin |
| 49 | R01-20-A | 5'-ATTO647N- |
| 50 | R01-20-B | 3'-Biotin |
| 51 | R01-21-A | 5'-ATTO647N- |
| 52 | R01-21-B | 3'-Biotin |
| 53 | R01-22-A | 5'-ATTO647N- |
| 54 | R01-22-B | 3'-Biotin |
| 55 | R01-23-A | 5'-ATTO647N- |
| 56 | R01-23-B | 3'-Biotin |
| 57 | R01-24-A | 5'-ATTO647N- |
| 58 | R01-24-B | 3'-Biotin |
| 59 | R01-25-A | 5'-ATTO647N- |
| 60 | R01-25-B | 3'-Biotin |
| 61 | R01-26-A | 5'-ATTO647N- |
| 62 | R01-26-B | 3'-Biotin |
| 63 | R01-27-A | 5'-ATTO647N- |
| 64 | R01-27-B | 3'-Biotin |
| 65 | R01-28-A | 5'-ATTO647N- |
| 66 | R01-28-B | 3'-Biotin |
| 67 | R01-29-A | 5'-ATTO647N- |
| 68 | R01-29-B | 3'-Biotin |
| 69 | R01-30-A | 5'-ATTO647N- |
| 70 | R01-30-B | 3'-Biotin |
| 71 | R01-31-A | 5'-ATTO647N- |
| 72 | R01-31-B | 3'-Biotin |
| 73 | R01-32-A | 5'-ATTO647N- |
| 74 | R01-32-B | 3'-Biotin |
| 75 | R01-33-A | 5'-ATTO647N- |
| 76 | R01-33-B | 3'-Biotin |
| 77 | R01-34-A | 5'-ATTO647N- |
| 78 | R01-34-B | 3'-Biotin |
| 79 | R01-35-A | 5'-ATTO647N- |
| 80 | R01-35-B | 3'-Biotin |
| 81 | R01-36-A | 5'-ATTO647N- |
| 82 | R01-36-B | 3'-Biotin |
| 83 | R01-37-A | 5'-ATTO647N- |
| 84 | R01-37-B | 3'-Biotin |
| 85 | R01-38-A | 5'-ATTO647N- |
| 86 | R01-38-B | 3'-Biotin |
| 87 | R01-39-A | 5'-ATTO647N- |
| 88 | R01-39-B | 3'-Biotin |
| 89 | R01-40-A | 5'-ATTO647N- |
| 90 | R01-40-B | 3'-Biotin |
| 91 | R01-41-A | 5'-ATTO647N- |
| 92 | R01-41-B | 3'-Biotin |
| 93 | R01-42-A | 5'-ATTO647N- |
| 94 | R01-42-B | 3'-Biotin |
| 95 | R01-43-A | 5'-ATTO647N- |
| 96 | R01-43-B | 3'-Biotin |
| 97 | R01-44-A | 5'-ATTO647N- |
| 98 | R01-44-B | 3'-Biotin |
| 99 | R01-45-A | 5'-ATTO647N- |
| 100 | R01-45-B | 3'-Biotin |
| 101 | R01-46-A | 5'-ATTO647N- |
| 102 | R01-46-B | 3'-Biotin |
| 103 | R01-47-A | 5'-ATTO647N- |
| 104 | R01-47-B | 3'-Biotin |
| 105 | R01-48-A | 5'-ATTO647N- |
| 106 | R01-48-B | 3'-Biotin |
| 107 | R01-49-A | 5'-ATTO647N- |
| 108 | R01-49-B | 3'-Biotin |
| 109 | R01-50-A | 5'-ATTO647N- |
| 110 | R01-50-B | 3'-Biotin |
| 111 | R01-51-A | 5'-ATTO647N- |
| 112 | R01-51-B | 3'-Biotin |
| 113 | R01-52-A | 5'-ATTO647N- |
| 114 | R01-52-B | 3'-Biotin |
| 115 | R01-53-A | 5'-ATTO647N- |

-continued

| Reference for Sequence Listing | | |
|---|---|---|
| SEQ ID NO: | Identifier | Remarks |
| 116 | R01-53-B | 3'-Biotin |
| 117 | R01-54-A | 5'-ATTO647N- |
| 118 | R01-54-B | 3'-Biotin |
| 119 | R01-55-A | 5'-ATTO647N- |
| 120 | R01-55-B | 3'-Biotin |
| 121 | R01-56-A | 5'-ATTO647N- |
| 122 | R01-56-B | 3'-Biotin |
| 123 | R01-57-A | 5'-ATTO647N- |
| 124 | R01-57-B | 3'-Biotin |
| 125 | R01-58-A | 5'-ATTO647N- |
| 126 | R01-58-B | 3'-Biotin |
| 127 | R01-59-A | 5'-ATTO647N- |
| 128 | R01-59-B | 3'-Biotin |
| 129 | R01-60-A | 5'-ATTO647N- |
| 130 | R01-60-B | 3'-Biotin |
| 131 | R01-61-A | 5'-ATTO647N- |
| 132 | R01-61-B | 3'-Biotin |
| 133 | Gib11SpaCas9-1-M417L | |

SEQUENCE LISTING

| SEQ ID NO | Sequence | Description |
|---|---|---|
| 1 | MKRNYILGLDIGITSVGYGIIDYETRDVIDAGVRLFKEANVENNEGRRSKRGARRLKRRR<br>RHRIQRVKKLLFDYNLLTDHSELSGINPYEARVKGLSQKLSEEEFSAALLHLAKRRGVHN<br>VNEVEEDTGNELSTKEQISRNSKALEEKYVAELQLERLKKDGEVRGSINRFKTSDYVKEA<br>KQLLKVQKAYHQLDQSFIDTYIDLLETRRTYYEGPGEGSPFGWKDIKEWYEMLMGHCTYF<br>PEELRSVKYAYNADLYNALNDLNNLVITRDENEKLEYYEKFQIIENVFKQKKKPTLKQIA<br>KEILVNEEDIKGYRVTSTGKPEFTNLKVYHDIKDITARKEIIENAELLDQIAKILTIYQS<br>SEDIQEELTNLNSELTQEEIEQISNLKGYTGTHNLSLKAINLILD**X**LWHTN**X**NQI**X**IFN**X**<br>LKLVPKKVDLSQQKEIPTTLVDDFILSPVVKRSFIQSIKVINAIIKKYGLPNDIIIELAR<br>EKNSKDAQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEENSKKGNRTPFQYLSSSDSKIS<br>YETFKKHILNLAKGKGRISKTKKEYLLEERDINRFSVQKDFINRNLVDTRYATRGLMNLL<br>RSYFRVNNLDVKVKSINGGFTSFLRRKWKFKKERNKGYKHHAEDALIIANADFIFKEWKK<br>LDKAKKVMENQMFEEKQAESMPEIETEQEYKEIFITPHQIKHIKDFKDYKYSHRVDKKPN<br>RELINDTLYSTRKDDKGNTLIVNNLNGLYDKDNDKLKKLINKSPEKLLMYHHDPQTYQKL<br>KLIMEQYGDEKNPLYKYYEETGNYLTKYSKKDNGPVIKKIKYYGNKLNAHLDITDDYPNS<br>RNKVVKLSLKPYRFDVYLDNGVYKFVTVKNLDVIKKENYYEVNSKCYEEAKKLKKISNQA<br>EFIASFYNNDLIKINGELYRVIGVNNDLLNRIEVNMIDITYREYLENMNDKRPPRIIKTI<br>ASKTQSIKKYSTDILGNLYEVKSKKHPQIIKKG | M-SauCas9_X |
| 2 | MNQKFILGLDIGITSVGYGLIDYETKNIIDAGVRLFPEANVENNEGRRSKRGSRRLKRRR<br>IHRLERVKKLLEDYNLLDQSQIPQSTNPYAIRVKGLSEALSKDELVIALLHIAKRRGIHK<br>IDVIDSNDDVGNELSTKEQLNKNSKLLKDKFVCQIQLERMNEGQVRGEKNRFKTADIIKE<br>IIQLLNVQKNFHQLDENFINKYIELVEMRREYFEGPGKGSPYGWEGDPKAWYETLMGH**X**T<br>YFPDELRSVKYAYSADLFNALNDLNNLVIQRDGLSKLEYHEKYHIIENVFKQKKKPTLKQ<br>IANEINVNPEDIKGYRITKSGKPQFTEFKLYHDLKSVLFDQSILENEDVLDQIAEILTIY<br>QDKDSIKSKLTELDILLNEEDKENIAQLTGYTGTHRLSLK**X**IRLVLE**X**QWYSS**X**NQMXIF<br>T**X**LNIKPKKINLTAANKIPKAMIDEFILSPVVKRTFGQAINLINKIIEKYGVPEDIIIEL<br>ARENNSKDKQKFINEMQKKNENTRKRINEIIGKYGNQNAKRLVEKIRLHDEQEGKCLYSL<br>ESIPLEDLLNNPNHYEVDHIIPRSVSFDNSYHNKVLVKQSENSKKSNLTPYQYFNSGKSK<br>LSYNQFKQHILNLSKSQDRISKKKKEYLLEERDINKFEVQKEFINRNLVDTRYATRELTN<br>YLKAYFSANNMNVKVKTINGSFTDYLRKVWKFKKERNHGYKHHAEDALIIANADFLFKEN<br>KKLKAVNSVLEKPEIETKQLDIQVDSEDNYSEMFIIPKQVQDIKDFRNFKYSHRVDKKPN<br>RQLINDTLYSTRKKDNSTYIVQTIKDIYAKDNTTLKKQFDKSPEKFLMYQHDPRTFEKLE<br>VIMKQYANEKNPLAKYHEETGEYLTKYSKKNNGPIVKSLKYIGNKLGSHLDVTHQFKSST<br>KKLVKLSIKPYRFDVYLTDKGYKFITISYLDVLKKDNYYYIPEQKYDKLKLGKAIDKNAK<br>FIASFYKNDLIKLDGEIYKIIGVNSDTRNMIELDLPDIRYKEYCELNNIKGEPRIKKTIG<br>KKVNSIEKLTTDVLGNVFTNTQYTKPQLLFKRGNGG | M-SluCas9_x |
| 3 | MKEKYILGLDLGITSVGYGIINFETKKIIDAGVRLFPEANVDNNEGRRSKRGSRRLKRRR<br>IHRLERVKLLLTEYDLINKEQIPTSNNPYQIRVKGLSEILSKDELAIALLHLAKRRGIHN<br>INVSSEDEDASNELSTKEQINRNNKLLKDKYVCEVQLQRLKEGQIRGEKNRFKTTDILKE<br>IDQLLKVQKDYHNLDIDFINQYKEIVETRREYFEGPGQGSPFGWNGDLKKWYEMLMGH**X**T<br>YFPQELRSVKYAYSADLFNALNDLNNLIIQRDNSEKLEYHEKYHIIENVFKQKKKPTLKQ<br>IAKEIGVNPEDIKGYRITKSGTPQFTEFKLYHDLKSIVFDKSILENEAILDQIAEILTIY<br>QDEQSIKEELNKLPEILNEQDKAEIAKLIGYNGTHRLSLK**X**IHLINE**X**LWQTS**X**NQM**X**IF<br>N**X**LNIKPNKVDLSEQNKIPKDMVNDFILSPVVKRTFIQSINVINKVIEKYGIPEDIIIEL<br>ARENNSDDRKKFINNLQKKNEATRKRINEIIGQTGNQNAKRIVEKIRLHDQQEGKCLYSL<br>ESIALMDLLNNPQNYEVDHIIPRSVAFDNSIHNKVLVKQIENSKKGNRTPYQYLNSSDAK<br>LSYNQFKQHILNLSKSKDRISKKKKDYLLEERDINKFEVQKEFINRNLVDTRYATRELTS<br>YLKAYFSANNMDVKVKTINGSFTNHLRKVWRFDKYRNHGYKHHAEDALIIANADFLFKEN<br>KKLQNTNKILEKPTIENNTKKVTVEKEEDYNNVFETPKLVEDIKQYRDYKFSHRVDKKPN<br>RQLINDTLYSTRMKDEHDYIVQTITDIYGKDNTNLKKQFNKNPEKFLMYQNDPKTFEKLS<br>IIMKQYSDEKNPLAKYYEETGEYLTKYSKKNNGPIVKKIKLLGNKVGNHLDVTNKYENST<br>KKLVKLSIKNYRFDVYLTEKGYKFVTIAYLNVFKKDNYYYIPKDKYQELKEKKKIKDTDQ<br>FIASFYKNDLIKLNGDLYKIIGVNSDDRNIIELDYYDIKYKDYCEINNIKGEPRIKKTIG<br>KKTESIEKFTTDVLGNLYLHSTEKAPQLIFKRGL | M-SpaCas9_X |

-continued

SEQUENCE LISTING

| SEQ ID NO | Sequence | Description |
|---|---|---|
| 4 | MNNYILGLDIGITSVGYGIVDSDTREIKDAGVRLFPEANVDNNEGRRSKRGARRLKRRRI<br>HRLDRVKHLLAEYDLLDLTNIPKSTNPYQTRVKGLNEKLSKDELVIALLHIAKRRGIHNV<br>NVMMDDNDSGNELSTKDQLKKNAKALSDKYVCELQLERFEQDYKVRGEKNRFKTEDFVRE<br>ARKLLETQSKFFEIDQTFIMRYIELIETRREYFEGPGKGSPFGWEGNIKKWFEQMMGH**X**T<br>YFPEELRSVKYSYSAELFNALNDLNNLVITRDEDAKLNYGEKFQIIENVFKQKKTPNLKQ<br>IAIEIGVHETEIKGYRVNKSGKPEFTQFKLYHDLKNIFKDPKYLNDIQLMDNIAEIITIY<br>QDAESIIKELNQLPELLSEREKEKISALSGYSGTHRLSLK**X**INLLLD**X**LWESS**X**NQM**X**LF<br>T**X**LNLKPKKIDLSQQHKIPSKLVDDFILSPVVKRAFIQSIQVVNAIIDKYGLPEDIIIEL<br>ARENNSDDRRKFLNQLQKQNEETRKQVEKVLREYGNDNAKRIVQKIKLHNMQEGKCLYSL<br>KDIPLEDLLRNPHHYEVDHIIPRSVAFDNSMHNKVLVRADENSKKGNRTPYQYLNSSESS<br>LSYNEFKQHILNLSKTKDRITKKKREYLLEERDINKFDVQKEFINRNLVDTRYATRELTS<br>LLKAYFSANNLDVKVKTINGSFTNYLRKVWKFDKDRNKGYKHHAEDALIIANADFLFKHN<br>KKLRNINKVLDAPSKEVDKKRVTVQSEDEYNQIFEDTQKAQAIKKFEIRKFSHRVDKKPN<br>RQLINDTLYSTRNIDGIEYVVESIKDIYSVNNDKVKTKFKKDPHRLLMYRNDPQTFEKFE<br>KVFKQYESEKNPFAKYYEETGEKIRKFSKTGQGPYINKIKYLRERLGRHCDVTNKYINSR<br>NKIVQLKIYSYRFDIYQYGNNYKMITISYIDLEQKSNYYYISREKYEQKKKDKQIDDSYK<br>FIGSFYKNDIINYNGEMYRVIGVNDSEKNKIQLDMIDISIKDYMELNNIKKTGVIYKTIG<br>KSTTHIEKYTTDILGNLYKAAPPKKPQLIFK | M-ShyCas9_X |
| 5 | MEKDYILGLDIGIGSVGYGLIDYDTKSIIDAGVRLFPEANADNNLGRRAKRGARRLKRRR<br>IHRLERVKSLLSEYKIISGLAPTNNQPYNIRVKGLTEQLTKDELAVALLHIAKRRGIHNV<br>DVAADKEETASDSLSTKDQINKNAKFLESRYVCELQKERLENEGHVRGVENRFLTKDIVR<br>EAKKIIDTQMQYYPEIDETFKEKYISLVETRREYYEGPGKGSPYGWDADVKKWYQLMMGH<br>**X**TYFPVEFRSVKYAYTADLYNALNDLNNLTIARDDNPKLEYHEKYHIIENVFKQKRNPTL<br>KQIAKEIGVNDINISGYRVTKSGKPQFTSFKLFHDLKKVVKDHAILDDIDLLNQIAEILT<br>IYQDKDSIVAELGQLEYLMSEADKQSISELTGYTGTHSLSLK**X**MNMIID**X**LWHSS**X**NQM**X**<br>VFT**X**LNMRPKKYELKGYQRIPTDMIDDAILSPVVKRSFKQAIGVVNAIIKKYGLPKDIII<br>ELARESNSAEKSRYLRAIQKKNEKTRERIEAIIKEYGNENAKGLVQKIKLHDAQEGKCLY<br>SLKDIPLEDLLRNPNNYDIDHIIPRSVSFDDSMHNKVLVRREQNAKKNNQTPYQYLTSGY<br>ADIKYSVFKQHVLNLAENKDRMTKKKREYLLEERNINKYDVQKEFINRNLVDTRYTTREL<br>TTLLKTYFTINNLDVKVKTINGSFTDFLRKRWGFKKNRDEGYKHHAEDALIIANADYLFK<br>ERKLLKEIKDVSDLAGDERNSNVKDEDQYEEVFGGYFKIEDIKKYKIKKFSHRVDKKPNR<br>QLINDTIYSTRVKDDKRYLINTLKNLYDKSNGDLKERMQKDPESLLMYHHDPQTFEKLKI<br>VMSQYENEKNPLAKYFEETGQYLTKYAKHDNGPAIHKIKYYGNKLVEHLDITKNYHNPQN<br>KVVQLSQKSFRFDVYQTDKGYKFISIAYLTLKNEKNYYAISQEKYDQLKSEKKISNNAVF<br>IGSFYTSDIIEINNEKFRVIGVNSDKNNLIEVDRIDIRQKEFIELEEEKKNNRIKVTIGR<br>KTTNIEKFHTDILGNMYKSKRPKAPQLVFKKG | M-SmiCas9_X |
| 6 | MKRNYILGLDIGITSVGYGIIDYETRDVIDAGVRLFKEANVENNEGRRSKRGARRLKRRR<br>RHRIQRVKKLLFDYNLLTDHSELSGINPYEARVKGLSQKLSEEEFSAALLHLAKRRGVHN<br>VNEVEEDTGNELSTKEQISRNSKALEEKYVAELQLERLKKDGEVRGSINRFKTSDYVKEA<br>KQLLKVQKAYHQLDQSFIDTYIDLLETRRTYYEGPGEGSPFGWKDIKEWYEMLMGHCTYF<br>PEELRSVKYAYNADLYNALNDLNNLVITRDENEKLEYYEKFQIIENVFKQKKKPTLKQIA<br>KEILVNEEDIKGYRVTSTGKPEFTNLKVYHDIKDITARKEIIENAELLDQIAKILTIYQS<br>SEDIQEELTNLNSELTQEEIEQISNLKGYTGTHNLSLKAINLILDELWHTNDNQIAIFNA<br>LKLVPKKVDLSQQKEIPTTLVDDFILSPVVKRSFIQSIKVINAIIKKYGLPNDIIIELAR<br>EKNSKDAQKMINEMQKRNRQTNERIEEIIRTTGKENAKYLIEKIKLHDMQEGKCLYSLEA<br>IPLEDLLNNPFNYEVDHIIPRSVSFDNSFNNKVLVKQEENSKKGNRTPFQYLSSSDSKIS<br>YETFKKHILNLAKGKGRISKTKKEYLLEERDINRFSVQKDFINRNLVDTRYATRGLMNLL<br>RSYFRVNNLDVKVKSINGGFTSFLRRKWKFKKERNKGYKHHAEDALIIANADFIFKEWKK<br>LDKAKKVMENQMFEEKQAESMPEIETEQEYKEIFITPHQIKHIKDFKDYKYSHRVDKKPN<br>RELINDTLYSTRKDDKGNTLIVNNLNGLYDKDNDKLKKLINKSPEKLLMYHHDPQTYQKL<br>KLIMEQYGDEKNPLYKYYEETGNYLTKYSKKDNGPVIKKIKYYGNKLNAHLDITDDYPNS<br>RNKVVKLSLKPYRFDVYLDNGVYKFVTVKNLDVIKKENYYEVNSKCYEEAKKLKKISNQA<br>EFIASFYNNDLIKINGELYRVIGVNNDLLNRIEVNMIDITYREYLENMNDKRPPRIIKTI<br>ASKTQSIKKYSTDILGNLYEVKSKKHPQIIKKG | M-<br>SauCas9R420A |
| 7 | MNQKFILGLDIGITSVGYGLIDYETKNIIDAGVRLFPEANVENNEGRRSKRGSRRLKRRR<br>IHRLERVKKLLEDYNLLDQSQIPQSTNPYAIRVKGLSEALSKDELVIALLHIAKRRGIHK<br>IDVIDSNDDVGNELSTKEQLNKNSKLLKDKFVCQIQLERMNEGQVRGEKNRFKTADIIKE<br>IIQLLNVQKNFHQLDENFINKYIELVEMRREYFEGPGKGSPYGWEGDPKAWYETLMGHCT<br>YFPDELRSVKYAYSADLFNALNDLNNLVIQRDGLSKLEYHEKYHIIENVFKQKKKPTLKQ<br>IANEINVNPEDIKGYRITKSGKPQFTEFKLYHDLKSVLFDQSILENEDVLDQIAEILTIY<br>QDKDSIKSKLTELDILLNEEDKENIAQLTGYTGTHRLSLKCIRLVLEEQWYSSANQMEIF<br>THLNIKPKKINLTAANKIPKAMIDEFILSPVVKRTFGQAINLINKIIEKYGVPEDIIIEL<br>ARENNSKDKQKFINEMQKKNENTRKRINEIIGKYGNQNAKRLVEKIRLHDEQEGKCLYSL<br>ESIPLEDLLNNPNHYEVDHIIPRSVSFDNSYHNKVLVKQSENSKKSNLTPYQYFNSGKSK<br>LSYNQFKQHILNLSKSQDRISKKKKEYLLEERDINKFEVQKEFINRNLVDTRYATRELTN<br>YLKAYFSANNMNVKVKTINGSFTDYLRKVWKFKKERNHGYKHHAEDALIIANADFLFKEN<br>KKLKAVNSVLEKPEIETKQLDIQVDSEDNYSEMFIIPKQVQDIKDFRNFKYSHRVDKKPN<br>RQLINDTLYSTRKKDNSTYIVQTIKDIYAKDNTTLKKQFDKSPEKFLMYQHDPRTFEKLE<br>VIMKQYANEKNPLAKYHEETGEYLTKYSKKNNGPIVKSLKYIGNKLGSHLDVTHQFKSST | M-<br>SluCas9R414A |

-continued

SEQUENCE LISTING

| SEQ ID NO | Sequence | Description |
|---|---|---|
| | KKLVKLSIKPYRFDVYLTDKGYKFITISYLDVLKKDNYYYIPEQKYDKLKLGKAIDKNAK<br>FIASFYKNDLIKLDGEIYKIIGVNSDTRNMIELDLPDIRYKEYCELNNIKGEPRIKKTIG<br>KKVNSIEKLTTDVLGNVFTNTQYTKPQLLFKRGNGG | |
| 8 | MNQKFILGLDIGITSVGYGLIDYETKNIIDAGVRLFPEANVENNEGRRSKRGSRRLKRRR<br>IHRLERVKLLLTEYDLINKEQIPTSNNPYQIRVKGLSEILSKDELAIALLHLAKRRGIHN<br>VDVAADKEETASDSLSTKDQINKNAKFLESRYVCELQKERLENEGHVRGVENRFLTKDIV<br>REAKKIIDTQMQYYPEIDETFKEKYISLVETRREYFEGPGQGSPFGWNGDLKKWYEMLMG<br>HCTYFPQELRSVKYAYSADLFNALNDLNNLIIQRDNSEKLEYHEKYHIIENVFKQKKKPT<br>LKQIAKEIGVNPEDIKGYRITKSGTPEFTSFKLFHDLKKVVKDHAILDDIDLLNQIAEIL<br>TIYQDKDSIVAELGQLEYLMSEADKQSISELTGYTGTHSLSLKCMNMIIDALWHSSMNQM<br>EVFTYLNMRPKKYELKGYQRIPTDMIDDAILSPVVKRTFIQSINVINKVIEKYGIPEDII<br>IELARENNSDDRKKFINNLQKKNEATRKRINEIIGQTGNQNAKRIVEKIRLHDQQEGKCL<br>YSLESIPLEDLLNNPNHYEVDHIIPRSVSFDNSYHNKVLVKQSENSKKSNLTPYQYFNSG<br>KSKLSYNQFKQHILNLSKSQDRISKKKKEYLLEERDINKFEVQKEFINRNLVDTRYATRE<br>LTSYLKAYFSANNMDVKVKTINGSFTNHLRKVWRFDKYRNHGYKHHAEDALIIANADFLF<br>KENKKLQNTNKILEKPTIENNTKKVTVEKEEDYNNVFETPKLVEDIKQYRDYKFSHRVDK<br>KPNRQLINDTLYSTRMKDEHDYIVQTITDIYGKDNTNLKKQFNKNPEKFLMYQNDPKTFE<br>KLSIIMKQYSDEKNPLAKYYEETGEYLTKYSKKNNGPIVKKIKLLGNKVGNHLDVTNKYE<br>NSTKKLVKLSIKNYRFDVYLTEKGYKFVTIAYLNVFKKDNYYYIPKDKYQELKEKKKIKD<br>TDQFIASFYKNDLIKLNGDLYKIIGVNSDDRNIIELDYYDIKYKDYCEINNIKGEPRIKK<br>TIGKKTESIEKFTTDVLGNLYLHSTEKAPQLIFKRGL | MGib11SpaCas9-3E410A |
| 9 | MNQKFILGLDIGITSVGYGLIDYETKNIIDAGVRLFPEANVENNEGRRSKRGSRRLKRRR<br>IHRLERVKKLLEDYNLLDQSQIPQSTNPYAIRVKGLSEALSKDELVIALLHIAKRRGIHK<br>IDVIDSNDDVGNELSTKEQLNKNSKLLKDKFVCQIQLERMNEGQVRGEKNRFKTADIIKE<br>IIQLLNVQKNFHQLDENFINKYIELVEMRREYFEGPGKGSPYGWEGDPKAWYETLMGHCT<br>YFPDELRSVKYAYSADLFNALNDLNNLVIQRDGLSKLEYHEKYHIIENVFKQKKKPTLKQ<br>IANEINVNPEDIKGYRITKSGKPQFTEFKLYHDLKSVLFDQSILENEDVLDQIAEILTIY<br>QDKDSIKSKLTELDILLNEEDKENIAQLTGYTGTHRLSLKCIRLVLEEQWYSSRNQMEIF<br>THLNIKPKKINLTAANKIPKAMIDEFILSPVVKRTFGQAINLINKIIEKYGVPEDIIIEL<br>ARENNSKDKQKFINEMQKKNENTRKRINEIIGKYGNQNAKRLVEKIRLHDEQEGKCLYSL<br>ESIPLEDLLNNPNHYEVDHIIPRSVSFDNSYHNKVLVKQSENSKKSNLTPYQYFNSGKSK<br>LSYNQFKQHILNLSKSQDRISKKKKEYLLEERDINKFEVQKEFINRNLVDTRYATRELTN<br>YLKAYFSANNMNVKVKTINGSFTDYLRKVWKFKKERNHGYKHHAEDALIIANADFLFKEN<br>KKLKAVNSVLEKPEIETKQLDIQVDSEDNYSEMFIIPKQVQDIKDFRNFKYSHRVDKKPN<br>RQLINDTLYSTRKKDNSTYIVQTIKDIYAKDNTTLKKQFDKSPEKFLMYQHDPRTFEKLE<br>VIMKQYANEKNPLAKYHEETGEYLTKYSKKNNGPIVKSLKYIGNKLGSHLDVTHQFKSST<br>KKLVKLSIKPYRFDVYLTDKGYKFITISYLDVLKKDNYYYIPEQKYDKLKLGKAIDKNAK<br>FIASFYKNDLIKLDGEIYKIIGVNSDTRNMIELDLPDIRYKEYCELNNIKGEPRIKKTIG<br>KKVNSIEKLTTDVLGNVFTNTQYTKPQLLFKRGNGG | SluCas9 |
| 10 | ggugaacguggaugaaguugguuuuaguacucuggaaacagaaucuacugaaacaagacaa<br>uaugucguguuuaucccaucaauuuauuggugggauuuuuuucuagcauaaccccuugggg<br>ccucuaaacgggucuugagggguuuuuu | sgRNA_Ex1 |
| 11 | ggtgaacgtggatgaagttgtggggtac | R01-1-A |
| 12 | gcggtaccccacaacttcatccacgttcaccgg | R01-1-B |
| 13 | agtgaacgtggatgaagttgtggggtac | R01-2-A |
| 14 | gcggtaccccacaacttcatccacgttcactgg | R01-243 |
| 15 | cgtgaacgtggatgaagttgtggggtac | R01-3-A |
| 16 | gcggtaccccacaacttcatccacgttcacggg | R01-3-B |
| 17 | tgtgaacgtggatgaagttgtggggtac | R01-4-A |
| 18 | gcggtaccccacaacttcatccacgttcacagg | R01-4-B |
| 19 | gatgaacgtggatgaagttgtggggtac | R01-5-A |
| 20 | gcggtaccccacaacttcatccacgttcatcgg | R01-5-B |
| 21 | gctgaacgtggatgaagttgtggggtac | R01-6-A |
| 22 | gcggtaccccacaacttcatccacgttcagcgg | R01-6-B |
| 23 | gttgaacgtggatgaagttgtggggtac | R01-7-A |
| 24 | gcggtaccccacaacttcatccacgttcaacgg | R01-7-B |

-continued

SEQUENCE LISTING

| SEQ ID NO | Sequence | Description |
|---|---|---|
| 25 | ggagaacgtggatgaagttgtggggtac | R01-8-A |
| 26 | gcggtaccccacaacttcatccacgttctccgg | R01-8-B |
| 27 | ggcgaacgtggatgaagttgtggggtac | R01-9-A |
| 28 | gcggtaccccacaacttcatccacgttcgccgg | R01-9-B |
| 29 | ggggaacgtggatgaagttgtggggtac | R01-10-A |
| 30 | gcggtaccccacaacttcatccacgttccccgg | R01-10-B |
| 31 | ggtaaacgtggatgaagttgtggggtac | R01-11-A |
| 32 | gcggtaccccacaacttcatccacgtttaccgg | R01-11-B |
| 33 | ggtcaacgtggatgaagttgtggggtac | R01-12-A |
| 34 | gcggtaccccacaacttcatccacgttgaccgg | R01-12-B |
| 35 | ggttaacgtggatgaagttgtggggtac | R01-13-A |
| 36 | gcggtaccccacaacttcatccacgttaaccgg | R01-13-B |
| 37 | ggtgcacgtggatgaagttgtggggtac | R01-14-A |
| 38 | gcggtaccccacaacttcatccacgtgcaccgg | R01-14-B |
| 39 | ggtgtacgtggatgaagttgtggggtac | R01-15-A |
| 40 | gcggtaccccacaacttcatccacgtacaccgg | R01-15-B |
| 41 | ggtggacgtggatgaagttgtggggtac | R01-16-A |
| 42 | gcggtaccccacaacttcatccacgtccaccgg | R01-16-B |
| 43 | ggtgaccgtggatgaagttgtggggtac | R01-17-A |
| 44 | gcggtaccccacaacttcatccacggtcaccgg | R01-17-B |
| 45 | ggtgatcgtggatgaagttgtggggtac | R01-18-A |
| 46 | gcggtaccccacaacttcatccacgatcaccgg | R01-18-B |
| 47 | ggtgagcgtggatgaagttgtggggtac | R01-19-A |
| 48 | gcggtaccccacaacttcatccacgctcaccgg | R01-19-B |
| 49 | ggtgaaagtggatgaagttgtggggtac | R01-20-A |
| 50 | gcggtaccccacaacttcatccactttcaccgg | R01-20-B |
| 51 | ggtgaatgtggatgaagttgtggggtac | R01-21-A |
| 52 | gcggtaccccacaacttcatccacattcaccgg | R01-21-B |
| 53 | ggtgaaggtggatgaagttgtggggtac | R01-22-A |
| 54 | gcggtaccccacaacttcatccaccttcaccgg | R01-22-B |
| 55 | ggtgaacatggatgaagttgtggggtac | R01-23-A |
| 56 | gcggtaccccacaacttcatccatgttcaccgg | R01-23-B |
| 57 | ggtgaacctggatgaagttgtggggtac | R01-24-A |
| 58 | gcggtaccccacaacttcatccaggttcaccgg | R01-24-B |
| 59 | ggtgaacttggatgaagttgtggggtac | R01-25-A |
| 60 | gcggtaccccacaacttcatccaagttcaccgg | R01-25-B |
| 61 | ggtgaacgaggatgaagttgtggggtac | R01-26-A |

-continued

SEQUENCE LISTING

| SEQ ID NO | Sequence | Description |
| --- | --- | --- |
| 62 | gcggtaccccacaacttcatcctcgttcaccgg | R01-26-B |
| 63 | ggtgaacgcggatgaagttgtggggtac | R01-27-A |
| 64 | gcggtaccccacaacttcatccgcgttcaccgg | R01-27-B |
| 65 | ggtgaacggggatgaagttgtggggtac | R01-28-A |
| 66 | gcggtaccccacaacttcatccccgttcaccgg | R01-28-B |
| 67 | ggtgaacgtagatgaagttgtggggtac | R01-29-A |
| 68 | gcggtaccccacaacttcatctacgttcaccgg | R01-29-B |
| 69 | ggtgaacgtcgatgaagttgtggggtac | R01-30-A |
| 70 | gcggtaccccacaacttcatcgacgttcaccgg | R01-30-B |
| 71 | ggtgaacgttgatgaagttgtggggtac | R01-31-A |
| 72 | gcggtaccccacaacttcatcaacgttcaccgg | R01-31-B |
| 73 | ggtgaacgtgaatgaagttgtggggtac | R01-32-A |
| 74 | gcggtaccccacaacttcattcacgttcaccgg | R01-32-B |
| 75 | ggtgaacgtgcatgaagttgtggggtac | R01-33-A |
| 76 | gcggtaccccacaacttcatgcacgttcaccgg | R01-33-B |
| 77 | ggtgaacgtgtatgaagttgtggggtac | R01-34-A |
| 78 | gcggtaccccacaacttcatacacgttcaccgg | R01-34-B |
| 79 | ggtgaacgtggctgaagttgtggggtac | R01-35-A |
| 80 | gcggtaccccacaacttcagccacgttcaccgg | R01-35-B |
| 81 | ggtgaacgtggttgaagttgtggggtac | R01-36-A |
| 82 | gcggtaccccacaacttcaaccacgttcaccgg | R01-36-B |
| 83 | ggtgaacgtgggtgaagttgtggggtac | R01-37-A |
| 84 | gcggtaccccacaacttcacccacgttcaccgg | R01-37-B |
| 85 | ggtgaacgtggaagaagttgtggggtac | R01-38-A |
| 86 | gcggtaccccacaacttcttccacgttcaccgg | R01-38-B |
| 87 | ggtgaacgtggacgaagttgtggggtac | R01-39-A |
| 88 | gcggtaccccacaacttcgtccacgttcaccgg | R01-39-B |
| 89 | ggtgaacgtggaggaagttgtggggtac | R01-40-A |
| 90 | gcggtaccccacaacttcctccacgttcaccgg | R01-40-B |
| 91 | ggtgaacgtggataaagttgtggggtac | R01-41-A |
| 92 | gcggtaccccacaactttatccacgttcaccgg | R01-41-B |
| 93 | ggtgaacgtggatcaagttgtggggtac | R01-42-A |
| 94 | gcggtaccccacaacttgatccacgttcaccgg | R01-42-B |
| 95 | ggtgaacgtggattaagttgtggggtac | R01-43-A |
| 96 | gcggtaccccacaacttaatccacgttcaccgg | R01-43-B |
| 97 | ggtgaacgtggatgcagttgtggggtac | R01-44-A |
| 98 | gcggtaccccacaactgcatccacgttcaccgg | R01-44-B |

-continued

SEQUENCE LISTING

| SEQ ID NO | Sequence | Description |
|---|---|---|
| 99 | ggtgaacgtggatgtagttgtggggtac | R01-45-A |
| 100 | gcggtaccccacaactacatccacgttcaccgg | R01-45-B |
| 101 | ggtgaacgtggatggagttgtggggtac | R01-46-A |
| 102 | gcggtaccccacaactccatccacgttcaccgg | R01-46-B |
| 103 | ggtgaacgtggatgacgttgtggggtac | R01-47-A |
| 104 | gcggtaccccacaacgtcatccacgttcaccgg | R01-47-B |
| 105 | ggtgaacgtggatgatgttgtggggtac | R01-48-A |
| 106 | gcggtaccccacaacatcatccacgttcaccgg | R01-48-B |
| 107 | ggtgaacgtggatgaggttgtggggtac | R01-49-A |
| 108 | gcggtaccccacaacctcatccacgttcaccgg | R01-49-B |
| 109 | ggtgaacgtggatgaaattgtggggta | R01-50-A |
| 110 | gcggtaccccacaatttcatccacgttcaccgg | R01-50-B |
| 111 | ggtgaacgtggatgaacttgtggggtac | R01-51-A |
| 112 | gcggtaccccacaagttcatccacgttcaccgg | R01-51-B |
| 113 | ggtgaacgtggatgaatttgtggggtac | R01-52-A |
| 114 | gcggtaccccacaaattcatccacgttcaccgg | R01-52-B |
| 115 | ggtgaacgtggatgaagatgtggggtac | R01-53-A |
| 116 | gcggtaccccacatcttcatccacgttcaccgg | R01-53-B |
| 117 | ggtgaacgtggatgaagctgtggggtac | R01-54-A |
| 118 | gcggtaccccacagcttcatccacgttcaccgg | R01-54-B |
| 119 | ggtgaacgtggatgaaggtgtggggtac | R01-55-A |
| 120 | gcggtaccccacaccttcatccacgttcaccgg | R01-55-B |
| 121 | ggtgaacgtggatgaagtagtggggtac | R01-56-A |
| 122 | gcggtaccccactacttcatccacgttcaccgg | R01-56-B |
| 123 | ggtgaacgtggatgaagtcgtggggtac | R01-57-A |
| 124 | gcggtaccccacgacttcatccacgttcaccgg | R01-57-B |
| 125 | ggtgaacgtggatgaagtggtggggtac | R01-58-A |
| 126 | gcggtaccccaccacttcatccacgttcaccgg | R01-58-B |
| 127 | ggtgaacgtggatgaagttatggggtac | R01-59-A |
| 128 | gcggtaccccataacttcatccacgttcaccgg | R01-59-B |
| 129 | ggtgaacgtggatgaagttctggggtac | R01-60-A |
| 130 | gcggtaccccagaacttcatccacgttcaccgg | R01-60-B |
| 131 | ggtgaacgtggatgaagttttggggtac | R01-61-A |
| 132 | gcggtaccccaaaacttcatccacgttcaccgg | R01-61-B |
| 133 | MNQKFILGLDIGITSVGYGLIDYETKNIIDAGVRLFPEANVENNEGRRSKRGSRRLKRRR<br>IHRLERVKLLLTEYDLINKEQIPTSNNPYQIRVKGLSEILSKDELAIALLHLAKRRGIHN<br>VDVAADKEETASDSLSTKDQINKNAKFLESRYVCELQKERLENEGHVRGVENRFLTKDIV<br>REAKKIIDTQMQYYPEIDETFKEKYISLVETRREYFEGPGQGSPFGWNGDLKKWYEMLMG<br>HCTYFPQELRSVKYAYSADLFNALNDLNNLIIQRDNSEKLEYHEKYHIIENVFKQKKKPT<br>LKQIAKEIGVNPEDIKGYRITKSGTPEFTSFKLFHDLKKVVKDHAILDDIDLLNQIAEIL | Gib11SpaCas9-1-M417L |

-continued

SEQUENCE LISTING

| SEQ ID NO | Sequence | Description |
|---|---|---|
| | TIYQDKDSIVAELGQLEYLMSEADKQSISELTGYTGTHSLSLKCMNMIIDELWHSSLNQM<br>EVFTYLNMRPKKYELKGYQRIPTDMIDDAILSPVVKRTFIQSINVINKVIEKYGIPEDII<br>IELARENNSDDRKKFINNLQKKNEATRKRINEIIGQTGNQNAKRIVEKIRLHDQQEGKCL<br>YSLESIPLEDLLNNPNHYEVDHIIPRSVSFDNSYHNKVLVKQSENSKKSNLTPYQYFNSG<br>KSKLSYNQFKQHILNLSKSQDRISKKKKEYLLEERDINKFEVQKEFINRNLVDTRYATRE<br>LTNYLKAYFSANNMNVKVKTINGSFTDYLRKVWKFKKERNHGYKHHAEDALIIANADFLF<br>KENKKLKAVNSVLEKPEIETKQLDIQVDSEDNYSEMFIIPKQVQDIKDFRNFKYSHRVDK<br>KPNRQLINDTLYSTRKKDNSTYIVQTIKDIYAKDNTTLKKQFDKSPEKFLMYQHDPRTFE<br>KLEVIMKQYANEKNPLAKYHEETGEYLTKYSKKNNGPIVKSLKYIGNKLGSHLDVTHQFK<br>SSTKKLVKLSIKNYRFDVYLTEKGYKFVTIAYLNVFKKDNYYYIPKDKYQELKEKKKIKD<br>TDQFIASFYKNDLIKLNGDLYKIIGVNSDDRNIIELDYYDIKYKDYCEINNIKGEPRIKK<br>TIGKKTESIEKFTTDVLGNLYLHSTEKAPQLIFKRGL | |

What is claimed is:

1. An M-SmallCas9 polypeptide, wherein the M-SmallCas9 polypeptide is at least 95% identical to SEQ ID NO. 8 and wherein the polypeptide at least 95% identical to SEQ ID NO:8 comprises an E410A mutation, or wherein the M-SmallCas9 polypeptide is at least 95% identical to SEQ ID NO. 133, wherein the polypeptide at least 95% identical to SEQ ID NO: 133 comprises an M417L mutation.

2. A composition comprising (I) an M-SmallCas9 polypeptide of claim 1; and (II) one or more single guide RNA(s) (sgRNA) or DNA(s) that allow the generation of such one or more sgRNA (s) in situ, each sgRNA or DNA encoding an sgRNA comprising:

(a) an engineered DNA targeting segment that can hybridize to a target sequence in a polynucleotide locus, (b) a tracr mate sequence, and (c) a tracr RNA sequence, wherein the tracr mate sequence can hybridize to the tracr sequence, and wherein (a), (b), and (c) are arranged in a 5' to 3' orientation.

3. The composition of claim 2, wherein the engineered DNA targeting segment has a 3' end or portion and the engineered DNA targeting segment is directly adjacent to a PAM sequence on the 3' end or such PAM sequence is part of the DNA targeting sequence in the 3' portion.

4. A method of targeting, editing, modifying, or manipulating a target DNA at one or more locations in a cell or in vitro, the method comprising (I) introducing a heterologous M-SmallCas9 polypeptide of claim 1 or a nucleic acid encoding an M-SmallCas9 of claim 1 into the cell or into the in vitro environment; and (II) introducing one or more single guide RNA(s) (sgRNA) or DNA(s) encoding such one or more sgRNA(s) in the cell or the in vitro environment, each sgRNA or DNA encoding the sgRNA comprising:

(a) an engineered DNA targeting segment comprising an RNA and capable of hybridizing to a target sequence in a polynucleotide locus, (b) a tracr mate sequence comprised of RNA, and (c) a tracr RNA sequence comprised of RNA, wherein the tracr mate sequence hybridizes to the tracr sequence, and wherein (a), (b), and (c) are arranged in a 5' to 3' orientation; and (III) creating one or more nicks or cuts or base edits in the target DNA, wherein the M-SmallCas9 polypeptide is directed to the target DNA by the sgRNA.

5. A cell comprising (I) an M-SmallCas9 polypeptide of claim 1, or a nucleic acid encoding an M-SmallCas9 polypeptide of claim 1; and (II) one or more single guide RNA(s) (sgRNA) or DNA(s) suitable for the generation of such one or more sgRNA in situ, each comprising:

(a) an engineered DNA targeting segment that can hybridizing to a target sequence in a polynucleotide locus, (b) a tracr mate sequence, and (c) a tracr RNA sequence, wherein the tracr mate sequence that can hybridize to the tracr sequence, and wherein (a), (b), and (c) are arranged in a 5' to 3' orientation.

6. A kit comprising (I) a nucleic acid sequence encoding an M-SmallCas9 polypeptide of claim 1, wherein the nucleic acid sequence encoding the M-SmallCas9 is operably linked to a promoter; and (II) one or more single guide RNA(s) (sgRNA) or DNA(s) suitable for the generation of such one or more sgRNA in situ, each sgRNA comprising:

(a) an engineered DNA targeting segment that can hybridize to a target sequence in a polynucleotide locus, (b) a tracr mate sequence, and (c) a tracr RNA sequence, wherein the tracr mate sequence can hybridize to the tracr sequence, and wherein (a), (b), and (c) are arranged in a 5' to 3' orientation.

* * * * *

SEQUENCE LISTING

<160> NUMBER OF SEQ ID NOS: 133

<210> SEQ ID NO 1
<211> LENGTH: 1053
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: The sequence CANNOT be where X equals the following combination - 406: E, 412: D, 416: A, and 420: R
<220> FEATURE:
<221> NAME/KEY: misc_feature
<222> LOCATION: (1)..(1053)
<223> OTHER INFORMATION: M-SauCas9_X
<220> FEATURE:
<221> NAME/KEY: misc_feature
<222> LOCATION: (406)..(406)
<223> OTHER INFORMATION: X can be any of these amino acids: E, G,S,T,A, D
<220> FEATURE:
<221> NAME/KEY: misc_feature
<222> LOCATION: (412)..(412)
<223> OTHER INFORMATION: X can be any of these amino acids: D, G,S,T,A, E
<220> FEATURE:
<221> NAME/KEY: misc_feature
<222> LOCATION: (416)..(416)
<223> OTHER INFORMATION: X can be any of these amino acids: A, G, S, T, D, E
<220> FEATURE:
<221> NAME/KEY: misc_feature
<222> LOCATION: (420)..(420)
<223> OTHER INFORMATION: X can be any of these amino acids: R, A, G, S, T, D, E

<400> SEQUENCE: 1

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
```

-continued

```
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Xaa Leu Trp His Thr Asn Xaa Asn Gln Ile Xaa
                405                 410                 415

Ile Phe Asn Xaa Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510
```

-continued

```
Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925
```

```
Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020

Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050


<210> SEQ ID NO 2
<211> LENGTH: 1056
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: The sequence CANNOT be where X equals the
      following combination - 408: E, 414: R, 418: E, 422: H, 239: C,
      and 401: C
<220> FEATURE:
<221> NAME/KEY: misc_feature
<222> LOCATION: (1)..(1056)
<223> OTHER INFORMATION: M-SluCas9_x
<220> FEATURE:
<221> NAME/KEY: misc_feature
<222> LOCATION: (239)..(239)
<223> OTHER INFORMATION: X can be any of these amino acids:  C,  S, A
<220> FEATURE:
<221> NAME/KEY: misc_feature
<222> LOCATION: (401)..(401)
<223> OTHER INFORMATION: X can be any of these amino acids: C,  S, A
<220> FEATURE:
<221> NAME/KEY: misc_feature
<222> LOCATION: (408)..(408)
<223> OTHER INFORMATION: X can be any of these amino acids:  E, G,S,T,A,
      D
<220> FEATURE:
<221> NAME/KEY: misc_feature
<222> LOCATION: (414)..(414)
<223> OTHER INFORMATION: X can be any of these amino acids:  R, G,S,T,A,
      D, E
<220> FEATURE:
<221> NAME/KEY: misc_feature
<222> LOCATION: (418)..(418)
<223> OTHER INFORMATION: X can be any of these amino acids:  E, G, S, T,
      A, D
<220> FEATURE:
<221> NAME/KEY: misc_feature
<222> LOCATION: (422)..(422)
<223> OTHER INFORMATION: X can be any of these amino acids:  H,  A, G,
      S, T, D, E

<400> SEQUENCE: 2

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45
```

-continued

```
Ser Lys Arg Gly Ser Arg Arg Leu Lys Arg Arg Arg Ile His Arg Leu
    50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
            100                 105                 110

Ala Lys Arg Arg Gly Ile His Lys Ile Asp Val Ile Asp Ser Asn Asp
        115                 120                 125

Asp Val Gly Asn Glu Leu Ser Thr Lys Glu Gln Leu Asn Lys Asn Ser
    130                 135                 140

Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Gly Lys Gly Ser Pro Tyr Gly Trp
    210                 215                 220

Glu Gly Asp Pro Lys Ala Trp Tyr Glu Thr Leu Met Gly His Xaa Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
    290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
        355                 360                 365

Lys Leu Thr Glu Leu Asp Ile Leu Leu Asn Glu Glu Asp Lys Glu Asn
    370                 375                 380

Ile Ala Gln Leu Thr Gly Tyr Thr Gly Thr His Arg Leu Ser Leu Lys
385                 390                 395                 400

Xaa Ile Arg Leu Val Leu Glu Xaa Gln Trp Tyr Ser Ser Xaa Asn Gln
                405                 410                 415

Met Xaa Ile Phe Thr Xaa Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
    450                 455                 460
```

-continued

```
Lys Ile Ile Glu Lys Tyr Gly Val Pro Glu Asp Ile Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
        515                 520                 525

His Asp Glu Gln Glu Gly Lys Cys Leu Tyr Ser Leu Glu Ser Ile Pro
    530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
        675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
    770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815

Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
        835                 840                 845

Glu Lys Asn Pro Leu Ala Lys Tyr His Glu Glu Thr Gly Glu Tyr Leu
    850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
```

-continued

```
                885                 890                 895

Lys Ser Ser Thr Lys Lys Leu Val Lys Leu Ser Ile Lys Pro Tyr Arg
            900                 905                 910

Phe Asp Val Tyr Leu Thr Asp Lys Gly Tyr Lys Phe Ile Thr Ile Ser
        915                 920                 925

Tyr Leu Asp Val Leu Lys Lys Asp Asn Tyr Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
            980                 985                 990

Leu Asp Leu Pro Asp Ile Arg Tyr  Lys Glu Tyr Cys Glu  Leu Asn Asn
        995                 1000                1005

Ile Lys  Gly Glu Pro Arg Ile  Lys Lys Thr Ile Gly  Lys Lys Val
    1010                1015                1020

Asn Ser  Ile Glu Lys Leu Thr  Thr Asp Val Leu Gly  Asn Val Phe
    1025                1030                1035

Thr Asn  Thr Gln Tyr Thr Lys  Pro Gln Leu Leu Phe  Lys Arg Gly
    1040                1045                1050

Asn Gly  Gly
    1055
```

```
<210> SEQ ID NO 3
<211> LENGTH: 1054
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: The sequence CANNOT be where X equals the
      following combination - 408:E, 414: R, 418: E, 422: Y, 239: C, and
      401:C
<220> FEATURE:
<221> NAME/KEY: misc_feature
<222> LOCATION: (1)..(1054)
<223> OTHER INFORMATION: M-SpaCas9_X
<220> FEATURE:
<221> NAME/KEY: misc_feature
<222> LOCATION: (239)..(239)
<223> OTHER INFORMATION: X can be any of these amino acids:  C,  S, A
<220> FEATURE:
<221> NAME/KEY: misc_feature
<222> LOCATION: (401)..(401)
<223> OTHER INFORMATION: X can be any of these amino acids:  C,  S, A
<220> FEATURE:
<221> NAME/KEY: misc_feature
<222> LOCATION: (408)..(408)
<223> OTHER INFORMATION: X can be any of these amino acids:  E, G,S,T,A,
      D
<220> FEATURE:
<221> NAME/KEY: misc_feature
<222> LOCATION: (414)..(414)
<223> OTHER INFORMATION: X can be any of these amino acids:  R, G,S,T,A,
      D, E
<220> FEATURE:
<221> NAME/KEY: misc_feature
<222> LOCATION: (418)..(418)
<223> OTHER INFORMATION: X can be any of these amino acids:  E, G, S, T,
      A, D
<220> FEATURE:
<221> NAME/KEY: misc_feature
<222> LOCATION: (422)..(422)
<223> OTHER INFORMATION: X can be any of these amino acids:  Y, A, G, S,
      T, D, E
```

<400> SEQUENCE: 3

```
Met Lys Glu Lys Tyr Ile Leu Gly Leu Asp Leu Gly Ile Thr Ser Val
1               5                   10                  15

Gly Tyr Gly Ile Ile Asn Phe Glu Thr Lys Lys Ile Ile Asp Ala Gly
            20                  25                  30

Val Arg Leu Phe Pro Glu Ala Asn Val Asp Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Ile Asn Val Ser Ser Glu Asp Glu
        115                 120                 125

Asp Ala Ser Asn Glu Leu Ser Thr Lys Glu Gln Ile Asn Arg Asn Asn
    130                 135                 140

Lys Leu Leu Lys Asp Lys Tyr Val Cys Glu Val Gln Leu Gln Arg Leu
145                 150                 155                 160

Lys Glu Gly Gln Ile Arg Gly Glu Lys Asn Arg Phe Lys Thr Thr Asp
                165                 170                 175

Ile Leu Lys Glu Ile Asp Gln Leu Leu Lys Val Gln Lys Asp Tyr His
            180                 185                 190

Asn Leu Asp Ile Asp Phe Ile Asn Gln Tyr Lys Glu Ile Val Glu Thr
        195                 200                 205

Arg Arg Glu Tyr Phe Glu Gly Pro Gly Gln Gly Ser Pro Phe Gly Trp
    210                 215                 220

Asn Gly Asp Leu Lys Lys Trp Tyr Glu Met Leu Met Gly His Xaa Thr
225                 230                 235                 240

Tyr Phe Pro Gln Glu Leu Arg Ser Val Lys Tyr Ala Tyr Ser Ala Asp
                245                 250                 255

Leu Phe Asn Ala Leu Asn Asp Leu Asn Asn Leu Ile Ile Gln Arg Asp
            260                 265                 270

Asn Ser Glu Lys Leu Glu Tyr His Glu Lys Tyr His Ile Ile Glu Asn
        275                 280                 285

Val Phe Lys Gln Lys Lys Lys Pro Thr Leu Lys Gln Ile Ala Lys Glu
    290                 295                 300

Ile Gly Val Asn Pro Glu Asp Ile Lys Gly Tyr Arg Ile Thr Lys Ser
305                 310                 315                 320

Gly Thr Pro Gln Phe Thr Glu Phe Lys Leu Tyr His Asp Leu Lys Ser
                325                 330                 335

Ile Val Phe Asp Lys Ser Ile Leu Glu Asn Glu Ala Ile Leu Asp Gln
            340                 345                 350

Ile Ala Glu Ile Leu Thr Ile Tyr Gln Asp Glu Gln Ser Ile Lys Glu
        355                 360                 365

Glu Leu Asn Lys Leu Pro Glu Ile Leu Asn Glu Gln Asp Lys Ala Glu
    370                 375                 380

Ile Ala Lys Leu Ile Gly Tyr Asn Gly Thr His Arg Leu Ser Leu Lys
385                 390                 395                 400

Xaa Ile His Leu Ile Asn Glu Xaa Leu Trp Gln Thr Ser Xaa Asn Gln
```

```
                405                 410                 415

Met Xaa Ile Phe Asn Xaa Leu Asn Ile Lys Pro Asn Lys Val Asp Leu
            420                 425                 430

Ser Glu Gln Asn Lys Ile Pro Lys Asp Met Val Asn Asp Phe Ile Leu
        435                 440                 445

Ser Pro Val Val Lys Arg Thr Phe Ile Gln Ser Ile Asn Val Ile Asn
    450                 455                 460

Lys Val Ile Glu Lys Tyr Gly Ile Pro Glu Asp Ile Ile Ile Glu Leu
465                 470                 475                 480

Ala Arg Glu Asn Asn Ser Asp Asp Arg Lys Lys Phe Ile Asn Asn Leu
                485                 490                 495

Gln Lys Lys Asn Glu Ala Thr Arg Lys Arg Ile Asn Glu Ile Ile Gly
            500                 505                 510

Gln Thr Gly Asn Gln Asn Ala Lys Arg Ile Val Glu Lys Ile Arg Leu
        515                 520                 525

His Asp Gln Gln Glu Gly Lys Cys Leu Tyr Ser Leu Glu Ser Ile Ala
    530                 535                 540

Leu Met Asp Leu Leu Asn Asn Pro Gln Asn Tyr Glu Val Asp His Ile
545                 550                 555                 560

Ile Pro Arg Ser Val Ala Phe Asp Asn Ser Ile His Asn Lys Val Leu
                565                 570                 575

Val Lys Gln Ile Glu Asn Ser Lys Lys Gly Asn Arg Thr Pro Tyr Gln
            580                 585                 590

Tyr Leu Asn Ser Ser Asp Ala Lys Leu Ser Tyr Asn Gln Phe Lys Gln
        595                 600                 605

His Ile Leu Asn Leu Ser Lys Ser Lys Asp Arg Ile Ser Lys Lys Lys
    610                 615                 620

Lys Asp Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Ser Tyr Leu Lys Ala Tyr Phe Ser Ala Asn Asn Met Asp
            660                 665                 670

Val Lys Val Lys Thr Ile Asn Gly Ser Phe Thr Asn His Leu Arg Lys
        675                 680                 685

Val Trp Arg Phe Asp Lys Tyr Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Gln Asn Thr Asn Lys Ile Leu Glu Lys Pro Thr Ile Glu
                725                 730                 735

Asn Asn Thr Lys Lys Val Thr Val Glu Lys Glu Glu Asp Tyr Asn Asn
            740                 745                 750

Val Phe Glu Thr Pro Lys Leu Val Glu Asp Ile Lys Gln Tyr Arg Asp
        755                 760                 765

Tyr Lys Phe Ser His Arg Val Asp Lys Lys Pro Asn Arg Gln Leu Ile
    770                 775                 780

Asn Asp Thr Leu Tyr Ser Thr Arg Met Lys Asp Glu His Asp Tyr Ile
785                 790                 795                 800

Val Gln Thr Ile Thr Asp Ile Tyr Gly Lys Asp Asn Thr Asn Leu Lys
                805                 810                 815

Lys Gln Phe Asn Lys Asn Pro Glu Lys Phe Leu Met Tyr Gln Asn Asp
            820                 825                 830
```

```
Pro Lys Thr Phe Glu Lys Leu Ser Ile Ile Met Lys Gln Tyr Ser Asp
        835                 840                 845

Glu Lys Asn Pro Leu Ala Lys Tyr Tyr Glu Glu Thr Gly Glu Tyr Leu
    850                 855                 860

Thr Lys Tyr Ser Lys Lys Asn Asn Gly Pro Ile Val Lys Lys Ile Lys
865                 870                 875                 880

Leu Leu Gly Asn Lys Val Gly Asn His Leu Asp Val Thr Asn Lys Tyr
                885                 890                 895

Glu Asn Ser Thr Lys Lys Leu Val Lys Leu Ser Ile Lys Asn Tyr Arg
            900                 905                 910

Phe Asp Val Tyr Leu Thr Glu Lys Gly Tyr Lys Phe Val Thr Ile Ala
        915                 920                 925

Tyr Leu Asn Val Phe Lys Lys Asp Asn Tyr Tyr Tyr Ile Pro Lys Asp
    930                 935                 940

Lys Tyr Gln Glu Leu Lys Glu Lys Lys Lys Ile Lys Asp Thr Asp Gln
945                 950                 955                 960

Phe Ile Ala Ser Phe Tyr Lys Asn Asp Leu Ile Lys Leu Asn Gly Asp
                965                 970                 975

Leu Tyr Lys Ile Ile Gly Val Asn Ser Asp Asp Arg Asn Ile Ile Glu
            980                 985                 990

Leu Asp Tyr Tyr Asp Ile Lys Tyr  Lys Asp Tyr Cys Glu  Ile Asn Asn
        995                 1000                1005

Ile Lys  Gly Glu Pro Arg Ile  Lys Lys Thr Ile Gly  Lys Lys Thr
    1010                1015                1020

Glu Ser  Ile Glu Lys Phe Thr  Thr Asp Val Leu Gly  Asn Leu Tyr
    1025                1030                1035

Leu His  Ser Thr Glu Lys Ala  Pro Gln Leu Ile Phe  Lys Arg Gly
    1040                1045                1050

Leu
```

<210> SEQ ID NO 4
<211> LENGTH: 1051
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: The sequence CANNOT be where X equals the following combination - 408: D, 414: L, 418: E, 422: K, 239: C, and 401: C
<220> FEATURE:
<221> NAME/KEY: misc_feature
<222> LOCATION: (1)..(1051)
<223> OTHER INFORMATION: M-ShyCas9_X
<220> FEATURE:
<221> NAME/KEY: misc_feature
<222> LOCATION: (239)..(239)
<223> OTHER INFORMATION: X can be any of these amino acids: C, S, A
<220> FEATURE:
<221> NAME/KEY: misc_feature
<222> LOCATION: (401)..(401)
<223> OTHER INFORMATION: X can be any of these amino acids: C, S, A
<220> FEATURE:
<221> NAME/KEY: misc_feature
<222> LOCATION: (408)..(408)
<223> OTHER INFORMATION: X can be any of these amino acids: D, G,S,T,A, E
<220> FEATURE:
<221> NAME/KEY: misc_feature
<222> LOCATION: (414)..(414)
<223> OTHER INFORMATION: X can be any of these amino acids: L, G,S,T,A, D, E

```
<220> FEATURE:
<221> NAME/KEY: misc_feature
<222> LOCATION: (418)..(418)
<223> OTHER INFORMATION: X can be any of these amino acids: E, G, S, T,
      A, D
<220> FEATURE:
<221> NAME/KEY: misc_feature
<222> LOCATION: (422)..(422)
<223> OTHER INFORMATION: X can be any of these amino acids: K,  A, G, S,
      T, D, E

<400> SEQUENCE: 4

Met Asn Asn Tyr Ile Leu Gly Leu Asp Ile Gly Ile Thr Ser Val Gly
1               5                   10                  15

Tyr Gly Ile Val Asp Ser Asp Thr Arg Glu Ile Lys Asp Ala Gly Val
            20                  25                  30

Arg Leu Phe Pro Glu Ala Asn Val Asp Asn Asn Glu Gly Arg Arg Ser
        35                  40                  45

Lys Arg Gly Ala Arg Arg Leu Lys Arg Arg Arg Ile His Arg Leu Asp
    50                  55                  60

Arg Val Lys His Leu Leu Ala Glu Tyr Asp Leu Leu Asp Leu Thr Asn
65                  70                  75                  80

Ile Pro Lys Ser Thr Asn Pro Tyr Gln Thr Arg Val Lys Gly Leu Asn
                85                  90                  95

Glu Lys Leu Ser Lys Asp Glu Leu Val Ile Ala Leu Leu His Ile Ala
            100                 105                 110

Lys Arg Arg Gly Ile His Asn Val Asn Val Met Met Asp Asp Asn Asp
        115                 120                 125

Ser Gly Asn Glu Leu Ser Thr Lys Asp Gln Leu Lys Lys Asn Ala Lys
    130                 135                 140

Ala Leu Ser Asp Lys Tyr Val Cys Glu Leu Gln Leu Glu Arg Phe Glu
145                 150                 155                 160

Gln Asp Tyr Lys Val Arg Gly Glu Lys Asn Arg Phe Lys Thr Glu Asp
                165                 170                 175

Phe Val Arg Glu Ala Arg Lys Leu Leu Glu Thr Gln Ser Lys Phe Phe
            180                 185                 190

Glu Ile Asp Gln Thr Phe Ile Met Arg Tyr Ile Glu Leu Ile Glu Thr
        195                 200                 205

Arg Arg Glu Tyr Phe Glu Gly Pro Gly Lys Gly Ser Pro Phe Gly Trp
    210                 215                 220

Glu Gly Asn Ile Lys Lys Trp Phe Glu Gln Met Met Gly His Xaa Thr
225                 230                 235                 240

Tyr Phe Pro Glu Glu Leu Arg Ser Val Lys Tyr Ser Tyr Ser Ala Glu
                245                 250                 255

Leu Phe Asn Ala Leu Asn Asp Leu Asn Asn Leu Val Ile Thr Arg Asp
            260                 265                 270

Glu Asp Ala Lys Leu Asn Tyr Gly Glu Lys Phe Gln Ile Ile Glu Asn
        275                 280                 285

Val Phe Lys Gln Lys Lys Thr Pro Asn Leu Lys Gln Ile Ala Ile Glu
    290                 295                 300

Ile Gly Val His Glu Thr Glu Ile Lys Gly Tyr Arg Val Asn Lys Ser
305                 310                 315                 320

Gly Lys Pro Glu Phe Thr Gln Phe Lys Leu Tyr His Asp Leu Lys Asn
                325                 330                 335

Ile Phe Lys Asp Pro Lys Tyr Leu Asn Asp Ile Gln Leu Met Asp Asn
            340                 345                 350
```

-continued

```
Ile Ala Glu Ile Ile Thr Ile Tyr Gln Asp Ala Glu Ser Ile Ile Lys
        355                 360                 365

Glu Leu Asn Gln Leu Pro Glu Leu Leu Ser Glu Arg Glu Lys Glu Lys
    370                 375                 380

Ile Ser Ala Leu Ser Gly Tyr Ser Gly Thr His Arg Leu Ser Leu Lys
385                 390                 395                 400

Xaa Ile Asn Leu Leu Leu Asp Xaa Leu Trp Glu Ser Ser Xaa Asn Gln
            405                 410                 415

Met Xaa Leu Phe Thr Xaa Leu Asn Leu Lys Pro Lys Lys Ile Asp Leu
            420                 425                 430

Ser Gln Gln His Lys Ile Pro Ser Lys Leu Val Asp Asp Phe Ile Leu
        435                 440                 445

Ser Pro Val Val Lys Arg Ala Phe Ile Gln Ser Ile Gln Val Val Asn
    450                 455                 460

Ala Ile Ile Asp Lys Tyr Gly Leu Pro Glu Asp Ile Ile Ile Glu Leu
465                 470                 475                 480

Ala Arg Glu Asn Asn Ser Asp Asp Arg Arg Lys Phe Leu Asn Gln Leu
            485                 490                 495

Gln Lys Gln Asn Glu Glu Thr Arg Lys Gln Val Glu Lys Val Leu Arg
            500                 505                 510

Glu Tyr Gly Asn Asp Asn Ala Lys Arg Ile Val Gln Lys Ile Lys Leu
        515                 520                 525

His Asn Met Gln Glu Gly Lys Cys Leu Tyr Ser Leu Lys Asp Ile Pro
    530                 535                 540

Leu Glu Asp Leu Leu Arg Asn Pro His His Tyr Glu Val Asp His Ile
545                 550                 555                 560

Ile Pro Arg Ser Val Ala Phe Asp Asn Ser Met His Asn Lys Val Leu
            565                 570                 575

Val Arg Ala Asp Glu Asn Ser Lys Lys Gly Asn Arg Thr Pro Tyr Gln
            580                 585                 590

Tyr Leu Asn Ser Ser Glu Ser Ser Leu Ser Tyr Asn Glu Phe Lys Gln
        595                 600                 605

His Ile Leu Asn Leu Ser Lys Thr Lys Asp Arg Ile Thr Lys Lys Lys
    610                 615                 620

Arg Glu Tyr Leu Leu Glu Glu Arg Asp Ile Asn Lys Phe Asp Val Gln
625                 630                 635                 640

Lys Glu Phe Ile Asn Arg Asn Leu Val Asp Thr Arg Tyr Ala Thr Arg
            645                 650                 655

Glu Leu Thr Ser Leu Leu Lys Ala Tyr Phe Ser Ala Asn Asn Leu Asp
            660                 665                 670

Val Lys Val Lys Thr Ile Asn Gly Ser Phe Thr Asn Tyr Leu Arg Lys
        675                 680                 685

Val Trp Lys Phe Asp Lys Asp Arg Asn Lys Gly Tyr Lys His His Ala
    690                 695                 700

Glu Asp Ala Leu Ile Ile Ala Asn Ala Asp Phe Leu Phe Lys His Asn
705                 710                 715                 720

Lys Lys Leu Arg Asn Ile Asn Lys Val Leu Asp Ala Pro Ser Lys Glu
            725                 730                 735

Val Asp Lys Lys Arg Val Thr Val Gln Ser Glu Asp Glu Tyr Asn Gln
            740                 745                 750

Ile Phe Glu Asp Thr Gln Lys Ala Gln Ala Ile Lys Lys Phe Glu Ile
        755                 760                 765

Arg Lys Phe Ser His Arg Val Asp Lys Lys Pro Asn Arg Gln Leu Ile
```

-continued

```
    770                 775                 780

Asn Asp Thr Leu Tyr Ser Thr Arg Asn Ile Asp Gly Ile Glu Tyr Val
785                 790                 795                 800

Val Glu Ser Ile Lys Asp Ile Tyr Ser Val Asn Asn Asp Lys Val Lys
                805                 810                 815

Thr Lys Phe Lys Lys Asp Pro His Arg Leu Leu Met Tyr Arg Asn Asp
            820                 825                 830

Pro Gln Thr Phe Glu Lys Phe Glu Lys Val Phe Lys Gln Tyr Glu Ser
        835                 840                 845

Glu Lys Asn Pro Phe Ala Lys Tyr Tyr Glu Glu Thr Gly Glu Lys Ile
    850                 855                 860

Arg Lys Phe Ser Lys Thr Gly Gln Gly Pro Tyr Ile Asn Lys Ile Lys
865                 870                 875                 880

Tyr Leu Arg Glu Arg Leu Gly Arg His Cys Asp Val Thr Asn Lys Tyr
                885                 890                 895

Ile Asn Ser Arg Asn Lys Ile Val Gln Leu Lys Ile Tyr Ser Tyr Arg
            900                 905                 910

Phe Asp Ile Tyr Gln Tyr Gly Asn Asn Tyr Lys Met Ile Thr Ile Ser
        915                 920                 925

Tyr Ile Asp Leu Glu Gln Lys Ser Asn Tyr Tyr Tyr Ile Ser Arg Glu
    930                 935                 940

Lys Tyr Glu Gln Lys Lys Lys Asp Lys Gln Ile Asp Asp Ser Tyr Lys
945                 950                 955                 960

Phe Ile Gly Ser Phe Tyr Lys Asn Asp Ile Ile Asn Tyr Asn Gly Glu
                965                 970                 975

Met Tyr Arg Val Ile Gly Val Asn Asp Ser Glu Lys Asn Lys Ile Gln
            980                 985                 990

Leu Asp Met Ile Asp Ile Ser Ile  Lys Asp Tyr Met Glu  Leu Asn Asn
        995                 1000                1005

Ile Lys  Lys Thr Gly Val Ile  Tyr Lys Thr Ile Gly  Lys Ser Thr
    1010                1015                1020

Thr His  Ile Glu Lys Tyr Thr  Thr Asp Ile Leu Gly  Asn Leu Tyr
    1025                1030                1035

Lys Ala  Ala Pro Pro Lys Lys  Pro Gln Leu Ile Phe  Lys
    1040                1045                1050


<210> SEQ ID NO 5
<211> LENGTH: 1052
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: The sequence CANNOT be where X equals the
      following combination - 410: E, 416: M, 420: E, 424: Y, 241: C,
      and 403: C
<220> FEATURE:
<221> NAME/KEY: misc_feature
<222> LOCATION: (1)..(1052)
<223> OTHER INFORMATION: M-SmiCas9_X
<220> FEATURE:
<221> NAME/KEY: misc_feature
<222> LOCATION: (241)..(241)
<223> OTHER INFORMATION: X can be any of these amino acids: C, S, A
<220> FEATURE:
<221> NAME/KEY: misc_feature
<222> LOCATION: (403)..(403)
<223> OTHER INFORMATION: X can be any of these amino acids:  C, S, A
<220> FEATURE:
<221> NAME/KEY: misc_feature
```

```
<222> LOCATION: (410)..(410)
<223> OTHER INFORMATION: X can be any of these amino acids: E,  G, S, T,
      A, D
<220> FEATURE:
<221> NAME/KEY: misc_feature
<222> LOCATION: (416)..(416)
<223> OTHER INFORMATION: X can be any of these amino acids: M, G,S,T,A,
      D, E, L
<220> FEATURE:
<221> NAME/KEY: misc_feature
<222> LOCATION: (420)..(420)
<223> OTHER INFORMATION: X can be any of these amino acids: E, G, S, T,
      A, D
<220> FEATURE:
<221> NAME/KEY: misc_feature
<222> LOCATION: (424)..(424)
<223> OTHER INFORMATION: X can be any of these amino acids: Y,  A, G, S,
      T, D, E

<400> SEQUENCE: 5

Met Glu Lys Asp Tyr Ile Leu Gly Leu Asp Ile Gly Ile Gly Ser Val
1               5                   10                  15

Gly Tyr Gly Leu Ile Asp Tyr Asp Thr Lys Ser Ile Ile Asp Ala Gly
            20                  25                  30

Val Arg Leu Phe Pro Glu Ala Asn Ala Asp Asn Asn Leu Gly Arg Arg
        35                  40                  45

Ala Lys Arg Gly Ala Arg Arg Leu Lys Arg Arg Arg Ile His Arg Leu
    50                  55                  60

Glu Arg Val Lys Ser Leu Leu Ser Glu Tyr Lys Ile Ile Ser Gly Leu
65                  70                  75                  80

Ala Pro Thr Asn Asn Gln Pro Tyr Asn Ile Arg Val Lys Gly Leu Thr
                85                  90                  95

Glu Gln Leu Thr Lys Asp Glu Leu Ala Val Ala Leu Leu His Ile Ala
            100                 105                 110

Lys Arg Arg Gly Ile His Asn Val Asp Val Ala Ala Asp Lys Glu Glu
        115                 120                 125

Thr Ala Ser Asp Ser Leu Ser Thr Lys Asp Gln Ile Asn Lys Asn Ala
    130                 135                 140

Lys Phe Leu Glu Ser Arg Tyr Val Cys Glu Leu Gln Lys Glu Arg Leu
145                 150                 155                 160

Glu Asn Glu Gly His Val Arg Gly Val Glu Asn Arg Phe Leu Thr Lys
                165                 170                 175

Asp Ile Val Arg Glu Ala Lys Lys Ile Ile Asp Thr Gln Met Gln Tyr
            180                 185                 190

Tyr Pro Glu Ile Asp Glu Thr Phe Lys Glu Lys Tyr Ile Ser Leu Val
        195                 200                 205

Glu Thr Arg Arg Glu Tyr Tyr Glu Gly Pro Gly Lys Gly Ser Pro Tyr
    210                 215                 220

Gly Trp Asp Ala Asp Val Lys Lys Trp Tyr Gln Leu Met Met Gly His
225                 230                 235                 240

Xaa Thr Tyr Phe Pro Val Glu Phe Arg Ser Val Lys Tyr Ala Tyr Thr
                245                 250                 255

Ala Asp Leu Tyr Asn Ala Leu Asn Asp Leu Asn Asn Leu Thr Ile Ala
            260                 265                 270

Arg Asp Asp Asn Pro Lys Leu Glu Tyr His Glu Lys Tyr His Ile Ile
        275                 280                 285

Glu Asn Val Phe Lys Gln Lys Arg Asn Pro Thr Leu Lys Gln Ile Ala
    290                 295                 300

Lys Glu Ile Gly Val Asn Asp Ile Asn Ile Ser Gly Tyr Arg Val Thr
```

-continued

```
305                 310                 315                 320

Lys Ser Gly Lys Pro Gln Phe Thr Ser Phe Lys Leu Phe His Asp Leu
                325                 330                 335

Lys Lys Val Val Lys Asp His Ala Ile Leu Asp Asp Ile Asp Leu Leu
            340                 345                 350

Asn Gln Ile Ala Glu Ile Leu Thr Ile Tyr Gln Asp Lys Asp Ser Ile
        355                 360                 365

Val Ala Glu Leu Gly Gln Leu Glu Tyr Leu Met Ser Glu Ala Asp Lys
    370                 375                 380

Gln Ser Ile Ser Glu Leu Thr Gly Tyr Thr Gly Thr His Ser Leu Ser
385                 390                 395                 400

Leu Lys Xaa Met Asn Met Ile Ile Asp Xaa Leu Trp His Ser Ser Xaa
                405                 410                 415

Asn Gln Met Xaa Val Phe Thr Xaa Leu Asn Met Arg Pro Lys Lys Tyr
            420                 425                 430

Glu Leu Lys Gly Tyr Gln Arg Ile Pro Thr Asp Met Ile Asp Asp Ala
        435                 440                 445

Ile Leu Ser Pro Val Val Lys Arg Ser Phe Lys Gln Ala Ile Gly Val
    450                 455                 460

Val Asn Ala Ile Ile Lys Lys Tyr Gly Leu Pro Lys Asp Ile Ile Ile
465                 470                 475                 480

Glu Leu Ala Arg Glu Ser Asn Ser Ala Glu Lys Ser Arg Tyr Leu Arg
                485                 490                 495

Ala Ile Gln Lys Lys Asn Glu Lys Thr Arg Glu Arg Ile Glu Ala Ile
            500                 505                 510

Ile Lys Glu Tyr Gly Asn Glu Asn Ala Lys Gly Leu Val Gln Lys Ile
        515                 520                 525

Lys Leu His Asp Ala Gln Glu Gly Lys Cys Leu Tyr Ser Leu Lys Asp
    530                 535                 540

Ile Pro Leu Glu Asp Leu Leu Arg Asn Pro Asn Asn Tyr Asp Ile Asp
545                 550                 555                 560

His Ile Ile Pro Arg Ser Val Ser Phe Asp Asp Ser Met His Asn Lys
                565                 570                 575

Val Leu Val Arg Arg Glu Gln Asn Ala Lys Lys Asn Asn Gln Thr Pro
            580                 585                 590

Tyr Gln Tyr Leu Thr Ser Gly Tyr Ala Asp Ile Lys Tyr Ser Val Phe
        595                 600                 605

Lys Gln His Val Leu Asn Leu Ala Glu Asn Lys Asp Arg Met Thr Lys
    610                 615                 620

Lys Lys Arg Glu Tyr Leu Leu Glu Glu Arg Asn Ile Asn Lys Tyr Asp
625                 630                 635                 640

Val Gln Lys Glu Phe Ile Asn Arg Asn Leu Val Asp Thr Arg Tyr Thr
                645                 650                 655

Thr Arg Glu Leu Thr Thr Leu Leu Lys Thr Tyr Phe Thr Ile Asn Asn
            660                 665                 670

Leu Asp Val Lys Val Lys Thr Ile Asn Gly Ser Phe Thr Asp Phe Leu
        675                 680                 685

Arg Lys Arg Trp Gly Phe Lys Lys Asn Arg Asp Glu Gly Tyr Lys His
    690                 695                 700

His Ala Glu Asp Ala Leu Ile Ile Ala Asn Ala Asp Tyr Leu Phe Lys
705                 710                 715                 720

Glu His Lys Leu Leu Lys Glu Ile Lys Asp Val Ser Asp Leu Ala Gly
                725                 730                 735
```

```
Asp Glu Arg Asn Ser Asn Val Lys Asp Glu Asp Gln Tyr Glu Glu Val
            740                 745                 750

Phe Gly Gly Tyr Phe Lys Ile Glu Asp Ile Lys Lys Tyr Lys Ile Lys
        755                 760                 765

Lys Phe Ser His Arg Val Asp Lys Lys Pro Asn Arg Gln Leu Ile Asn
    770                 775                 780

Asp Thr Ile Tyr Ser Thr Arg Val Lys Asp Asp Lys Arg Tyr Leu Ile
785                 790                 795                 800

Asn Thr Leu Lys Asn Leu Tyr Asp Lys Ser Asn Gly Asp Leu Lys Glu
                805                 810                 815

Arg Met Gln Lys Asp Pro Glu Ser Leu Leu Met Tyr His His Asp Pro
            820                 825                 830

Gln Thr Phe Glu Lys Leu Lys Ile Val Met Ser Gln Tyr Glu Asn Glu
        835                 840                 845

Lys Asn Pro Leu Ala Lys Tyr Phe Glu Glu Thr Gly Gln Tyr Leu Thr
    850                 855                 860

Lys Tyr Ala Lys His Asp Asn Gly Pro Ala Ile His Lys Ile Lys Tyr
865                 870                 875                 880

Tyr Gly Asn Lys Leu Val Glu His Leu Asp Ile Thr Lys Asn Tyr His
                885                 890                 895

Asn Pro Gln Asn Lys Val Val Gln Leu Ser Gln Lys Ser Phe Arg Phe
            900                 905                 910

Asp Val Tyr Gln Thr Asp Lys Gly Tyr Lys Phe Ile Ser Ile Ala Tyr
        915                 920                 925

Leu Thr Leu Lys Asn Glu Lys Asn Tyr Tyr Ala Ile Ser Gln Glu Lys
    930                 935                 940

Tyr Asp Gln Leu Lys Ser Glu Lys Lys Ile Ser Asn Asn Ala Val Phe
945                 950                 955                 960

Ile Gly Ser Phe Tyr Thr Ser Asp Ile Ile Glu Ile Asn Asn Glu Lys
                965                 970                 975

Phe Arg Val Ile Gly Val Asn Ser Asp Lys Asn Asn Leu Ile Glu Val
            980                 985                 990

Asp Arg Ile Asp Ile Arg Gln Lys  Glu Phe Ile Glu Leu  Glu Glu Glu
        995                 1000                1005

Lys Lys  Asn Asn Arg Ile Lys  Val Thr Ile Gly Arg  Lys Thr Thr
    1010                1015                1020

Asn Ile  Glu Lys Phe His Thr  Asp Ile Leu Gly Asn  Met Tyr Lys
    1025                1030                1035

Ser Lys  Arg Pro Lys Ala Pro  Gln Leu Val Phe Lys  Lys Gly
    1040                1045                1050
```

<210> SEQ ID NO 6
<211> LENGTH: 1053
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1053)
<223> OTHER INFORMATION: M-SauCas9R420A

<400> SEQUENCE: 6

```
Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
```

-continued

```
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Ala Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445
```

-continued

```
Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860
```

```
Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                 1005

Asn Asp  Lys Arg Pro Pro Arg  Ile Ile Lys Thr Ile  Ala Ser Lys
    1010                 1015                 1020

Thr Gln  Ser Ile Lys Lys Tyr  Ser Thr Asp Ile Leu  Gly Asn Leu
    1025                 1030                 1035

Tyr Glu  Val Lys Ser Lys Lys  His Pro Gln Ile Ile  Lys Lys Gly
    1040                 1045                 1050


<210> SEQ ID NO 7
<211> LENGTH: 1056
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1056)
<223> OTHER INFORMATION: M-SluCas9R414A

<400> SEQUENCE: 7

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
            100                 105                 110

Ala Lys Arg Arg Gly Ile His Lys Ile Asp Val Ile Asp Ser Asn Asp
        115                 120                 125

Asp Val Gly Asn Glu Leu Ser Thr Lys Glu Gln Leu Asn Lys Asn Ser
    130                 135                 140

Lys Leu Leu Lys Asp Lys Phe Val Cys Gln Ile Gln Leu Glu Arg Met
145                 150                 155                 160
```

```
Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Gly Lys Gly Ser Pro Tyr Gly Trp
    210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
    290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
        355                 360                 365

Lys Leu Thr Glu Leu Asp Ile Leu Leu Asn Glu Glu Asp Lys Glu Asn
    370                 375                 380

Ile Ala Gln Leu Thr Gly Tyr Thr Gly Thr His Arg Leu Ser Leu Lys
385                 390                 395                 400

Cys Ile Arg Leu Val Leu Glu Glu Gln Trp Tyr Ser Ser Ala Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
    450                 455                 460

Lys Ile Ile Glu Lys Tyr Gly Val Pro Glu Asp Ile Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
        515                 520                 525

His Asp Glu Gln Glu Gly Lys Cys Leu Tyr Ser Leu Glu Ser Ile Pro
    530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575
```

-continued

```
Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
        675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
    770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815

Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
        835                 840                 845

Glu Lys Asn Pro Leu Ala Lys Tyr His Glu Glu Thr Gly Glu Tyr Leu
    850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
            900                 905                 910

Phe Asp Val Tyr Leu Thr Asp Lys Gly Tyr Lys Phe Ile Thr Ile Ser
        915                 920                 925

Tyr Leu Asp Val Leu Lys Lys Asp Asn Tyr Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
            980                 985                 990

Leu Asp Leu Pro Asp Ile Arg Tyr  Lys Glu Tyr Cys Glu  Leu Asn Asn
```

```
        995                 1000                1005

Ile Lys  Gly Glu Pro Arg Ile  Lys Lys Thr Ile Gly  Lys Lys Val
    1010                 1015                 1020

Asn Ser  Ile Glu Lys Leu Thr  Thr Asp Val Leu Gly  Asn Val Phe
    1025                 1030                 1035

Thr Asn  Thr Gln Tyr Thr Lys  Pro Gln Leu Leu Phe  Lys Arg Gly
    1040                 1045                 1050

Asn Gly  Gly
    1055


<210> SEQ ID NO 8
<211> LENGTH: 1057
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1057)
<223> OTHER INFORMATION: MGib11SpaCas9-3E410A

<400> SEQUENCE: 8

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Leu Leu Leu Thr Glu Tyr Asp Leu Ile Asn Lys Glu
65                  70                  75                  80

Gln Ile Pro Thr Ser Asn Asn Pro Tyr Gln Ile Arg Val Lys Gly Leu
                85                  90                  95

Ser Glu Ile Leu Ser Lys Asp Glu Leu Ala Ile Ala Leu Leu His Leu
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270
```

```
Gln Arg Asp Asn Ser Glu Lys Leu Glu Tyr His Glu Lys Tyr His Ile
        275                 280                 285

Ile Glu Asn Val Phe Lys Gln Lys Lys Lys Pro Thr Leu Lys Gln Ile
    290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
            340                 345                 350

Leu Asn Gln Ile Ala Glu Ile Leu Thr Ile Tyr Gln Asp Lys Asp Ser
        355                 360                 365

Ile Val Ala Glu Leu Gly Gln Leu Glu Tyr Leu Met Ser Glu Ala Asp
    370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Ala Leu Trp His Ser Ser
                405                 410                 415

Met Asn Gln Met Glu Val Phe Thr Tyr Leu Asn Met Arg Pro Lys Lys
            420                 425                 430

Tyr Glu Leu Lys Gly Tyr Gln Arg Ile Pro Thr Asp Met Ile Asp Asp
        435                 440                 445

Ala Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525

Ile Arg Leu His Asp Gln Gln Glu Gly Lys Cys Leu Tyr Ser Leu Glu
    530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
            580                 585                 590

Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
    610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Ser Tyr Leu Lys Ala Tyr Phe Ser Ala Asn
            660                 665                 670

Asn Met Asp Val Lys Val Lys Thr Ile Asn Gly Ser Phe Thr Asn His
        675                 680                 685

Leu Arg Lys Val Trp Arg Phe Asp Lys Tyr Arg Asn His Gly Tyr Lys
```

-continued

```
    690                 695                 700

His His Ala Glu Asp Ala Leu Ile Ile Ala Asn Ala Asp Phe Leu Phe
705                 710                 715                 720

Lys Glu Asn Lys Lys Leu Gln Asn Thr Asn Lys Ile Leu Glu Lys Pro
                725                 730                 735

Thr Ile Glu Asn Asn Thr Lys Lys Val Thr Val Glu Lys Glu Glu Asp
            740                 745                 750

Tyr Asn Asn Val Phe Glu Thr Pro Lys Leu Val Glu Asp Ile Lys Gln
        755                 760                 765

Tyr Arg Asp Tyr Lys Phe Ser His Arg Val Asp Lys Lys Pro Asn Arg
    770                 775                 780

Gln Leu Ile Asn Asp Thr Leu Tyr Ser Thr Arg Met Lys Asp Glu His
785                 790                 795                 800

Asp Tyr Ile Val Gln Thr Ile Thr Asp Ile Tyr Gly Lys Asp Asn Thr
                805                 810                 815

Asn Leu Lys Lys Gln Phe Asn Lys Asn Pro Glu Lys Phe Leu Met Tyr
            820                 825                 830

Gln Asn Asp Pro Lys Thr Phe Glu Lys Leu Ser Ile Ile Met Lys Gln
        835                 840                 845

Tyr Ser Asp Glu Lys Asn Pro Leu Ala Lys Tyr Tyr Glu Glu Thr Gly
    850                 855                 860

Glu Tyr Leu Thr Lys Tyr Ser Lys Lys Asn Asn Gly Pro Ile Val Lys
865                 870                 875                 880

Lys Ile Lys Leu Leu Gly Asn Lys Val Gly Asn His Leu Asp Val Thr
                885                 890                 895

Asn Lys Tyr Glu Asn Ser Thr Lys Lys Leu Val Lys Leu Ser Ile Lys
            900                 905                 910

Asn Tyr Arg Phe Asp Val Tyr Leu Thr Glu Lys Gly Tyr Lys Phe Val
        915                 920                 925

Thr Ile Ala Tyr Leu Asn Val Phe Lys Lys Asp Asn Tyr Tyr Tyr Ile
    930                 935                 940

Pro Lys Asp Lys Tyr Gln Glu Leu Lys Glu Lys Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp  Ile Lys Tyr Lys Asp  Tyr Cys Glu
        995                 1000                1005

Ile Asn  Asn Ile Lys Gly Glu  Pro Arg Ile Lys Lys  Thr Ile Gly
    1010                1015                1020

Lys Lys  Thr Glu Ser Ile Glu  Lys Phe Thr Thr Asp  Val Leu Gly
    1025                1030                1035

Asn Leu  Tyr Leu His Ser Thr  Glu Lys Ala Pro Gln  Leu Ile Phe
    1040                1045                1050

Lys Arg  Gly Leu
    1055
```

<210> SEQ ID NO 9
<211> LENGTH: 1056
<212> TYPE: PRT
<213> ORGANISM: Artificial Sequence
<220> FEATURE:
<223> OTHER INFORMATION: Synthetic
<220> FEATURE:

```
<221> NAME/KEY: misc_feature
<222> LOCATION: (1)..(1056)
<223> OTHER INFORMATION: SluCas9

<400> SEQUENCE: 9

Met Asn Gln Lys Phe Ile Leu Gly Leu Asp Ile Gly Ile Thr Ser Val
1               5                   10                  15

Gly Tyr Gly Leu Ile Asp Tyr Glu Thr Lys Asn Ile Ile Asp Ala Gly
            20                  25                  30

Val Arg Leu Phe Pro Glu Ala Asn Val Glu Asn Asn Glu Gly Arg Arg
        35                  40                  45

Ser Lys Arg Gly Ser Arg Arg Leu Lys Arg Arg Arg Ile His Arg Leu
    50                  55                  60

Glu Arg Val Lys Lys Leu Leu Glu Asp Tyr Asn Leu Leu Asp Gln Ser
65                  70                  75                  80

Gln Ile Pro Gln Ser Thr Asn Pro Tyr Ala Ile Arg Val Lys Gly Leu
                85                  90                  95

Ser Glu Ala Leu Ser Lys Asp Glu Leu Val Ile Ala Leu Leu His Ile
            100                 105                 110

Ala Lys Arg Arg Gly Ile His Lys Ile Asp Val Ile Asp Ser Asn Asp
        115                 120                 125

Asp Val Gly Asn Glu Leu Ser Thr Lys Glu Gln Leu Asn Lys Asn Ser
    130                 135                 140

Lys Leu Leu Lys Asp Lys Phe Val Cys Gln Ile Gln Leu Glu Arg Met
145                 150                 155                 160

Asn Glu Gly Gln Val Arg Gly Glu Lys Asn Arg Phe Lys Thr Ala Asp
                165                 170                 175

Ile Ile Lys Glu Ile Ile Gln Leu Leu Asn Val Gln Lys Asn Phe His
            180                 185                 190

Gln Leu Asp Glu Asn Phe Ile Asn Lys Tyr Ile Glu Leu Val Glu Met
        195                 200                 205

Arg Arg Glu Tyr Phe Glu Gly Pro Gly Lys Gly Ser Pro Tyr Gly Trp
    210                 215                 220

Glu Gly Asp Pro Lys Ala Trp Tyr Glu Thr Leu Met Gly His Cys Thr
225                 230                 235                 240

Tyr Phe Pro Asp Glu Leu Arg Ser Val Lys Tyr Ala Tyr Ser Ala Asp
                245                 250                 255

Leu Phe Asn Ala Leu Asn Asp Leu Asn Asn Leu Val Ile Gln Arg Asp
            260                 265                 270

Gly Leu Ser Lys Leu Glu Tyr His Glu Lys Tyr His Ile Ile Glu Asn
        275                 280                 285

Val Phe Lys Gln Lys Lys Lys Pro Thr Leu Lys Gln Ile Ala Asn Glu
    290                 295                 300

Ile Asn Val Asn Pro Glu Asp Ile Lys Gly Tyr Arg Ile Thr Lys Ser
305                 310                 315                 320

Gly Lys Pro Gln Phe Thr Glu Phe Lys Leu Tyr His Asp Leu Lys Ser
                325                 330                 335

Val Leu Phe Asp Gln Ser Ile Leu Glu Asn Glu Asp Val Leu Asp Gln
            340                 345                 350

Ile Ala Glu Ile Leu Thr Ile Tyr Gln Asp Lys Asp Ser Ile Lys Ser
        355                 360                 365

Lys Leu Thr Glu Leu Asp Ile Leu Leu Asn Glu Glu Asp Lys Glu Asn
    370                 375                 380

Ile Ala Gln Leu Thr Gly Tyr Thr Gly Thr His Arg Leu Ser Leu Lys
```

-continued

```
385                 390                 395                 400

Cys Ile Arg Leu Val Leu Glu Glu Gln Trp Tyr Ser Ser Arg Asn Gln
                405                 410                 415

Met Glu Ile Phe Thr His Leu Asn Ile Lys Pro Lys Lys Ile Asn Leu
            420                 425                 430

Thr Ala Ala Asn Lys Ile Pro Lys Ala Met Ile Asp Glu Phe Ile Leu
        435                 440                 445

Ser Pro Val Val Lys Arg Thr Phe Gly Gln Ala Ile Asn Leu Ile Asn
    450                 455                 460

Lys Ile Ile Glu Lys Tyr Gly Val Pro Glu Asp Ile Ile Ile Glu Leu
465                 470                 475                 480

Ala Arg Glu Asn Asn Ser Lys Asp Lys Gln Lys Phe Ile Asn Glu Met
                485                 490                 495

Gln Lys Lys Asn Glu Asn Thr Arg Lys Arg Ile Asn Glu Ile Ile Gly
            500                 505                 510

Lys Tyr Gly Asn Gln Asn Ala Lys Arg Leu Val Glu Lys Ile Arg Leu
        515                 520                 525

His Asp Glu Gln Glu Gly Lys Cys Leu Tyr Ser Leu Glu Ser Ile Pro
    530                 535                 540

Leu Glu Asp Leu Leu Asn Asn Pro Asn His Tyr Glu Val Asp His Ile
545                 550                 555                 560

Ile Pro Arg Ser Val Ser Phe Asp Asn Ser Tyr His Asn Lys Val Leu
                565                 570                 575

Val Lys Gln Ser Glu Asn Ser Lys Lys Ser Asn Leu Thr Pro Tyr Gln
            580                 585                 590

Tyr Phe Asn Ser Gly Lys Ser Lys Leu Ser Tyr Asn Gln Phe Lys Gln
        595                 600                 605

His Ile Leu Asn Leu Ser Lys Ser Gln Asp Arg Ile Ser Lys Lys Lys
    610                 615                 620

Lys Glu Tyr Leu Leu Glu Glu Arg Asp Ile Asn Lys Phe Glu Val Gln
625                 630                 635                 640

Lys Glu Phe Ile Asn Arg Asn Leu Val Asp Thr Arg Tyr Ala Thr Arg
                645                 650                 655

Glu Leu Thr Asn Tyr Leu Lys Ala Tyr Phe Ser Ala Asn Asn Met Asn
            660                 665                 670

Val Lys Val Lys Thr Ile Asn Gly Ser Phe Thr Asp Tyr Leu Arg Lys
        675                 680                 685

Val Trp Lys Phe Lys Lys Glu Arg Asn His Gly Tyr Lys His His Ala
    690                 695                 700

Glu Asp Ala Leu Ile Ile Ala Asn Ala Asp Phe Leu Phe Lys Glu Asn
705                 710                 715                 720

Lys Lys Leu Lys Ala Val Asn Ser Val Leu Glu Lys Pro Glu Ile Glu
                725                 730                 735

Thr Lys Gln Leu Asp Ile Gln Val Asp Ser Glu Asp Asn Tyr Ser Glu
            740                 745                 750

Met Phe Ile Ile Pro Lys Gln Val Gln Asp Ile Lys Asp Phe Arg Asn
        755                 760                 765

Phe Lys Tyr Ser His Arg Val Asp Lys Lys Pro Asn Arg Gln Leu Ile
    770                 775                 780

Asn Asp Thr Leu Tyr Ser Thr Arg Lys Lys Asp Asn Ser Thr Tyr Ile
785                 790                 795                 800

Val Gln Thr Ile Lys Asp Ile Tyr Ala Lys Asp Asn Thr Thr Leu Lys
                805                 810                 815
```

-continued

```
Lys Gln Phe Asp Lys Ser Pro Glu Lys Phe Leu Met Tyr Gln His Asp
            820                 825                 830

Pro Arg Thr Phe Glu Lys Leu Glu Val Ile Met Lys Gln Tyr Ala Asn
        835                 840                 845

Glu Lys Asn Pro Leu Ala Lys Tyr His Glu Glu Thr Gly Glu Tyr Leu
    850                 855                 860

Thr Lys Tyr Ser Lys Lys Asn Asn Gly Pro Ile Val Lys Ser Leu Lys
865                 870                 875                 880

Tyr Ile Gly Asn Lys Leu Gly Ser His Leu Asp Val Thr His Gln Phe
                885                 890                 895

Lys Ser Ser Thr Lys Lys Leu Val Lys Leu Ser Ile Lys Pro Tyr Arg
            900                 905                 910

Phe Asp Val Tyr Leu Thr Asp Lys Gly Tyr Lys Phe Ile Thr Ile Ser
        915                 920                 925

Tyr Leu Asp Val Leu Lys Lys Asp Asn Tyr Tyr Tyr Ile Pro Glu Gln
    930                 935                 940

Lys Tyr Asp Lys Leu Lys Leu Gly Lys Ala Ile Asp Lys Asn Ala Lys
945                 950                 955                 960

Phe Ile Ala Ser Phe Tyr Lys Asn Asp Leu Ile Lys Leu Asp Gly Glu
                965                 970                 975

Ile Tyr Lys Ile Ile Gly Val Asn Ser Asp Thr Arg Asn Met Ile Glu
            980                 985                 990

Leu Asp Leu Pro Asp Ile Arg Tyr  Lys Glu Tyr Cys Glu  Leu Asn Asn
        995                 1000                1005

Ile Lys  Gly Glu Pro Arg Ile  Lys Lys Thr Ile Gly  Lys Lys Val
    1010                1015                1020

Asn Ser  Ile Glu Lys Leu Thr  Thr Asp Val Leu Gly  Asn Val Phe
    1025                1030                1035

Thr Asn  Thr Gln Tyr Thr Lys  Pro Gln Leu Leu Phe  Lys Arg Gly
    1040                1045                1050

Asn Gly  Gly
    1055
```

<210> SEQ ID NO 10
<211> LENGTH: 150
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(150)
<223> OTHER INFORMATION: sgRNA_Ex1

<400> SEQUENCE: 10

```
ggugaacgug gaugaaguug guuuuaguac ucuggaaaca gaaucuacug aaacaagaca     60

auaugucgug uuuaucccau caauuuauug gugggauuuu uuucuagcau aaccccuugg    120

ggccucuaaa cgggucuuga gggguuuuuu                                     150
```

<210> SEQ ID NO 11
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)

<223> OTHER INFORMATION: R01-1-A

<400> SEQUENCE: 11
ggtgaacgtg gatgaagttg tggggtac 28

<210> SEQ ID NO 12
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-1-B

<400> SEQUENCE: 12
gcggtacccc acaacttcat ccacgttcac cgg 33

<210> SEQ ID NO 13
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-2-A

<400> SEQUENCE: 13
agtgaacgtg gatgaagttg tggggtac 28

<210> SEQ ID NO 14
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-2-B

<400> SEQUENCE: 14
gcggtacccc acaacttcat ccacgttcac tgg 33

<210> SEQ ID NO 15
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-3-A

<400> SEQUENCE: 15
cgtgaacgtg gatgaagttg tggggtac 28

<210> SEQ ID NO 16
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature

<222> LOCATION: (1)..(33)
<223> OTHER INFORMATION: R01-3-B

<400> SEQUENCE: 16
gcggtacccc acaacttcat ccacgttcac ggg 33

<210> SEQ ID NO 17
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-4-A

<400> SEQUENCE: 17
tgtgaacgtg gatgaagttg tggggtac 28

<210> SEQ ID NO 18
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-4-B

<400> SEQUENCE: 18
gcggtacccc acaacttcat ccacgttcac agg 33

<210> SEQ ID NO 19
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-5-A

<400> SEQUENCE: 19
gatgaacgtg gatgaagttg tggggtac 28

<210> SEQ ID NO 20
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-5-B

<400> SEQUENCE: 20
gcggtacccc acaacttcat ccacgttcat cgg 33

<210> SEQ ID NO 21
<211> LENGTH: 28
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<222> LOCATION: (1)..(28)
<223> OTHER INFORMATION: R01-6-A

<400> SEQUENCE: 21
gctgaacgtg gatgaagttg tggggtac 28

<210> SEQ ID NO 22
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-6-B

<400> SEQUENCE: 22
gcggtacccc acaacttcat ccacgttcag cgg 33

<210> SEQ ID NO 23
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-7-A

<400> SEQUENCE: 23
gttgaacgtg gatgaagttg tggggtac 28

<210> SEQ ID NO 24
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-7-B

<400> SEQUENCE: 24
gcggtacccc acaacttcat ccacgttcaa cgg 33

<210> SEQ ID NO 25
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-8-A

<400> SEQUENCE: 25
ggagaacgtg gatgaagttg tggggtac 28

<210> SEQ ID NO 26
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-8-B

<400> SEQUENCE: 26
gcggtacccc acaacttcat ccacgttctc cgg 33

<210> SEQ ID NO 27
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-9-A

<400> SEQUENCE: 27
ggcgaacgtg gatgaagttg tggggtac 28

<210> SEQ ID NO 28
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-9-B

<400> SEQUENCE: 28
gcggtacccc acaacttcat ccacgttcgc cgg 33

<210> SEQ ID NO 29
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-10-A

<400> SEQUENCE: 29
ggggaacgtg gatgaagttg tggggtac 28

<210> SEQ ID NO 30
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-10-B

<400> SEQUENCE: 30
gcggtacccc acaacttcat ccacgttccc cgg 33

<210> SEQ ID NO 31
<211> LENGTH: 28
<212> TYPE: DNA
<213> ORGANISM: Artificial Sequence
<220> FEATURE:

-continued

<223> OTHER INFORMATION: Synthetic
<220> FEATURE:
<221> NAME/KEY: misc_feature
<222> LOCATION: (1)..(28)
<223> OTHER INFORMATION: R01-11-A

<400> SEQUENCE: 31
ggtaaacgtg gatgaagttg tggggtac 28

<210> SEQ ID NO 32
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-11-B

<400> SEQUENCE: 32
gcggtacccc acaacttcat ccacgtttac cgg 33

<210> SEQ ID NO 33
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-12-A

<400> SEQUENCE: 33
ggtcaacgtg gatgaagttg tggggtac 28

<210> SEQ ID NO 34
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-12-B

<400> SEQUENCE: 34
gcggtacccc acaacttcat ccacgttgac cgg 33

<210> SEQ ID NO 35
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-13-A

<400> SEQUENCE: 35
ggttaacgtg gatgaagttg tggggtac 28

<210> SEQ ID NO 36
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-13-B

<400> SEQUENCE: 36
gcggtacccc acaacttcat ccacgttaac cgg 33

<210> SEQ ID NO 37
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-14-A

<400> SEQUENCE: 37
ggtgcacgtg gatgaagttg tggggtac 28

<210> SEQ ID NO 38
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-14-B

<400> SEQUENCE: 38
gcggtacccc acaacttcat ccacgtgcac cgg 33

<210> SEQ ID NO 39
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-15-A

<400> SEQUENCE: 39
ggtgtacgtg gatgaagttg tggggtac 28

<210> SEQ ID NO 40
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-15-B

<400> SEQUENCE: 40
gcggtacccc acaacttcat ccacgtacac cgg 33

<210> SEQ ID NO 41
<211> LENGTH: 28
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-16-A

<400> SEQUENCE: 41
ggtggacgtg gatgaagttg tggggtac 28

<210> SEQ ID NO 42
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-16-B

<400> SEQUENCE: 42
gcggtacccc acaacttcat ccacgtccac cgg 33

<210> SEQ ID NO 43
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-17-A

<400> SEQUENCE: 43
ggtgaccgtg gatgaagttg tggggtac 28

<210> SEQ ID NO 44
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-17-B

<400> SEQUENCE: 44
gcggtacccc acaacttcat ccacggtcac cgg 33

<210> SEQ ID NO 45
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-18-A

<400> SEQUENCE: 45
ggtgatcgtg gatgaagttg tggggtac 28

<210> SEQ ID NO 46
<211> LENGTH: 33

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-18-B

<400> SEQUENCE: 46
gcggtacccc acaacttcat ccacgatcac cgg 33

<210> SEQ ID NO 47
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-19-A

<400> SEQUENCE: 47
ggtgagcgtg gatgaagttg tggggtac 28

<210> SEQ ID NO 48
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-19-B

<400> SEQUENCE: 48
gcggtacccc acaacttcat ccacgctcac cgg 33

<210> SEQ ID NO 49
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-20-A

<400> SEQUENCE: 49
ggtgaaagtg gatgaagttg tggggtac 28

<210> SEQ ID NO 50
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-20-B

<400> SEQUENCE: 50
gcggtacccc acaacttcat ccactttcac cgg 33

<210> SEQ ID NO 51

<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-21-A

<400> SEQUENCE: 51
ggtgaatgtg gatgaagttg tggggtac 28

<210> SEQ ID NO 52
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-21-B

<400> SEQUENCE: 52
gcggtacccc acaacttcat ccacattcac cgg 33

<210> SEQ ID NO 53
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-22-A

<400> SEQUENCE: 53
ggtgaaggtg gatgaagttg tggggtac 28

<210> SEQ ID NO 54
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-22-B

<400> SEQUENCE: 54
gcggtacccc acaacttcat ccaccttcac cgg 33

<210> SEQ ID NO 55
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-23-A

<400> SEQUENCE: 55
ggtgaacatg gatgaagttg tggggtac 28

<210> SEQ ID NO 56
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-23-B

<400> SEQUENCE: 56
gcggtacccc acaacttcat ccatgttcac cgg 33

<210> SEQ ID NO 57
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-24-A

<400> SEQUENCE: 57
ggtgaacctg gatgaagttg tggggtac 28

<210> SEQ ID NO 58
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-24-B

<400> SEQUENCE: 58
gcggtacccc acaacttcat ccaggttcac cgg 33

<210> SEQ ID NO 59
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-25-A

<400> SEQUENCE: 59
ggtgaacttg gatgaagttg tggggtac 28

<210> SEQ ID NO 60
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-25-B

<400> SEQUENCE: 60
gcggtacccc acaacttcat ccaagttcac cgg 33

<210> SEQ ID NO 61
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-26-A

<400> SEQUENCE: 61
ggtgaacgag gatgaagttg tggggtac 28

<210> SEQ ID NO 62
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-26-B

<400> SEQUENCE: 62
gcggtacccc acaacttcat cctcgttcac cgg 33

<210> SEQ ID NO 63
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-27-A

<400> SEQUENCE: 63
ggtgaacgcg gatgaagttg tggggtac 28

<210> SEQ ID NO 64
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-27-B

<400> SEQUENCE: 64
gcggtacccc acaacttcat ccgcgttcac cgg 33

<210> SEQ ID NO 65
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-28-A

<400> SEQUENCE: 65
ggtgaacggg gatgaagttg tggggtac 28

<210> SEQ ID NO 66
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-28-B

<400> SEQUENCE: 66
gcggtacccc acaacttcat ccccgttcac cgg 33

<210> SEQ ID NO 67
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-29-A

<400> SEQUENCE: 67
ggtgaacgta gatgaagttg tggggtac 28

<210> SEQ ID NO 68
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-29-B

<400> SEQUENCE: 68
gcggtacccc acaacttcat ctacgttcac cgg 33

<210> SEQ ID NO 69
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-30-A

<400> SEQUENCE: 69
ggtgaacgtc gatgaagttg tggggtac 28

<210> SEQ ID NO 70
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-30-B

<400> SEQUENCE: 70
gcggtacccc acaacttcat cgacgttcac cgg 33

<210> SEQ ID NO 71
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-31-A

<400> SEQUENCE: 71
ggtgaacgtt gatgaagttg tggggtac 28

<210> SEQ ID NO 72
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-31-B

<400> SEQUENCE: 72
gcggtacccc acaacttcat caacgttcac cgg 33

<210> SEQ ID NO 73
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-32-A

<400> SEQUENCE: 73
ggtgaacgtg aatgaagttg tggggtac 28

<210> SEQ ID NO 74
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-32-B

<400> SEQUENCE: 74
gcggtacccc acaacttcat tcacgttcac cgg 33

<210> SEQ ID NO 75
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-33-A

<400> SEQUENCE: 75
ggtgaacgtg catgaagttg tggggtac 28

<210> SEQ ID NO 76
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-33-B

<400> SEQUENCE: 76
gcggtacccc acaacttcat gcacgttcac cgg 33

<210> SEQ ID NO 77
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-34-A

<400> SEQUENCE: 77
ggtgaacgtg tatgaagttg tggggtac 28

<210> SEQ ID NO 78
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-34-B

<400> SEQUENCE: 78
gcggtacccc acaacttcat acacgttcac cgg 33

<210> SEQ ID NO 79
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-35-A

<400> SEQUENCE: 79
ggtgaacgtg gctgaagttg tggggtac 28

<210> SEQ ID NO 80
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-35-B

<400> SEQUENCE: 80
gcggtacccc acaacttcag ccacgttcac cgg 33

<210> SEQ ID NO 81
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-36-A

<400> SEQUENCE: 81
ggtgaacgtg gttgaagttg tggggtac 28

<210> SEQ ID NO 82
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-36-B

<400> SEQUENCE: 82
gcggtacccc acaacttcaa ccacgttcac cgg 33

<210> SEQ ID NO 83
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-37-A

<400> SEQUENCE: 83
ggtgaacgtg ggtgaagttg tggggtac 28

<210> SEQ ID NO 84
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-37-B

<400> SEQUENCE: 84
gcggtacccc acaacttcac ccacgttcac cgg 33

<210> SEQ ID NO 85
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-38-A

<400> SEQUENCE: 85
ggtgaacgtg gaagaagttg tggggtac 28

<210> SEQ ID NO 86
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-38-B

<400> SEQUENCE: 86
gcggtacccc acaacttctt ccacgttcac cgg 33

<210> SEQ ID NO 87
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-39-A

<400> SEQUENCE: 87
ggtgaacgtg gacgaagttg tggggtac 28

<210> SEQ ID NO 88
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-39-B

<400> SEQUENCE: 88
gcggtacccc acaacttcgt ccacgttcac cgg 33

<210> SEQ ID NO 89
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-40-A

<400> SEQUENCE: 89
ggtgaacgtg gaggaagttg tggggtac 28

<210> SEQ ID NO 90
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)

<223> OTHER INFORMATION: R01-40-B

<400> SEQUENCE: 90
gcggtacccc acaacttcct ccacgttcac cgg 33

<210> SEQ ID NO 91
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-41-A

<400> SEQUENCE: 91
ggtgaacgtg gataaagttg tggggtac 28

<210> SEQ ID NO 92
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-41-B

<400> SEQUENCE: 92
gcggtacccc acaactttat ccacgttcac cgg 33

<210> SEQ ID NO 93
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-42-A

<400> SEQUENCE: 93
ggtgaacgtg gatcaagttg tggggtac 28

<210> SEQ ID NO 94
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-42-B

<400> SEQUENCE: 94
gcggtacccc acaacttgat ccacgttcac cgg 33

<210> SEQ ID NO 95
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature -continued

<222> LOCATION: (1)..(28)
<223> OTHER INFORMATION: R01-43-A

<400> SEQUENCE: 95
ggtgaacgtg gattaagttg tggggtac 28

<210> SEQ ID NO 96
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-43-B

<400> SEQUENCE: 96
gcggtacccc acaacttaat ccacgttcac cgg 33

<210> SEQ ID NO 97
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-44-A

<400> SEQUENCE: 97
ggtgaacgtg gatgcagttg tggggtac 28

<210> SEQ ID NO 98
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-44-B

<400> SEQUENCE: 98
gcggtacccc acaactgcat ccacgttcac cgg 33

<210> SEQ ID NO 99
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-45-A

<400> SEQUENCE: 99
ggtgaacgtg gatgtagttg tggggtac 28

<210> SEQ ID NO 100
<211> LENGTH: 33
<212> TYPE: DNA
<213> ORGANISM: Artificial Sequence
<220> FEATURE:
<223> OTHER INFORMATION: Synthetic
<220> FEATURE:

<221> NAME/KEY: misc_feature
<222> LOCATION: (1)..(33)
<223> OTHER INFORMATION: R01-45-B

<400> SEQUENCE: 100
gcggtacccc acaactacat ccacgttcac cgg 33

<210> SEQ ID NO 101
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-46-A

<400> SEQUENCE: 101
ggtgaacgtg gatggagttg tggggtac 28

<210> SEQ ID NO 102
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-46-B

<400> SEQUENCE: 102
gcggtacccc acaactccat ccacgttcac cgg 33

<210> SEQ ID NO 103
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-47-A

<400> SEQUENCE: 103
ggtgaacgtg gatgacgttg tggggtac 28

<210> SEQ ID NO 104
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-47-B

<400> SEQUENCE: 104
gcggtacccc acaacgtcat ccacgttcac cgg 33

<210> SEQ ID NO 105
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-48-A

<400> SEQUENCE: 105
ggtgaacgtg gatgatgttg tggggtac 28

<210> SEQ ID NO 106
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-48-B

<400> SEQUENCE: 106
gcggtacccc acaacatcat ccacgttcac cgg 33

<210> SEQ ID NO 107
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-49-A

<400> SEQUENCE: 107
ggtgaacgtg gatgaggttg tggggtac 28

<210> SEQ ID NO 108
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-49-B

<400> SEQUENCE: 108
gcggtacccc acaacctcat ccacgttcac cgg 33

<210> SEQ ID NO 109
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(27)
<223> OTHER INFORMATION: R01-50-A

<400> SEQUENCE: 109
ggtgaacgtg gatgaaattg tggggta 27

<210> SEQ ID NO 110
<211> LENGTH: 33
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(33)
<223> OTHER INFORMATION: R01-50-B

<400> SEQUENCE: 110
gcggtacccc acaatttcat ccacgttcac cgg 33

<210> SEQ ID NO 111
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-51-A

<400> SEQUENCE: 111
ggtgaacgtg gatgaacttg tggggtac 28

<210> SEQ ID NO 112
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-51-B

<400> SEQUENCE: 112
gcggtacccc acaagttcat ccacgttcac cgg 33

<210> SEQ ID NO 113
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-52-A

<400> SEQUENCE: 113
ggtgaacgtg gatgaatttg tggggtac 28

<210> SEQ ID NO 114
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-52-B

<400> SEQUENCE: 114
gcggtacccc acaaattcat ccacgttcac cgg 33

<210> SEQ ID NO 115
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-53-A

<400> SEQUENCE: 115
ggtgaacgtg gatgaagatg tggggtac 28

<210> SEQ ID NO 116
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-53-B

<400> SEQUENCE: 116
gcggtacccc acatcttcat ccacgttcac cgg 33

<210> SEQ ID NO 117
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-54-A

<400> SEQUENCE: 117
ggtgaacgtg gatgaagctg tggggtac 28

<210> SEQ ID NO 118
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-54-B

<400> SEQUENCE: 118
gcggtacccc acagcttcat ccacgttcac cgg 33

<210> SEQ ID NO 119
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-55-A

<400> SEQUENCE: 119
ggtgaacgtg gatgaaggtg tggggtac 28

<210> SEQ ID NO 120
<211> LENGTH: 33
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-55-B

<400> SEQUENCE: 120
gcggtacccc acaccttcat ccacgttcac cgg 33

<210> SEQ ID NO 121
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-56-A

<400> SEQUENCE: 121
ggtgaacgtg gatgaagtag tggggtac 28

<210> SEQ ID NO 122
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-56-B

<400> SEQUENCE: 122
gcggtacccc actacttcat ccacgttcac cgg 33

<210> SEQ ID NO 123
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-57-A

<400> SEQUENCE: 123
ggtgaacgtg gatgaagtcg tggggtac 28

<210> SEQ ID NO 124
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-57-B

<400> SEQUENCE: 124
gcggtacccc acgacttcat ccacgttcac cgg 33

<210> SEQ ID NO 125
<211> LENGTH: 28

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-58-A

<400> SEQUENCE: 125

ggtgaacgtg gatgaagtgg tggggtac                                    28


<210> SEQ ID NO 126
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-58-B

<400> SEQUENCE: 126

gcggtacccc accacttcat ccacgttcac cgg                              33


<210> SEQ ID NO 127
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-59-A

<400> SEQUENCE: 127

ggtgaacgtg gatgaagtta tggggtac                                    28


<210> SEQ ID NO 128
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-59-B

<400> SEQUENCE: 128

gcggtacccc ataacttcat ccacgttcac cgg                              33


<210> SEQ ID NO 129
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-60-A

<400> SEQUENCE: 129

ggtgaacgtg gatgaagttc tggggtac                                    28


<210> SEQ ID NO 130
```

<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-60-B

<400> SEQUENCE: 130
gcggtacccc agaacttcat ccacgttcac cgg 33

<210> SEQ ID NO 131
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: R01-61-A

<400> SEQUENCE: 131
ggtgaacgtg gatgaagttt tggggtac 28

<210> SEQ ID NO 132
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(33)
<223> OTHER INFORMATION: R01-61-B

<400> SEQUENCE: 132
gcggtacccc aaaacttcat ccacgttcac cgg 33

<210> SEQ ID NO 133
<211> LENGTH: 1057
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1057)
<223> OTHER INFORMATION: Gib11SpaCas9-1-M417L

<400> SEQUENCE: 133

Met Asn Gln Lys Phe Ile Leu Gly Leu Asp Ile Gly Ile Thr Ser Val
1 5 10 15

Gly Tyr Gly Leu Ile Asp Tyr Glu Thr Lys Asn Ile Ile Asp Ala Gly
20 25 30

Val Arg Leu Phe Pro Glu Ala Asn Val Glu Asn Asn Glu Gly Arg Arg
35 40 45

Ser Lys Arg Gly Ser Arg Arg Leu Lys Arg Arg Arg Ile His Arg Leu
50 55 60

Glu Arg Val Lys Leu Leu Leu Thr Glu Tyr Asp Leu Ile Asn Lys Glu
65 70 75 80

Gln Ile Pro Thr Ser Asn Asn Pro Tyr Gln Ile Arg Val Lys Gly Leu
85 90 95

Ser Glu Ile Leu Ser Lys Asp Glu Leu Ala Ile Ala Leu Leu His Leu

-continued

```
            100                 105                 110

Ala Lys Arg Arg Gly Ile His Asn Val Asp Val Ala Ala Asp Lys Glu
        115                 120                 125

Glu Thr Ala Ser Asp Ser Leu Ser Thr Lys Asp Gln Ile Asn Lys Asn
    130                 135                 140

Ala Lys Phe Leu Glu Ser Arg Tyr Val Cys Glu Leu Gln Lys Glu Arg
145                 150                 155                 160

Leu Glu Asn Glu Gly His Val Arg Gly Val Glu Asn Arg Phe Leu Thr
                165                 170                 175

Lys Asp Ile Val Arg Glu Ala Lys Lys Ile Ile Asp Thr Gln Met Gln
            180                 185                 190

Tyr Tyr Pro Glu Ile Asp Glu Thr Phe Lys Glu Lys Tyr Ile Ser Leu
        195                 200                 205

Val Glu Thr Arg Arg Glu Tyr Phe Glu Gly Pro Gly Gln Gly Ser Pro
    210                 215                 220

Phe Gly Trp Asn Gly Asp Leu Lys Lys Trp Tyr Glu Met Leu Met Gly
225                 230                 235                 240

His Cys Thr Tyr Phe Pro Gln Glu Leu Arg Ser Val Lys Tyr Ala Tyr
                245                 250                 255

Ser Ala Asp Leu Phe Asn Ala Leu Asn Asp Leu Asn Asn Leu Ile Ile
            260                 265                 270

Gln Arg Asp Asn Ser Glu Lys Leu Glu Tyr His Glu Lys Tyr His Ile
        275                 280                 285

Ile Glu Asn Val Phe Lys Gln Lys Lys Lys Pro Thr Leu Lys Gln Ile
    290                 295                 300

Ala Lys Glu Ile Gly Val Asn Pro Glu Asp Ile Lys Gly Tyr Arg Ile
305                 310                 315                 320

Thr Lys Ser Gly Thr Pro Glu Phe Thr Ser Phe Lys Leu Phe His Asp
                325                 330                 335

Leu Lys Lys Val Val Lys Asp His Ala Ile Leu Asp Asp Ile Asp Leu
            340                 345                 350

Leu Asn Gln Ile Ala Glu Ile Leu Thr Ile Tyr Gln Asp Lys Asp Ser
        355                 360                 365

Ile Val Ala Glu Leu Gly Gln Leu Glu Tyr Leu Met Ser Glu Ala Asp
    370                 375                 380

Lys Gln Ser Ile Ser Glu Leu Thr Gly Tyr Thr Gly Thr His Ser Leu
385                 390                 395                 400

Ser Leu Lys Cys Met Asn Met Ile Ile Asp Glu Leu Trp His Ser Ser
                405                 410                 415

Leu Asn Gln Met Glu Val Phe Thr Tyr Leu Asn Met Arg Pro Lys Lys
            420                 425                 430

Tyr Glu Leu Lys Gly Tyr Gln Arg Ile Pro Thr Asp Met Ile Asp Asp
        435                 440                 445

Ala Ile Leu Ser Pro Val Val Lys Arg Thr Phe Ile Gln Ser Ile Asn
    450                 455                 460

Val Ile Asn Lys Val Ile Glu Lys Tyr Gly Ile Pro Glu Asp Ile Ile
465                 470                 475                 480

Ile Glu Leu Ala Arg Glu Asn Asn Ser Asp Asp Arg Lys Lys Phe Ile
                485                 490                 495

Asn Asn Leu Gln Lys Lys Asn Glu Ala Thr Arg Lys Arg Ile Asn Glu
            500                 505                 510

Ile Ile Gly Gln Thr Gly Asn Gln Asn Ala Lys Arg Ile Val Glu Lys
        515                 520                 525
```

```
Ile Arg Leu His Asp Gln Gln Glu Gly Lys Cys Leu Tyr Ser Leu Glu
    530                 535                 540

Ser Ile Pro Leu Glu Asp Leu Leu Asn Asn Pro Asn His Tyr Glu Val
545                 550                 555                 560

Asp His Ile Ile Pro Arg Ser Val Ser Phe Asp Asn Ser Tyr His Asn
                565                 570                 575

Lys Val Leu Val Lys Gln Ser Glu Asn Ser Lys Lys Ser Asn Leu Thr
            580                 585                 590

Pro Tyr Gln Tyr Phe Asn Ser Gly Lys Ser Lys Leu Ser Tyr Asn Gln
        595                 600                 605

Phe Lys Gln His Ile Leu Asn Leu Ser Lys Ser Gln Asp Arg Ile Ser
    610                 615                 620

Lys Lys Lys Lys Glu Tyr Leu Leu Glu Glu Arg Asp Ile Asn Lys Phe
625                 630                 635                 640

Glu Val Gln Lys Glu Phe Ile Asn Arg Asn Leu Val Asp Thr Arg Tyr
                645                 650                 655

Ala Thr Arg Glu Leu Thr Asn Tyr Leu Lys Ala Tyr Phe Ser Ala Asn
            660                 665                 670

Asn Met Asn Val Lys Val Lys Thr Ile Asn Gly Ser Phe Thr Asp Tyr
        675                 680                 685

Leu Arg Lys Val Trp Lys Phe Lys Lys Glu Arg Asn His Gly Tyr Lys
    690                 695                 700

His His Ala Glu Asp Ala Leu Ile Ile Ala Asn Ala Asp Phe Leu Phe
705                 710                 715                 720

Lys Glu Asn Lys Lys Leu Lys Ala Val Asn Ser Val Leu Glu Lys Pro
                725                 730                 735

Glu Ile Glu Thr Lys Gln Leu Asp Ile Gln Val Asp Ser Glu Asp Asn
            740                 745                 750

Tyr Ser Glu Met Phe Ile Ile Pro Lys Gln Val Gln Asp Ile Lys Asp
        755                 760                 765

Phe Arg Asn Phe Lys Tyr Ser His Arg Val Asp Lys Lys Pro Asn Arg
    770                 775                 780

Gln Leu Ile Asn Asp Thr Leu Tyr Ser Thr Arg Lys Lys Asp Asn Ser
785                 790                 795                 800

Thr Tyr Ile Val Gln Thr Ile Lys Asp Ile Tyr Ala Lys Asp Asn Thr
                805                 810                 815

Thr Leu Lys Lys Gln Phe Asp Lys Ser Pro Glu Lys Phe Leu Met Tyr
            820                 825                 830

Gln His Asp Pro Arg Thr Phe Glu Lys Leu Glu Val Ile Met Lys Gln
        835                 840                 845

Tyr Ala Asn Glu Lys Asn Pro Leu Ala Lys Tyr His Glu Glu Thr Gly
    850                 855                 860

Glu Tyr Leu Thr Lys Tyr Ser Lys Lys Asn Asn Gly Pro Ile Val Lys
865                 870                 875                 880

Ser Leu Lys Tyr Ile Gly Asn Lys Leu Gly Ser His Leu Asp Val Thr
                885                 890                 895

His Gln Phe Lys Ser Ser Thr Lys Lys Leu Val Lys Leu Ser Ile Lys
            900                 905                 910

Asn Tyr Arg Phe Asp Val Tyr Leu Thr Glu Lys Gly Tyr Lys Phe Val
        915                 920                 925

Thr Ile Ala Tyr Leu Asn Val Phe Lys Lys Asp Asn Tyr Tyr Tyr Ile
    930                 935                 940
```

-continued

```
Pro Lys Asp Lys Tyr Gln Glu Leu Lys Glu Lys Lys Lys Ile Lys Asp
945                 950                 955                 960

Thr Asp Gln Phe Ile Ala Ser Phe Tyr Lys Asn Asp Leu Ile Lys Leu
                965                 970                 975

Asn Gly Asp Leu Tyr Lys Ile Ile Gly Val Asn Ser Asp Asp Arg Asn
            980                 985                 990

Ile Ile Glu Leu Asp Tyr Tyr Asp  Ile Lys Tyr Lys Asp  Tyr Cys Glu
        995                 1000                1005

Ile Asn  Asn Ile Lys Gly Glu  Pro Arg Ile Lys Lys  Thr Ile Gly
    1010                 1015                1020

Lys Lys  Thr Glu Ser Ile Glu  Lys Phe Thr Thr Asp  Val Leu Gly
    1025                 1030                1035

Asn Leu  Tyr Leu His Ser Thr  Glu Lys Ala Pro Gln  Leu Ile Phe
    1040                 1045                1050

Lys Arg  Gly Leu
    1055
```